(12) United States Patent
Dolle et al.

(10) Patent No.: US 7,576,207 B2
(45) Date of Patent: Aug. 18, 2009

(54) SPIROCYCLIC HETEROCYCLIC DERIVATIVES AND METHODS OF THEIR USE

(75) Inventors: Roland E. Dolle, King of Prussia, PA (US); Bertrand Le Bourdonnec, East Fallowfield, PA (US); Guo-Hua Chu, Exton, PA (US)

(73) Assignee: Adolor Corporation, Exton, PA (US)

( * ) Notice: Subject to any disclaimer, the term of this patent is extended or adjusted under 35 U.S.C. 154(b) by 191 days.

(21) Appl. No.: 11/696,585

(22) Filed: Apr. 4, 2007

(65) Prior Publication Data

US 2007/0269374 A1 Nov. 22, 2007

Related U.S. Application Data

(60) Provisional application No. 60/790,416, filed on Apr. 6, 2006.

(51) Int. Cl.
*C07D 401/00* (2006.01)
*A01N 43/42* (2006.01)
(52) U.S. Cl. .................................. 546/17; 514/278
(58) Field of Classification Search .................. 546/17; 514/278
See application file for complete search history.

(56) References Cited

U.S. PATENT DOCUMENTS

| | | | | |
|---|---|---|---|---|
| 5,106,998 A | 4/1992 | Tanaka et al. | ............... | 549/331 |
| 5,132,307 A | 7/1992 | Baumgarth et al. | .......... | 514/247 |
| 5,349,065 A | 9/1994 | Tanaka et al. | ................. | 546/15 |
| 5,354,863 A | 10/1994 | Dappen et al. | ................. | 546/35 |
| 5,356,915 A | 10/1994 | Almansa et al. | ............... | 514/357 |
| 5,387,587 A | 2/1995 | Häusler et al. | ............... | 514/254 |
| 5,403,846 A | 4/1995 | Baldwin et al. | ............... | 514/278 |
| 5,628,935 A | 5/1997 | Hughes et al. | ................. | 252/589 |
| 5,656,420 A | 8/1997 | Chien | ............................ | 435/1.2 |
| 5,705,102 A | 1/1998 | Hughes et al. | ............... | 252/375 |
| 5,786,378 A | 7/1998 | Hamilton et al. | ............... | 514/423 |
| 5,990,131 A | 11/1999 | Hamilton et al. | ............... | 514/330 |
| 6,022,895 A | 2/2000 | Zimmer et al. | | |
| 6,031,115 A | 2/2000 | Bell et al. | ..................... | 549/362 |
| 6,040,308 A | 3/2000 | Häusler et al. | ............... | 514/253 |
| 6,153,627 A | 11/2000 | Häusler et al. | ............... | 514/337 |
| 6,200,978 B1 | 3/2001 | Maw et al. | ............. | 514/254.05 |
| 6,218,424 B1 | 4/2001 | Hamilton et al. | ............... | 514/423 |
| 6,319,939 B1 | 11/2001 | Mabire et al. | ................. | 514/381 |
| 6,417,209 B2 | 7/2002 | Hamilton et al. | ............... | 514/365 |
| 6,436,959 B1 | 8/2002 | Carson et al. | ................. | 514/326 |
| 6,596,758 B1 | 7/2003 | Brunet et al. | ................. | 514/450 |
| 6,645,973 B1 | 11/2003 | Gibson | | |
| 7,226,933 B2 | 6/2007 | Brown et al. | | |
| 7,338,962 B2 * | 3/2008 | Dolle et al. | ................. | 514/278 |
| 2001/0056103 A1 | 12/2001 | Hamilton et al. | ............... | 514/327 |
| 2002/0115653 A1 | 8/2002 | Mabire et al. | ................. | 514/212 |
| 2002/0193420 A1 | 12/2002 | Hamilton et al. | ............... | 514/438 |
| 2003/0069241 A1 | 4/2003 | Mchardy et al. | ............... | 514/241 |
| 2004/0082612 A1 | 4/2004 | Baxter et al. | ................. | 514/317 |
| 2004/0106652 A1 | 6/2004 | Hamilton et al. | ............ | 514/355 |
| 2005/0159438 A1 | 7/2005 | Dolle et al. | ................. | 514/278 |
| 2006/0270695 A1 | 11/2006 | Dolle et al. | | |
| 2008/0102031 A1 | 5/2008 | Dolle et al. | | |
| 2008/0119452 A1 | 5/2008 | Dolle et al. | | |

FOREIGN PATENT DOCUMENTS

| | | |
|---|---|---|
| CN | 1390221 A1 | 1/2003 |
| EP | 0 420 266 A3 | 4/1991 |
| EP | 0 362 119 B1 | 7/1993 |
| EP | 0 600 147 A1 | 6/1994 |
| EP | 0 401 958 B1 | 1/1995 |
| EP | 0 376 524 B1 | 3/1995 |
| EP | 0 708 164 A3 | 4/1996 |
| EP | 0 582 338 B1 | 10/1999 |
| EP | 1 179 551 A1 | 2/2002 |
| EP | 0 864 559 B1 | 6/2002 |
| JP | 4-275288 A | 9/1992 |
| JP | 9-301973 | 11/1997 |
| WO | 93/17026 A1 | 9/1993 |
| WO | 93/19755 A1 | 10/1993 |
| WO | 94/17045 A1 | 8/1994 |
| WO | 95/04734 A1 | 2/1995 |
| WO | 95/31464 A1 | 11/1995 |
| WO | 96/22276 A1 | 7/1996 |
| WO | 97/10216 A1 | 3/1997 |
| WO | WO9828275 | 7/1998 |

(Continued)

OTHER PUBLICATIONS

Yang, Shuzang et al., "Structure-activity relationship of rubiscolins as δ opioid peptides," Peptides, 2003, 24, 503-508.

(Continued)

*Primary Examiner*—D. Margaret Seaman
*Assistant Examiner*—Nizal S Chandrakumar
(74) *Attorney, Agent, or Firm*—Feldman Gale, P.A.; David A. Cherry

(57) ABSTRACT

Spirocyclic heterocyclic derivatives, pharmaceutical compositions containing these compounds, and methods for their pharmaceutical use are disclosed. In certain embodiments, the spirocyclic heterocyclic derivatives are ligands of the δ-opioid receptor and may be useful, inter alia, for treating and/or preventing pain, anxiety, gastrointestinal disorders, and other δ-opioid receptor-mediated diseases, disorders, and/or conditions.

62 Claims, No Drawings

FOREIGN PATENT DOCUMENTS

| | | |
|---|---|---|
| WO | 99/04795 A1 | 2/1999 |
| WO | 99/29674 A1 | 6/1999 |
| WO | 00/39113 A1 | 7/2000 |
| WO | 01/36423 A1 | 5/2001 |
| WO | 01/46192 A1 | 6/2001 |
| WO | 01/83476 A1 | 11/2001 |
| WO | WO0185145 | 11/2001 |
| WO | 02/48122 A2 | 6/2002 |
| WO | 02/094782 A1 | 11/2002 |
| WO | 02/094783 A1 | 11/2002 |
| WO | 02/094784 A1 | 11/2002 |
| WO | 02/094785 A1 | 11/2002 |
| WO | 02/094786 A1 | 11/2002 |
| WO | 02/094794 A1 | 11/2002 |
| WO | 02/094810 A1 | 11/2002 |
| WO | 02/094811 A1 | 11/2002 |
| WO | 02/094812 A1 | 11/2002 |
| WO | 03/029215 A1 | 4/2003 |
| WO | 03/033486 A1 | 4/2003 |
| WO | 03/037342 A1 | 5/2003 |
| WO | 03/057223 A1 | 7/2003 |
| WO | 93/15062 A1 | 8/2003 |
| WO | 2004/026819 A2 | 4/2004 |
| WO | 2004/035541 A1 | 4/2004 |
| WO | 2004/035574 A2 | 4/2004 |
| WO | 2004/041784 A1 | 5/2004 |
| WO | 2004/041800 A1 | 5/2004 |
| WO | 2004/041801 A1 | 5/2004 |
| WO | 2004/041802 A1 | 5/2004 |
| WO | 2004/060321 A2 | 7/2004 |
| WO | 2004/062562 A2 | 7/2004 |
| WO | 2004/063157 A1 | 7/2004 |
| WO | 2004/063193 A1 | 7/2004 |
| WO | 2004/082612 A1 | 9/2004 |
| WO | WO2005019157 | 3/2005 |
| WO | 2005/033073 A2 | 4/2005 |

OTHER PUBLICATIONS

Ennaceur, A. et al., "A new one-trial test for neurobiological studies of memory in rats. 1: Behavioral data," *Behavioural Brain Research*, 1988, 31, 47-59.

Yang, Shuzhang, et al., "Effect on rubiscolin, a δ opioid peptide derived from Rubisco, on memory consolidation," *Peptides* (2003), 24, 325-328.

U.S. Appl. No. 60/507,864, filed Oct. 1, 2003, Roland Dolle.

Bhargava, H.N., et al., "Effect of nitric oxide synthase inhibition on tolerance to the analgesic action of D-Pen$^2$, D-Pen$^5$ enkephalin and morphine in the mouse," *Neuropeptides*, 1996, 30(3), 219-223.

Bilsky, E.J., et al., "SNC 80, A Selective, Nonpeptidic And Systemically Active Opioid *Delta* Agonist," *J. of Pharmacology and Experimental Therapeutics*, 1995, 273(1), 359-366.

Bilsky, E.J., et al., "Effects Of Naloxone And D-Phe-Cys-Tyr-D-Trp-Arg-Thr-Pen-Thr-NH$_2$ And The Protein Kinase Inhibitors H7 And H8 On Acute Morphine Dependence And Antinociceptive Tolerance In Mice," *J. of Pharmacol Exp. Ther.*, 1996, 277(1), 484-490.

Borlongan, C.V., et al., "Delta opioid peptide (D-ALA 2, D-LEU 5) enkephalin: linking hibernation and neuroprotection," *Frontiers in Bioscience*, Sep. 1, 2004, 9, 3392-3398.

DeHaven R.N., et al., "Characterization Of Opioid Receptors," *Current Protocols in Pharmacology*, 2000, John Wiley & Sons, 1.4.1-1.4.12.

Dondio, et al., "Central & Peripheral Nervous Systems: Non-Peptide Δ Opioid Agonists And Antagonists," *Exp. Opin. Ther. Patents*, 1997, 7(10), 1075-1098.

Dorland's Illustrated Medical Dictionary, 27$^{th}$ Ed., *W.B. Saunders co., Phila.*, 1988, p. 375.

Dourish, C.T., et al., "Enhancement Of Morphine Analgesia And Prevention Of Morphine Tolerance In The Rat By The Cholecystokinin Antagonist L-364, 718," *Eur. J. Pharmacol.*, 1988, 147, 469-472.

Fraser, M.O., "Urinary Incontinence: Neuropharmacological Approaches," *Annual Reports in Medicinal Chemistry*, 2003, Chapter 6, 51-60.

Galligan, J.J., et al., "Cerebral *Delta* Opioid Receptors Mediate Analgesia But Not The Intestinal Motility Effects Of Intracerebroventricularly Administered Opioids," *J. Pharm. Exp. Ther.*, 1984, 229(3), 641-648.

Jain, K.K., "A guide to drug evaluation for chronic pain," *Emerging Drugs*, 2000, 5(2), 241-257.

Livingston, E.H., et al., "Postoperative Ileus," *Digestive Diseases and Sciences*, 1990, 35(1), 121-132.

Lord, J.A.H., et al., "Endogenous opioid peptides: multiple agonists and receptors," *Nature*, 1977, 267, 495-499.

Mao, J., et al., "Oral Administration Of Dextromethorphan Prevents The Development Of Morphine Tolerance And Dependence In Rats," *Pain*, 1996, 67, 361-368.

Moreland, R.B., et al., "Emerging Pharmacologic Approaches For The Treatment Of Lower Urinary Tract Disorders," *J. Pharm. Exp. Ther.*, 2004, 308(3), 797-804.

Moulin, D.E., et al., "The Analgesic Efficacy Of Intrathecal D-Ala$^2$-D-Leu$^5$-Enkephalin in Cancer Patients with Chronic Pain," *Pain*, 1985, 23, 213-221.

Nichols, M.L., et al., "Enhancement of the antiallodynic and antinociceptive efficacy of spinal morphine by antisera to dynorphin A (1-13) or MK-801 in a nerve-ligation model of peripheral neuropathy," *Pain*, 1997, 69, 317-322.

Raynor, K., et al., "Pharmacological Characterization Of The Cloned K-, Δ-, And M- Opioid Receptors," *Molecular Pharmacology*, 1994, 45, 330-334.

Resnick, J., "Delayed gastric emptying and postoperative Ileus after nongastric abdominal surgery: Part I," *Am. J. of Gastroenterology*, 1997, 92(5), 751-762.

Resnick, J., "Delayed gastric emptying and postoperative Ileus after nongastric abdominal surgery: Part II," *Am. J. of Gastroenterology*, 1997, 92(6), 934-940.

Schultz, J.J. et al, "Ischemic Preconditioning and Morphine-Induced Cardioprotection Involve the delta-Opioid Receptor in the Intact Rat Heart", *J. Mol. Cell. Cardiol.*, 1997, 29, 2187-2195.

Schultz, J.J. et al., "Ischemic Preconditioning is Mediated by a Peripheral Opioid Receptor Mechanism in the Intact Rat Heart", *J. Mol. Cell. Cardiol.*, 1997, 29, 1355-1362.

Tsung-Ping Su, "Delta Opioid Peptide [*D*-Ala$^2$,*D*-Leu$^5$]Enkephalin Promotes Cell Survival," *J. of Biomedical Science*, 2000, 7, 195-199.

Watson, M.J. et al., "ARD-353 [4-((2R,5S)-4-(R)-(4-Diethylcarbamoylphenyl)(3-hydroxyphenyl)methyl)-2,5-dimethylpiperazin-1-ylmethyl)benzoic Acid], A Novel Nonpeptide δ Receptor Agonist, Reduces Myocardial Infarct Size without Central Effects ," *J. Pharm. Exp. Ther.*, 2006, 316(1), 423-430.

Xenopoulos, N.P. et al., "Morphine Mimics Ischemic Preconditioning in Human Myocardium during PTCA", *J. Am. Coll. Cardiol.*, 1998, 31(Suppl. A), 65A-66A, Abstract No. 810-3.

\* cited by examiner

SPIROCYCLIC HETEROCYCLIC DERIVATIVES AND METHODS OF THEIR USE

CROSS-REFERENCE TO RELATED APPLICATIONS

This application claims the benefit of U.S. Provisional Application Ser. No. 60/790,416, filed Apr. 6, 2006, the disclosure of which is incorporated herein by reference in its entirety.

FIELD OF THE INVENTION

The invention relates to spirocyclic heterocyclic derivatives (including derivatives of spiro(2H-1-benzopyran-2,4'-piperidines and spiro[1,2,3,4-tetrahydronaphthalene-2,4'-piperidines), pharmaceutical compositions containing these compounds, and methods for their pharmaceutical use. In certain embodiments, the spirocyclic heterocyclic derivatives are ligands of the δ-opioid receptor and are useful, inter alia, for treating pain, anxiety, gastrointestinal disorders, and other δ-opioid receptor-mediated conditions.

BACKGROUND OF THE INVENTION

There are at least three different opioid receptors (μ, δ, and κ) that are present in both central and peripheral nervous systems of many species, including humans. Lord, J. A. H., et al., *Nature*, 1977, 267, 495. Activation of the δ-opioid receptors induces analgesia in various animal models. Moulin, et al., *Pain*, 1985, 23, 213. Some work suggests that the analgesics working at δ-opioid receptors do not have the attendant side effects associated with μ and κ opioid receptor activation. Galligan, et al., *J. Pharm. Exp. Ther.*, 1985, 229, 641. The δ-opioid receptor has also been identified as having a role in circulatory systems. Ligands for the δ-receptor have also been shown to possess immunomodulatory activities. Dondio, et al., *Exp. Opin. Ther. Patents*, 1997, 10, 1075. Further, selective δ-opioid receptor agonists have been shown to promote organ and cell survival. Su, T-P, *Journal of Biomedical Science*, 2000, 9(3), 195-199. The δ-opioid receptor was recently recognized to trigger and mimic ischemic preconditioning (Schultz, et al, "Ischemic Preconditioning and Morphine-Induced Cardioprotection Involve the delta-Opioid Receptor in the Intact Rat Heart", *J. Mol. Cell. Cardiol.*, 29: 2187-2195, 1997; Schultz, et al., "Ischemic Preconditioning is Mediated by a Peripheral Opioid Receptor Mechanism in the Intact Rat Heart", *J. Mol. Cell. Cardiol.,* 29: 1355-1362, 1997). An opioid role in human preconditioning was further demonstrated by Xenopoulos, et al., "Morphine Mimics Ischemic Preconditioning in Human Myocardium during PTCA", *J. Am. Coll. Cardiol.*, 65: 65A 1998 with the application of intracoronary morphine as a mimic for preconditioning. Other reported developments include the use of δ-opioid receptor agonists to reduce myocardial infarct size (Watson, et al., *J. Pharm. Exp. Ther.* 316: 423-430 (2006)) and to reduce ischemic damage or provide cardioprotection for example, from myocardial infarction (WO 2004/060321 A2; WO 99/04795). Ligands for the δ-opioid receptor may therefore find potential use as analgesics, antihypertensive agents, immunomodulatory agents, and/or agents for the treatment of cardiac disorders.

Numerous selective δ-opioid ligands are peptidic in nature and thus are unsuitable for administration by systemic routes. Several non-peptidic δ-opioid receptor ligands have been developed. See, for example, E. J. Bilsky, et al., *Journal of Pharmacology and Experimental Therapeutics*, 1995, 273 (1), 359-366; WO 93/15062, WO 95/04734, WO 95/31464, WO 96/22276, WO 97/10216, WO 01/46192, WO 02/094794, WO 02/094810, WO 02/094811, WO 02/094812, WO 02/48122, WO 03/029215, WO 03/033486, JP-4275288, EP-A-0,864,559, U.S. Pat. Nos. 5,354,863, 6,200,978, 6,436, 959, and US 2003/0069241.

While there are a large number of non-peptidic δ-opioid receptor modulators, there is still an unfulfilled need for compounds with selective δ-opioid receptor activity that may be used in methods to provide beneficial pharmaceutical characteristics while minimizing undesirable side effects. The present invention is directed to these, as well as other important ends.

SUMMARY OF THE INVENTION

Accordingly, the present invention is directed, in part, to novel spiro(2H-1-benzopyran-2,4'-piperidine and spiro[1,2,3,4-tetrahydronaphthalene-2,4'-piperidine compounds. In preferred form, the novel compounds of the invention have the following formula I:

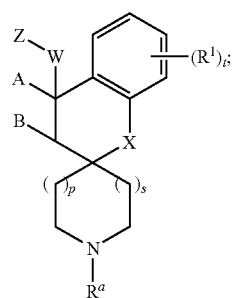

wherein:
W is alkylene;
Z is alkoxy, —C(=O)—R$^2$, —NR$^3$—C(=O)—R$^4$, or —NR$^3$S(=O)$_m$alkyl;
each R$^1$ is independently carboxy, hydroxy, alkoxy, halo, aminocarbonyl, N-alkylaminocarbonyl, or N,N-dialkylaminocarbonyl;
R$^2$ is —NR$^5$R$^6$ or alkoxy;
R$^3$ and R$^a$ are each independently H or alkyl;
R$^4$ is alkyl or —NR$^5$R$^6$;
R$^5$ and R$^6$ are each independently H or alkyl, or R$^5$ and R$^6$ taken together with the nitrogen atom to which they are connected form a 3- to 8-membered heterocycloalkyl ring in which 1 or 2 of the heterocycloalkyl ring carbon atoms independently may each be optionally replaced by —O—, —S—, —N(R$^7$)—, —N(R$^8$)—C(=O)—, or —C(=O)—N(R$^9$)—;
R$^7$, R$^8$, and R$^9$ are each independently H or alkyl;
X is —CH$_2$—, —S(=O)$_m$— or —O—;
A and B are each H, or taken together with the carbon atoms through which they are connected form a double bond;
each m is independently 0, 1, or 2;
p and t are each independently 0, 1, or 2; and
s is 1 or 2; provided that the sum of p+s is 1, 2, or 3;
or a pharmaceutically acceptable salt thereof.

In other embodiments, the present invention is directed to pharmaceutical compositions, comprising a pharmaceutically acceptable carrier and a compound of formula I.

In certain other embodiments, the present invention is directed to methods of binding opioid receptors in a patient in need thereof, comprising the step of administering to said patient an effective amount of a compound of formula I.

These and other aspects of the invention will become more apparent from the following detailed description.

DETAILED DESCRIPTION OF ILLUSTRATIVE EMBODIMENTS

The invention relates to spirocyclic heterocyclic derivatives, pharmaceutical compositions containing these compounds, and methods for their pharmaceutical use. In certain embodiments, the spirocyclic heterocyclic derivatives are ligands of the δ-opioid receptor and may be useful, inter alia, in methods for treating diseases, disorders, and/or conditions that may be mediated or modulated by the δ-opioid receptor including, for example, pain, gastrointestinal disorders, urogenital tract disorders including incontinence and overactive bladder, immunomodulatory disorders, inflammatory disorders, respiratory function disorders, anxiety, mood disorders, stress-related disorders, attention deficit hyperactivity disorders, sympathetic nervous system disorders, depression, tussis, motor disorders, traumatic injuries, especially to the central nervous system, stroke, cardiac arrhythmias, glaucoma, sexual dysfunctions, shock, brain edema, cerebral ischemia, cerebral deficits subsequent to cardiac bypass surgery and grafting, systemic lupus erythematosus, Hodgkin's disease, Sjogren's disease, epilepsy, rejections in organ transplants and skin grafts, and substance addiction. In certain other embodiments, the spirocyclic heterocyclic derivatives are ligands of the δ-opioid receptor and may be useful in, inter alia, methods for improving organ and cell survival, methods for providing cardioprotection, methods for reducing the need for anesthesia, methods for producing and/or maintaining an anesthetic state, and methods of detecting, imaging, or monitoring degeneration or dysfunction of opioid receptors in a patient.

As employed above and throughout the disclosure, the following terms, unless otherwise indicated, shall be understood to have the following meanings.

As used herein, "alkyl" refers to an optionally substituted, saturated straight, or branched, hydrocarbon having from about 1 to about 10 carbon atoms (and all combinations and subcombinations of ranges and specific numbers of carbon atoms therein), preferably with from about 1 to about 6, more preferably 1 to about 4, yet more preferably about 1 to about 3, with about 2 to about 3 carbon atoms being most preferred. Alkyl groups include, but are not limited to, methyl, ethyl, n-propyl, isopropyl, n-butyl, isobutyl, t-butyl, n-pentyl, isopentyl, neopentyl, n-hexyl, isohexyl, 3-methylpentyl, 2,2-dimethylbutyl, and 2,3-dimethylbutyl.

As used herein, "alkenyl" refers to an optionally substituted alkyl group having from about 2 to about 10 carbon atoms and one or more double bonds (and all combinations and subcombinations of ranges and specific numbers of carbon atoms therein), wherein alkyl is as previously defined.

As used herein, "alkylene" refers to an optionally substituted bivalent alkyl radical having the general formula —(CH$_2$)$_n$—, where n is 1 to 10, preferably 1 to 6, with 1 to 4 being most preferred. Non-limiting examples include methylene, dimethylene, trimethylene, pentamethylene, and hexamethylene.

As used herein, "alkynyl" refers to an optionally substituted alkyl group having from about 2 to about 10 carbon atoms and one or more triple bonds (and all combinations and subcombinations of ranges and specific numbers of carbon atoms therein), wherein alkyl is as previously defined.

As used herein, "alkoxy" refers to an optionally substituted alkyl-O— group wherein alkyl is as previously defined. In some preferred embodiments, the alkyl moieties of the alkoxy groups have from about 1 to about 4, more preferably from about 1 to about 3, carbon atoms. Exemplary alkoxy groups include methoxy, ethoxy, n-propoxy, i-propoxy, n-butoxy, and heptoxy.

As used herein, "aryl" refers to an optionally substituted, mono-, di-, tri-, or other multicyclic aromatic ring system having from about 5 to about 50 carbon atoms (and all combinations and subcombinations of ranges and specific numbers of carbon atoms therein), with from about 6 to about 10 carbons being preferred. Non-limiting examples include, for example, phenyl, naphthyl, anthracenyl, and phenanthrenyl.

As used herein, "aralkyl" refers to an optionally substituted moiety composed of an alkyl radical bearing an aryl substituent, wherein the aralkyl moiety has from about 7 to about 50 carbon atoms (and all combinations and subcombinations of ranges and specific numbers of carbon atoms therein), with from about 7 to about 11 carbon atoms being preferred. Non-limiting examples include, for example, benzyl, diphenylmethyl, triphenylmethyl, phenylethyl, and diphenylethyl.

As used herein, "heteroaryl" refers to an optionally substituted aryl ring system wherein in at least one of the rings, one or more of the carbon atom ring members is independently replaced by a heteroatom group selected from the group consisting of S, O, N, and NH, wherein aryl is as previously defined. Heteroaryl groups having a total of from about 5 to about 14 carbon atom ring members and heteroatom ring members (and all combinations and subcombinations of ranges and specific numbers of carbon and heteroatom ring members) are preferred. Exemplary heteroaryl groups include, but are not limited to, pyrryl, furyl, pyridyl, pyridine-N-oxide, 1,2,4-thiadiazolyl, pyrimidyl, thienyl, isothiazolyl, imidazolyl, tetrazolyl, pyrazinyl, pyrimidyl, quinolyl, isoquinolyl, thiophenyl, benzothienyl, isobenzofuryl, pyrazolyl, indolyl, purinyl, carbazolyl, benzimidazolyl, and isoxazolyl. Heteroaryl groups may be attached via a carbon or a heteroatom to the rest of the molecule.

As used herein, "cycloalkyl" refers to an optionally substituted, mono-, di-, tri-, or other multicyclic alicyclic ring system having from about 3 to about 20 carbon atoms (and all combinations and subcombinations of ranges and specific numbers of carbon atoms therein). In some preferred embodiments, the cycloalkyl groups have from about 3 to about 8 carbon atoms. Multi-ring structures may be bridged or fused ring structures, wherein the additional groups fused or bridged to the cycloalkyl ring may include optionally substituted cycloalkyl, aryl, heterocycloalkyl, or heteroaryl rings. Exemplary cycloalkyl groups include, but are not limited to, cyclopropyl, cyclobutyl, cyclopentyl, cyclohexyl, cyclooctyl, adamantyl, 2-[4-isopropyl-1-methyl-7-oxa-bicyclo[2.2.1]heptanyl], and 2-[1,2,3,4-tetrahydro-naphthalenyl].

As used herein, "alkylcycloalkyl" refers to an optionally substituted ring system comprising a cycloalkyl group having one or more alkyl substituents, wherein cycloalkyl and alkyl are each as previously defined. Exemplary alkylcycloalkyl groups include, for example, 2-methylcyclohexyl, 3,3-dimethylcyclopentyl, trans-2,3-dimethylcyclooctyl, and 4-methyldecahydronaphthalenyl.

As used herein, "heteroaralkyl" refers to an optionally substituted ring system composed of a heteroaryl substituted alkyl radical where heteroaryl and alkyl are as previously defined. Non-limiting examples include, for example, 2-(1H- pyrrol-3-yl)ethyl, 3-pyridylmethyl, 5-(2H-tetrazolyl)methyl, and 3-(pyrimidin-2-yl)-2-methylcyclopentanyl.

As used herein, the term "heterocycloalkyl" and "heterocyclic ring" each refers to an optionally substituted ring system composed of a cycloalkyl radical wherein in at least one of the rings, one or more of the carbon atom ring members is independently replaced by a heteroatom group selected from the group consisting of O, S, N, and NH, wherein cycloalkyl is as previously defined. Heterocycloalkyl ring systems having a total of from about 3 to about 14 carbon atom ring members and heteroatom ring members (and all combinations and subcombinations of ranges and specific numbers of carbon and heteroatom ring members) are preferred. In other preferred embodiments, the heterocyclic groups may be fused to one or more aryl rings. In certain preferred embodiments, heterocycloalkyl moieties are attached via a ring carbon atom to the rest of the molecule. Exemplary heterocycloalkyl groups include, but are not limited to, aziridinyl, azepanyl, tetrahydrofuranyl, hexahydropyrimidinyl, tetrahydrothienyl, piperidinyl, pyrrolidinyl, isoxazolidinyl, isothiazolidinyl, pyrazolidinyl, oxazolidinyl, thiazolidinyl, piperazinyl, 2-oxo-morpholinyl, morpholinyl, 2-oxo-piperidinyl, piperadinyl, decahydroquinolyl, octahydrochromenyl, octahydrocyclopenta[c]pyranyl, 1,2,3,4,-tetrahydroquinolyl, 1,2,3,4-tetrahydroquinazolinyl, octahydro-[2]pyridinyl, decahydrocycloocta[c]furanyl, 1,2,3,4-tetrahydroisoquinolyl, 2-oxoimidazolidinyl, and imidazolidinyl. In some embodiments, two moieties attached to a heteroatom may be taken together to form a heterocycloalkyl ring, such as when $R^2$ and $R^3$, taken together with the nitrogen atom to which they are attached, form a heterocycloalkyl ring. In certain of these embodiments, 1 or 2 of the heterocycloalkyl ring carbon atoms may be replaced by other moieties which contain either one (—O—, —S—, —N(R')—) or two (—N(R")—C(=O)—, or —C(=O)—N(R")—) ring replacement atoms, wherein each R' and R" may independently be, for example, H or alkyl. When a moiety containing one ring replacement atom replaces a ring carbon atom, the resultant ring, after replacement of a ring atom by the moiety, will contain the same number of ring atoms as the ring before ring atom replacement. When a moiety containing two ring replacement atoms replaces a ring carbon atom, the resultant ring after replacement will contain one more ring atom than the ring prior to replacement by the moiety. For example, when a piperidine ring has one of its ring carbon atoms replaced by —N(R")—C(=O)—, the resultant ring is a 7-membered ring containing 2 ring nitrogen atoms and the carbon of a carbonyl group in addition to 4 other carbon ring atoms ($CH_2$ groups) from the original piperidine ring.

As used herein, the term "spiroalkyl" refers to an optionally substituted alkylene diradical, both ends of which are bonded to the same carbon atom of the parent group to form a spirocyclic group. The spirocyclic group, as herein defined, has 3 to 20 ring atoms, preferably with 3 to 10 ring atoms. Exemplary spiroalkyl groups taken together with its parent group include, but are not limited to, 1-(1-methyl-cyclopropyl)-propan-2-one, 2-(1-phenoxy-cyclopropyl)-ethylamine, and 1-methyl-spiro[4.7]dodecane.

As used herein, "halo" and "halogen" each refers to a fluoro, chloro, bromo, or iodo moiety with fluoro, chloro, or bromo moieties being preferred, and fluoro being more preferred.

Typically, substituted chemical moieties include one or more substituents that replace hydrogen. Exemplary substituents include, for example, halo (e.g., F, Cl, Br, I), alkyl, cycloalkyl, alkylcycloalkyl, alkenyl, alkynyl, aralkyl, aryl, heteroaryl, heteroaralkyl, spiroalkyl, heterocycloalkyl, hydroxyl (—OH), oxo (=O), nitro (—$NO_2$), cyano (—CN), amino (—$NH_2$), —N-substituted amino (—NHR"), —N,N-disubstituted amino (—N(R")R"), carboxy (—COOH), —O—C(=O)R", —C(=O)R", —OR", —C(=O)OR", —NHC(=O)R", aminocarbonyl (—C(=O)$NH_2$), —N-substituted aminocarbonyl (—C(=O)NHR"), —N,N-disubstituted aminocarbonyl (—C(=O)N(R")R"), thiol, thiolato (—SR"), sulfonic acid (—$SO_3H$), phosphonic acid (—$PO_3H$), —P(=O)(OR")OR", S(=O)R", —S(=O)$_2$R", —S(=O)$_2NH_2$, —S(=O)$_2$NHR", —S(=O)$_2$NR"R", —NHS(=O)$_2$R", —NR"S(=O)$_2$R", —$CF_3$, —$CF_2CF_3$, —NHC(=O)NHR", —NHC(=O)NR"R", —NR"C(=O)NHR", —NR"C(=O)NR"R", —NR"C(=O)R" and the like. In relation to the aforementioned substituents, each moiety R" can be, independently, any of H, alkyl, cycloalkyl, alkenyl, aryl, aralkyl, heteroaryl, or heterocycloalkyl, or when two R" groups are attached to the same nitrogen atom within a substituent, as herein above defined, R" and R" can be taken together with the nitrogen atom to which they are attached to form a 3- to 8-membered heterocycloalkyl ring, wherein one or two of the heterocycloalkyl ring carbon atoms independently may be optionally replaced by —O—, —S—, —SO, —$SO_2$—, —NH—, —N(alkyl)-, —N(acyl)-, —N(aryl)-, or —N(aroyl)- groups, for example.

As used herein, "ligand" or "modulator" refers to a compound that binds to a receptor to form a complex, and includes, agonists, partial agonists, antagonists and inverse agonists.

As used herein, the term "antagonist" refers to a compound that binds to a receptor to form a complex that preferably does not elicit any response, in the same manner as an unoccupied receptor, and does not alter the equilibrium between inactive and active receptor.

As used herein, "agonist" refers to a ligand that produces a conformational change in the receptor and alters the equilibrium of the receptor's active and inactive states, which in turn induces a series of events, resulting in a measurable biological response. Agonists include, for example, conventional agonists, which exhibit positive receptor activity, and inverse agonists, which exhibit a negative intrinsic activity.

As used herein, "side effect" refers to a consequence other than the one(s) for which an agent or measure is used, as the adverse effects produced by a drug, especially on a tissue or organ system other then the one sought to be benefited by its administration. In the case, for example, of opioids, the term "side effect" may refer to such conditions as, for example, constipation, nausea, vomiting, dyspnea and pruritus.

"Effective amount" refers to an amount of a compound as described herein that may be therapeutically effective to inhibit, treat the symptoms of particular disease, disorder, condition, or side effect. Such diseases, disorders, conditions, and side effects include, but are not limited to, those pathological conditions associated with the binding of δ-opioid receptor (for example, in connection with the treatment of pain), wherein the treatment comprises, for example, agonizing the activity thereof by contacting cells, tissues or receptors with compounds of the present invention. Thus, for example, the term "effective amount," when used in connection with compounds of the invention, opioids, or opioid replacements, for example, for the treatment of pain, refers to the treatment of the painful condition. The term "effective amount," when used in connection with compounds active against gastrointestinal dysfunction, refers to the treatment of symptoms, diseases, disorders, and conditions typically associated with gastrointestinal dysfunction. The term "effective amount," when used in connection with compounds useful in the treatment of urogenital tract disorders, refers to the treatment of symptoms, diseases, disorders, and conditions typically associated with urogenital tract disorders and other related conditions. The term "effective amount," when used in connection with compounds useful in the treatment of immunomodulatory disorders, refers to the treatment of symptoms, diseases, disorders, and conditions typically associated with immunomodulatory disorders and other related conditions. The term "effective amount," when used in connection with compounds useful in the treatment of inflammatory disorders, refers to the treatment of symptoms, diseases, disorders, and conditions typically associated with inflammatory disorders and other related conditions. The term "effective amount," when used in connection with compounds useful in the treatment of respiratory function disorders, refers to the treatment of symptoms, diseases, disorders, and conditions typically associated with respiratory function disorders and other related conditions. The term "effective amount," when used in connection with compounds useful in the treatment of anxiety, mood disorders, stress-related disorders, and attention deficit hyperactivity disorder, refers to the treatment of symptoms, diseases, disorders, and conditions typically associated with anxiety, mood disorders, stress-related disorders, attention deficit hyperactivity disorder and other related conditions. The term "effective amount," when used in connection with compounds useful in the treatment of sympathetic nervous system disorders, refers to the treatment of symptoms, diseases, disorders, and conditions typically associated with sympathetic nervous system disorders and other related conditions. The term "effective amount," when used in connection with compounds useful in the treatment of tussis, refers to the treatment of symptoms, diseases, disorders, and conditions typically associated with tussis and other related conditions. The term "effective amount," when used in connection with compounds useful in the treatment of motor disorders, refers to the treatment of symptoms, diseases, disorders, and conditions typically associated with motor disorders and other related conditions. The term "effective amount," when used in connection with compounds useful in the treatment of traumatic injuries of the central nervous system, refers to the treatment of symptoms, diseases, disorders, and conditions typically associated with the central nervous system and other related conditions. The term "effective amount," when used in connection with compounds useful in the treatment of stroke, cardiac arrhythmia or glaucoma, refers to the treatment of symptoms, diseases, disorders, and conditions typically associated with stroke, cardiac arrhythmia, glaucoma and other related conditions. The term "effective amount," when used in connection with compounds useful in the treatment of sexual dysfunction, refers to the treatment of symptoms, diseases, disorders, and conditions typically associated with sexual dysfunction and other related conditions. The term "effective amount," when used in connection with compounds useful in improving organ and cell survival, refers to refers to the maintenance and/or improvement of a minimally-acceptable level of organ or cell survival, including organ preservation. The term "effective amount," when used in connection with compounds useful for providing cardioprotection, including after myocardial infarction, refers to the minimum level of compound necessary to provide cardioprotection. The term "effective amount," when used in connection with compounds useful in the treatment of shock, brain edema, cerebral ischemia, cerebral deficits subsequent to cardiac bypass surgery and grafting, systemic lupus erythematosus, Hodgkin's disease, Sjogren's disease, epilepsy, and rejection in organ transplants and skin grafts, refers to the treatment of symptoms, diseases, disorders, and conditions typically associated with shock, brain edema, cerebral ischemia, cerebral deficits subsequent to cardiac bypass surgery and grafting, systemic lupus erythematosus, Hodgkin's disease, Sjogren's disease, epilepsy, and rejection in organ transplants and skin grafts and other related conditions. The term "effective amount," when used in connection with compounds useful in the treatment of substance addiction, refers to the treatment of symptoms, diseases, disorders, and conditions typically associated with substance addiction and other related conditions. The term "effective amount," when used in connection with compounds useful in reducing the need for anesthesia or producing and/or maintaining an anesthetic state, refers to the production and/or maintenance of a minimally-acceptable anesthetic state.

As used herein, "pharmaceutically acceptable" refers to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio.

"In combination with," "combination therapy," and "combination products" refer, in certain embodiments, to the concurrent administration to a patient of a compound of the invention including, for example, a compound of formula I, II, III, IV, or V, and one or more additional agents including, for example, an opioid, an anesthetic agent (such as for example, an inhaled anesthetic, hypnotic, anxiolytic, neuromuscular blocker and opioid), an anti-Parkinson's agent (for example, in the case of treating a motor disorder, particularly Parkinson's disease), an antidepressant (for example, in the case of treating a mood disorder, particularly depression), an agent for the treatment of incontinence (for example, in the case of treating a urogenital tract disorder), an agent for the treatment of pain, including neuralgias or neuropathic pain, cardioprotective agents, and/or other optional ingredients (including, for example, antibiotics, antivirals, antifungals, anti-inflammatories, anesthetics and mixtures thereof). When administered in combination, each component may be administered at the same time or sequentially in any order at different points in time. Thus, each component may be administered separately but sufficiently closely in time so as to provide the desired therapeutic effect.

As used herein, "dosage unit" refers to physically discrete units suited as unitary dosages for the particular individual to be treated. Each unit may contain a predetermined quantity of active compound(s) calculated to produce the desired therapeutic effect(s) in association with the required pharmaceutical carrier. The specification for the dosage unit forms of the invention may be dictated by (a) the unique characteristics of the active compound(s) and the particular therapeutic effect(s) to be achieved, and (b) the limitations inherent in the art of compounding such active compound(s).

As used herein, "hydrate" refers to a compound of the present invention which is associated with water in the molecular form, i.e., in which the H—OH bond is not split, and may be represented, for example, by the formula $R.H_2O$, where R is a compound of the invention. A given compound may form more than one hydrate including, for example, monohydrates ($R.H_2O$) or polyhydrates ($R.nH_2O$ wherein n is an integer>1) including, for example, dihydrates ($R.2H_2O$), trihydrates ($R.3H_2O$), and the like, or hemihydrates, such as, for example, $R.n_{1/2}H_2O$, $R.n_{1/3}H_2O$, $R.n_{1/4}H_2O$ and the like wherein n is an integer.

As used herein, "solvate" refers to a compound of the present invention which is associated with solvent in the molecular form, i.e., in which the solvent is coordinatively bound, and may be represented, for example, by the formula R.(solvent), where R is a compound of the invention. A given compound may form more than one solvate including, for example, monosolvates (R.(solvent)) or polysolvates (R.n (solvent)) wherein n is an integer>1) including, for example, disolvates (R.2(solvent)), trisolvates (R.3(solvent)), and the like, or hemisolvates, such as, for example, $R.n_{/2}$(solvent), $R.n_{/3}$(solvent), $R.n_{/4}$(solvent) and the like wherein n is an integer. Solvents herein include mixed solvents, for example, methanol/water, and as such, the solvates may incorporate one or more solvents within the solvate.

As used herein, "acid hydrate" refers to a complex that may be formed through association of a compound having one or more base moieties with at least one compound having one or more acid moieties or through association of a compound having one or more acid moieties with at least one compound having one or more base moieties, said complex being further associated with water molecules so as to form a hydrate, wherein said hydrate is as previously defined and R represents the complex herein described above.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine.

Compounds described herein throughout, can be used or prepared in alternate forms. For example, many amino-containing compounds can be used or prepared as an acid addition salt. Often such salts improve isolation and handling properties of the compound. For example, depending on the reagents, reaction conditions and the like, compounds as described herein can be used or prepared, for example, as their hydrochloride or tosylate salts. Isomorphic crystalline forms, all chiral and racemic forms, N-oxide, hydrates, solvates, and acid salt hydrates, are also contemplated to be within the scope of the present invention.

Certain acidic or basic compounds of the present invention may exist as zwitterions. All forms of the compounds, including free acid, free base and zwitterions, are contemplated to be within the scope of the present invention. It is well known in the art that compounds containing both amino and carboxy groups often exist in equilibrium with their zwitterionic forms. Thus, any of the compounds described herein throughout that contain, for example, both amino and carboxy groups, also include reference to their corresponding zwitterions.

As used herein, "pain" refers to the perception or condition of unpleasant sensory or emotional experience, associated with actual or potential tissue damage or described in terms of such damage. "Pain" includes, but is not limited to, two broad categories of pain: acute and chronic pain (Buschmann, H.; Christoph, T; Friderichs, E.; Maul, C.; Sundermann, B; eds.; *Analgesics*, Wiley-VCH, Verlag GMbH & Co. KgaA, Weinheim; 2002; Jain, K. K. "A Guide to Drug Evaluation for Chronic Pain"; *Emerging Drugs*, 5(2), 241-257 (2000)). Non-limiting examples of pain include, for example, nociceptive pain, inflammatory pain, visceral pain, somatic pain, neuralgias, neuropathic pain, AIDS pain, cancer pain, phantom pain, and psychogenic pain, and pain resulting from hyperalgesia, pain caused by rheumatoid arthritis, migraine, allodynia and the like.

As used herein, "gastrointestinal dysfunction" refers collectively to maladies of the stomach, small and large intestine. Non-limiting examples of gastrointestinal dysfunction include, for example, diarrhea, nausea, emesis, post-operative emesis, opioid-induced emesis, irritable bowel syndrome, opioid-bowel dysfunction, inflammatory bowel disease, colitis, increased gastric motility, increased gastric emptying, stimulation of small intestinal propulsion, stimulation of large intestinal propulsion, decreased amplitude of non-propulsive segmental contractions, disorders associated with sphincter of Oddi, disorders associated with anal sphincter tone, impaired reflex relaxation with rectal distention, disorders associated with gastric, biliary, pancreatic or intestinal secretions, changes to the absorption of water from bowel contents, gastro-esophageal reflux, gastroparesis, cramping, bloating, distension, abdominal or epigastric pain and discomfort, non-ulcerogenic dyspepsia, gastritis, or changes to the absorption of orally administered medications or nutritive substances.

As used herein, "urogenital tract disorders" refers collectively to maladies of the urinary and genital apparati. Non-limiting examples of urogenital tract disorders include incontinence (i.e., involuntary loss of urine) such as stress urinary incontinence, urge urinary incontinence and benign prostatic hyperplasia, overactive bladder disorder, urinary retention, renal colic, glomerulonephritis, and interstitial cystitis.

As used herein, "overactive bladder disorder" refers to a condition with symptoms of urgency with or without incontinence, and is typically associated with increased urinary frequency and nocturia. Overactive bladder disorders are typically associated with urodynamic finding of involuntary bladder contractions, generally referred to as bladder instability.

As used herein, "immunomodulatory disorders" refers collectively to maladies characterized by a compromised or over-stimulated immune system. Non-limiting examples of immunomodulatory disorders include autoimmune diseases (such as arthritis, autoimmune disorders associated with skin grafts, autoimmune disorders associated with organ transplants, and autoimmune disorders associated with surgery), collagen diseases, allergies, side effects associated with the administration of an anti-tumor agent, side effects associated with the administration of an antiviral agent, multiple sclerosis and Guillain-Barre syndrome.

As used herein, "inflammatory disorders" refers collectively to maladies characterized by cellular events in injured tissues. Non-limiting examples of inflammatory disorders include arthritis, psoriasis, asthma, and inflammatory bowel disease.

As used herein, "respiratory function disorders" refers to conditions in which breathing and/or airflow into the lung is compromised. Non-limiting examples of respiratory function disorders include asthma, apnea, tussis, chronic obstruction pulmonary disease, and lung edema.

As used herein, "lung edema" refers to the presence of abnormally large amounts of fluid in the intercellular tissue spaces of the lungs.

As used herein, "anxiety" refers to the unpleasant emotional state consisting of psychophysiological responses to anticipation of real, unreal or imagined danger, ostensibly resulting from unrecognized intrapsychic conflict.

As used herein, "mood disorders" refers to disorders that have a disturbance in mood as their predominant feature, including depression, bipolar manic-depression, borderline personality disorder, and seasonal affective disorder.

As used herein, "depression" refers to a mental state of depressed mood characterized by feelings of sadness, despair and discouragement, including the blues, dysthymia, and major depression.

As used herein, "stress-related disorders" refer collectively to maladies characterized by a state of hyper- or hypoarousal with hyper- and hypovigilance. Non-limiting examples of stress-related disorders include post-traumatic stress disorder, panic disorder, generalized anxiety disorder, social phobia, and obsessive-compulsive disorder.

As used herein, "attention deficit hyperactivity disorder" refers to a condition characterized by an inability to control behavior due to difficulty in processing neural stimuli.

As used herein, "sympathetic nervous system disorders" refer collectively to maladies characterized by disturbances of the autonomic nervous system. Non-limiting examples of sympathetic nervous system disorders include hypertension, and the like.

As used herein, "tussis" refers to a coughing condition, and "antitussive" agents refer to those materials that modulate the coughing response.

As used herein, "motor disorders" refers to involuntary manifestations of hyper or hypo muscle activity and coordination. Non-limiting examples of motor disorders include tremors, Parkinson's disease, Tourette's syndrome, parasomnias (sleep disorders) including restless leg syndrome, postoperative shivering and dyskinesia.

As used herein, "traumatic injury of the central nervous system" refers to a physical wound or injury to the spinal cord or brain.

As used herein, "stroke" refers to a condition due to the lack of oxygen to the brain.

As used herein, "cardiac arrhythmia" refers to a condition characterized by a disturbance in the electrical activity of the heart that manifests as an abnormality in heart rate or heart rhythm. Patients with a cardiac arrhythmia may experience a wide variety of symptoms ranging from palpitations to fainting.

As used herein, "glaucoma" refers collectively to eye diseases characterized by an increase in intraocular pressure that causes pathological changes in the optic disk and typical defects in the field of vision.

As used herein, "sexual dysfunction" refers collectively to disturbances, impairments or abnormalities of the functioning of the male or female sexual organs, including, but not limited to premature ejaculation and erectile dysfunction.

As used herein, "cardioprotection" refers to conditions or agents, including, for example, ischemic preconditioning, that reduce or combat ischemic damage, or protect or restore the heart from dysfunction, heart failure and/or reperfusion injury.

As used herein, "ischemic preconditioning" refers to a physiological method of reducing injury to the myocardium after short-term ischemia and reperfusion. Repeated cycling of short episodes of ischemia induces changes in the myocardial cell signaling systems that appear to condition the myocytes to be resistant to ischemic and reperfusion damage. Patients undergoing repeated balloon angioplasty have been shown to experience significant protection through adaptation of the myocardium to mild ischemic periods.

As used herein, "myocardial infarction" refers to irreversible injury to heart muscle caused by a local lack of oxygen.

As used herein, "addiction" refers to a pattern of compulsive substance abuse (alcohol, nicotine, or drug) characterized by a continued craving for the substance and, in some cases, the need to use the substance for effects other than its prescribed or legal use.

As used herein, "anesthetic state" refers to the state of the loss of feeling or sensation, including not only the loss of tactile sensibility or of any of the other senses, but also to the loss of sensation of pain, as it is induced to permit performance of surgery or other painful procedures, and specifically including amnesia, analgesia, muscle relaxation and sedation.

As used herein, "improving organ and cell survival" refers to the maintenance and/or improvement of a minimally-acceptable level of organ or cell survival.

As used herein, "patient" refers to animals, including mammals, preferably humans.

As used herein, "prodrug" refers to compounds specifically designed to maximize the amount of active species that reaches the desired site of reaction, which are of themselves typically inactive or minimally active for the activity desired, but through biotransformation are converted into biologically active metabolites.

As used herein, the term "stereoisomers" refers to compounds that have identical chemical constitution, but differ as regards the arrangement of the atoms or groups in space.

As used herein, "N-oxide" refers to compounds wherein the basic nitrogen atom of either a heteroaryl ring or tertiary amine is oxidized to give a quaternary nitrogen bearing a positive formal charge and an attached oxygen atom bearing a negative formal charge.

The terms "treatment" and "treating" as used herein include preventative (e.g., prophylactic), curative and/or palliative treatment.

When any variable occurs more than one time in any constituent or in any formula, its definition in each occurrence is independent of its definition at every other occurrence. Combinations of substituents and/or variables are permissible only if such combinations result in stable compounds.

It is believed the chemical formulas and names used herein correctly and accurately reflect the underlying chemical compounds. However, the nature and value of the present invention does not depend upon the theoretical correctness of these formulae, in whole or in part. Thus it is understood that the formulas used herein, as well as the chemical names attributed to the correspondingly indicated compounds, are not intended to limit the invention in any way, including restricting it to any specific tautomeric form or to any specific optical or geometric isomer, except where such stereochemistry is clearly defined.

In certain preferred embodiments, the compounds, pharmaceutical compositions and methods of the present invention may involve a peripheral δ-opioid modulator compound. The term "peripheral" designates that the compound acts primarily on physiological systems and components external to the central nervous system. In preferred form, the peripheral δ-opioid modulator compounds employed in the methods of the present invention exhibit high levels of activity with respect to peripheral tissue, such as, gastrointestinal tissue, while exhibiting reduced, and preferably substantially no, CNS activity. The phrase "substantially no CNS activity," as used herein, means that less than about 50% of the pharmacological activity of the compounds employed in the present methods is exhibited in the CNS, preferably less than about 25%, more preferably less than about 10%, even more preferably less than about 5% and most preferably 0% of the pharmacological activity of the compounds employed in the present methods is exhibited in the CNS.

Furthermore, it is preferred in certain embodiments of the invention that the δ-opioid modulator compound does not substantially cross the blood-brain barrier. The phrase "does not substantially cross," as used herein, means that less than about 20% by weight of the compound employed in the present methods crosses the blood-brain barrier, preferably less than about 15% by weight, more preferably less than about 10% by weight, even more preferably less than about 5% by weight and most preferably 0% by weight of the compound crosses the blood-brain barrier. Selected compounds can be evaluated for CNS penetration, for example, by determining plasma and brain levels following i.v. administration.

Accordingly, in certain embodiments, the present invention is directed, in part, to novel spiro(2H-1-benzopyran-2,4'-piperidine and spiro[1,2,3,4-tetrahydronaphthalene-2,4'-piperidine compounds of formula I:

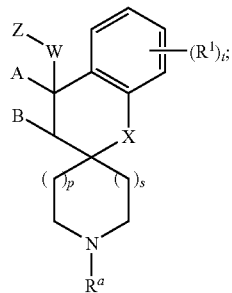

wherein:
W is alkylene;
Z is alkoxy, —C(=O)—R$^2$, —NR$^3$—C(=O)—R$^4$, or —NR$^3$S(=O)$_m$alkyl;
each R$^1$ is independently carboxy, hydroxy, alkoxy, halo, aminocarbonyl, N-alkylaminocarbonyl, or N,N-dialkylaminocarbonyl;
R$^2$ is —NR$^5$R$^6$ or alkoxy;
R$^3$ and R$^a$ are each independently H or alkyl;
R$^4$ is alkyl or —NR$^5$R$^6$;
R$^5$ and R$^6$ are each independently H or alkyl, or R$^5$ and R$^6$ taken together with the nitrogen atom to which they are connected form a 3- to 8-membered heterocycloalkyl ring in which 1 or 2 of the heterocycloalkyl ring carbon atoms independently may each be optionally replaced by —O—, —S—, —N(R$^7$)—, —N(R$^8$)—C(=O)—, or —C(=O)—N(R$^9$)—;
R$^7$, R$^8$, and R$^9$ are each independently H or alkyl;
X is —CH$_2$—, —S(=O)$_m$—, or —O—;
A and B are each H, or taken together with the carbon atoms through which they are connected form a double bond;
each m is independently 0, 1, or 2;
p and t are each independently 0, 1, or 2; and
s is 1 or 2; provided that the sum of p+s is 1, 2, or 3;
or a pharmaceutically acceptable salt thereof.

In formula I above, A and B are each H or taken together with the carbon atoms through which they are connected form a double bond. In preferred embodiments, A and B are each H. In other preferred embodiments, A and B are taken together with the carbon atoms through which they are connected to form a double bond.

In the above formula I, X is —CH$_2$— or —O—. In certain preferred embodiments, X is —CH$_2$—, while in other preferred embodiments, X is —O—.

In formula I above, Z is alkoxy, —C(=O)—R$^2$, —NR$^3$—C(=O)—R$^4$, or —NR$^3$S(=O)$_2$alkyl. In preferred form, Z is —C(=O)—R$^2$, —NR$^3$—C(=O—)—R$^4$, or —NR$^3$S(=O)$_2$ alkyl, with —C(=O)—R$^2$ or —NR$^3$—C(=O)—R$^4$ being more preferred. Even more preferably, Z is —C(=O)—R$^2$.

Each R$^1$ in formula I above is independently carboxy, hydroxy, alkoxy, halo, aminocarbonyl, N-alkylaminocarbonyl, or N,N-dialkylaminocarbonyl. In preferred embodiments, each R$^1$ is independently carboxy, hydroxy, alkoxy, halo, aminocarbonyl, or N-alkylaminocarbonyl, with hydroxy, alkoxy, or halo being more preferred. A preferred alkoxy group is methoxy, and a preferred halogen atom is fluoro.

In the above formula I, R$^2$ is —NR$^5$R$^6$ or alkoxy. In certain preferred embodiments, R$^2$ is —NR$^5$R$^6$.

Each R$^3$ and R$^a$ in formula I above is independently H or alkyl. In certain preferred embodiments, R$^3$ is each H, while in certain other preferred embodiments, R$^3$ is alkyl. In preferred embodiments, R$^a$ is H.

In formula I above, R$^4$ is alkyl or —NR$^5$R$^6$. In certain preferred embodiments, R$^4$ is alkyl, while in other preferred embodiments, R$^4$ is —NR$^5$R$^6$.

R$^5$ and R$^6$ in formula I are each independently H or alkyl, or R$^5$ and R$^6$ taken together with the nitrogen atom to which they are connected form a 3- to 8-membered heterocycloalkyl ring in which 1 or 2 of the heterocycloalkyl ring carbon atoms independently may each be optionally replaced by —O—, —S—, —N(R$^7$)—, —N(R$^8$)—C(=O)—, or —C(=O)—N(R$^9$)—. In certain preferred embodiments, R$^5$ and R$^6$ are each independently H or alkyl, with alkyl being more preferred. In other preferred embodiments, R$^5$ and R$^6$ are taken together with the nitrogen atom to which they are connected to form a 3- to 8-membered heterocycloalkyl ring, more preferably a 3- to 5-membered heterocycloalkyl ring, in which 1 or 2 of the heterocycloalkyl ring carbon atoms independently may each be optionally replaced by —O—, —S—, —N(R$^7$)—, —N(R$^8$)—C(=O)—, or —C(=O)—N(R$^9$)—.

In formula I above, each m, p and t is independently 0, 1 or 2. In certain preferred embodiments, p is 0 or 1, with 1 being more preferred. Also in certain preferred embodiments, t is 0 or 1, more preferably 0. In certain other preferred embodiments, m is 2.

In formula I above, s is 1 or 2, with 1 being preferred.

In the above formula I, the sum of p+s is 1, 2, or 3. In preferred form, the sum of p+s is 2 or 3, with 2 being more preferred.

A preferred class of compounds useful in the practice of the present invention include those described by formula I which have the following formula II:

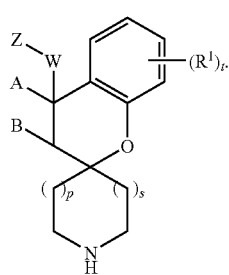

II where A, B, W, Z, $R^1$, p, s and t are as described above.

An even more preferred class of compounds useful in the practice of the present invention include those described by formulas I and II which have the following formula III:

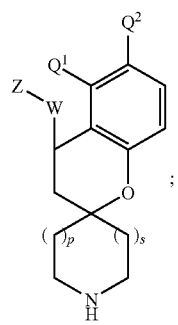

III wherein:

$Q^1$ and $Q^2$ are each independently H, carboxy, hydroxy, alkoxy, halo, aminocarbonyl, N-alkylaminocarbonyl, or N,N-dialkylaminocarbonyl, and W, Z, p and s are as described above.

In the above formula III, $Q^1$ and $Q^2$ are each independently H, carboxy, hydroxy, alkoxy, halo, aminocarbonyl, N-alkylaminocarbonyl, or N,N-dialkylaminocarbonyl. In certain preferred embodiments, at least one of $Q^1$ and $Q^2$ is H and the other of $Q^1$ and $Q^2$ is carboxy, hydroxy, alkoxy, halo, aminocarbonyl, N-alkylaminocarbonyl, or N,N-dialkylaminocarbonyl. In certain more preferred embodiments, at least one of $Q^1$ and $Q^2$ is H and the other of $Q^1$ and $Q^2$ is carboxy, hydroxy, alkoxy, halo, aminocarbonyl, or N-alkylaminocarbonyl. In certain preferred embodiments, both $Q^1$ and $Q^2$ are hydrogen while in other preferred embodiments, $Q^1$ is hydroxy or alkoxy.

Another preferred class of compounds useful in the practice of the present invention include those described by formula I which have the following formula IV:

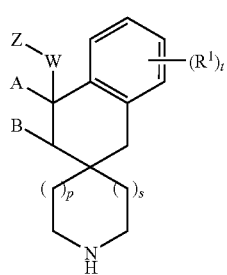

IV wherein A, B, W, Z, $R^1$, p, s and t are as described above. An even more preferred class of compounds useful in the practice of the present invention include those described by formulas I and IV which have the following formula V:

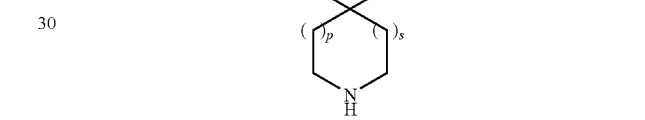

V wherein:

$Q^1$ and $Q^2$ are each independently H, carboxy, hydroxy, alkoxy, halo, aminocarbonyl, N-alkylaminocarbonyl, or N,N-dialkylaminocarbonyl, and W, Z, p and s are as described above.

In formula V, $Q^1$ and $Q^2$ are each independently H, carboxy, hydroxy, alkoxy, halo, aminocarbonyl, N-alkylaminocarbonyl, or N,N-dialkylaminocarbonyl. In certain preferred embodiments, at least one of $Q^1$ and $Q^2$ is H and the other of $Q^1$ and $Q^2$ is carboxy, hydroxy, alkoxy, halo, aminocarbonyl, N-alkylaminocarbonyl, or N,N-dialkylaminocarbonyl. In certain more preferred embodiments, at least one of $Q^1$ and $Q^2$ is H and the other of $Q^1$ and $Q^2$ is carboxy, hydroxy, alkoxy, halo, aminocarbonyl, or N-alkylaminocarbonyl. In certain preferred embodiments, both $Q^1$ and $Q^2$ are hydrogen while in other preferred embodiments, $Q^1$ is hydroxy or alkoxy.

In certain preferred embodiments, the compounds of the invention are selected from the group consisting of:
4-[2-(N,N-diethylaminocarbonyl)ethyl]-spiro[2H,1-benzopyran-2,4'-piperidine];
4-[3-(N,N-diethylaminocarbonyl)propyl]-spiro[2H,1-benzopyran-2,4'-piperidine];
4-[2-(N,N-diethylaminocarbonyl)ethyl]-spiro[3,4-dihydro-2H,1-benzopyran-2,4'-piperidine];
4-[3-(N,N-diethylaminocarbonyl)propyl]-spiro[3,4-dihydro-2H,1-benzopyran-2,4'-piperidine];
4-[3-(ethoxycarbonyl)propyl]-spiro[2H,1-benzopyran-2,4'-piperidine];
4-[3-(N,N-diisopropylaminocarbonyl)propyl]-spiro[3,4-dihydro-2H,1-benzopyran-2,4'-piperidine];

4-[3-(1-(isoindolin-2-yl)carbonyl)propyl]-spiro[3,4-dihydro-2H,1-benzopyran-2,4'-piperidine];
4-[3-(N-ethylaminocarbonyl)propyl]-spiro[3,4-dihydro-2H,1-benzopyran-2,4'-piperidine];
4-[3-(N-butylaminocarbonyl)propyl]-spiro[3,4-dihydro-2H,1-benzopyran-2,4'-piperidine];
4-[4-(N,N-diethylaminocarbonyl)butyl]-spiro[3,4-dihydro-2H,1-benzopyran-2,4'-piperidine];
4-[5-(N,N-diethylaminocarbonyl)pentyl]-spiro[3,4-dihydro-2H,1-benzopyran-2,4'-piperidine];
4-[5-(N,N-diisopropylaminocarbonyl)pentyl]-spiro[3,4-dihydro-2H,1-benzopyran-2,4'-piperidine];
4-[4-(N,N-diethylaminocarbonyl)butyl]-spiro[6-fluoro-3,4-dihydro-2H,1-benzopyran-2,4'-piperidine];
4-[4-(N,N-diethylaminocarbonyl)butyl]-spiro[5-methoxy-3,4-dihydro-2H,1-benzopyran-2,4'-piperidine];
4-[4-(N,N-diethylaminocarbonyl)butyl]-spiro[5-hydroxy-3,4-dihydro-2H,1-benzopyran-2,4'-piperidine];
4-[3-(N,N-diethylaminocarbonylamino)propyl]-spiro[3,4-dihydro-2H,1-benzopyran-2,4'-piperidine];
4-[3-(N-(2-ethylbutanoyl)amino)propyl]-spiro[3,4-dihydro-2H,1-benzopyran-2,4'-piperidine];
4-[(3-(N-methyl-N-(2-ethylbutanoyl)amino)propyl]-spiro[3,4-dihydro-2H,1-benzopyran-2,4'-piperidine];
4-[(3-(ethylsulfonylamino)propyl]-spiro[3,4-dihydro-2H,1-benzopyran-2,4'-piperidine];
4-[(3-(N-methyl-N-(ethylsulfonyl)amino)propyl]-spiro[3,4-dihydro-2H,1-benzopyran-2,4'-piperidine];
4-[(N,N-diethylaminocarbonyl)methyl]-spiro[3,4-dihydro-2H,1-benzopyran-2,4'-piperidine];
4-[(N,N-diethylaminocarbonylmethylaminocarbonyl)methyl]-spiro[3,4-dihydro-2H,1-benzopyran-2,4'-piperidine];
4-[(2-(N,N-diethylaminocarbonylmethyloxy)ethyl]-spiro[3,4-dihydro-2H,1-benzopyran-2,4'-piperidine];
4-[(4-(methoxycarbonyl)butyl]-spiro[6-fluoro-1,2,3,4-tetrahydronaphthalene-2,4'-piperidine];
4-[(4-N,N-diethylaminocarbonyl)butyl]-spiro[6-fluoro-1,2,3,4-tetrahydronaphthalene-2,4'-piperidine];
4-[(4-N,N-diethylaminocarbonyl)butyl]-spiro[1,2,3,4-tetrahydronaphthalene-2,4'-piperidine];
4-[(4-N,N-diethylaminocarbonyl)butyl]-spiro[6-methoxy-1,2,3,4-tetrahydronaphthalene-2,4'-piperidine];
4-[(4-N,N-diethylaminocarbonyl)butyl]-spiro[6-hydroxy-1,2,3,4-tetrahydronaphthalene-2,4'-piperidine];
4-[(4-N,N-diethylaminocarbonyl)butyl]-spiro[6-carboxy-1,2,3,4-tetrahydronaphthalene-2,4'-piperidine];
4-[(4-N,N-diethylaminocarbonyl)butyl]-spiro[6-aminocarbonyl-1,2,3,4-tetrahydronaphthalene-2,4'-piperidine];
4-[(4-N,N-diethylaminocarbonyl)butyl]-spiro[6-N-methylaminocarbonyl-1,2,3,4-tetrahydronaphthalene-2,4'-piperidine]; and
4-[(4-N,N-diethylaminocarbonyl)butyl]-spiro[6-N-ethylcarbonyl-1,2,3,4-tetrahydronaphthalene-2,4'-piperidine];
or a pharmaceutically acceptable salt thereof.

Preferably the compounds of the invention are selected from the group consisting of:
4-[3-(N,N-diethylaminocarbonyl)propyl]-spiro[3,4-dihydro-2H,1-benzopyran-2,4'-piperidine];
4-[3-(N,N-diisopropylaminocarbonyl)propyl]-spiro[3,4-dihydro-2H,1-benzopyran-2,4'-piperidine];
4-[4-(N,N-diethylaminocarbonyl)butyl]-spiro[3,4-dihydro-2H,1-benzopyran-2,4'-piperidine];
4-[5-(N,N-diethylaminocarbonyl)pentyl]-spiro[3,4-dihydro-2H,1-benzopyran-2,4'-piperidine];
4-[5-(N,N-diisopropylaminocarbonyl)pentyl]-spiro[3,4-dihydro-2H,1-benzopyran-2,4'-piperidine];
4-[4-(N,N-diethylaminocarbonyl)butyl]-spiro[6-fluoro-3,4-dihydro-2H,1-benzopyran-2,4'-piperidine];
4-[4-(N,N-diethylaminocarbonyl)butyl]-spiro[5-hydroxy-3,4-dihydro-2H,1-benzopyran-2,4'-piperidine];
4-[(3-(ethylsulfonylamino)propyl]-spiro[3,4-dihydro-2H,1-benzopyran-2,4'-piperidine];
4-[(4-N,N-diethylaminocarbonyl)butyl]-spiro[6-fluoro-1,2,3,4-tetrahydronaphthalene-2,4'-piperidine];
4-[(4-N,N-diethylaminocarbonyl)butyl]-spiro[1,2,3,4-tetrahydronaphthalene-2,4'-piperidine];
4-[(4-N,N-diethylaminocarbonyl)butyl]-spiro[6-methoxy-1,2,3,4-tetrahydronaphthalene-2,4'-piperidine];
4-[(4-N,N-diethylaminocarbonyl)butyl]-spiro[6-hydroxy-1,2,3,4-tetrahydronaphthalene-2,4'-piperidine];
4-[(4-N,N-diethylaminocarbonyl)butyl]-spiro[6-aminocarbonyl-1,2,3,4-tetrahydronaphthalene-2,4'-piperidine];
4-[(4-N,N-diethylaminocarbonyl)butyl]-spiro[6-N-methylaminocarbonyl-1,2,3,4-tetrahydronaphthalene-2,4'-piperidine]; and
4-[(4-N,N-diethylaminocarbonyl)butyl]-spiro[6-N-ethylcarbonyl-1,2,3,4-tetrahydronaphthalene-2,4'-piperidine];
or a pharmaceutically acceptable salt thereof.

More preferably, the compounds of the invention are selected from the group consisting of:
4-[3-(N,N-diethylaminocarbonyl)propyl]-spiro[3,4-dihydro-2H,1-benzopyran-2,4'-piperidine];
4-[3-(N,N-diisopropylaminocarbonyl)propyl]-spiro[3,4-dihydro-2H,1-benzopyran-2,4'-piperidine];
4-[4-(N,N-diethylaminocarbonyl)butyl]-spiro[3,4-dihydro-2H,1-benzopyran-2,4'-piperidine];
4-[5-(N,N-diethylaminocarbonyl)pentyl]-spiro[3,4-dihydro-2H,1-benzopyran-2,4'-piperidine];
4-[4-(N,N-diethylaminocarbonyl)butyl]-spiro[6-fluoro-3,4-dihydro-2H,1-benzopyran-2,4'-piperidine];
4-[4-(N,N-diethylaminocarbonyl)butyl]-spiro[5-hydroxy-3,4-dihydro-2H,1-benzopyran-2,4'-piperidine];
4-[(4-N,N-diethylaminocarbonyl)butyl]-spiro[6-hydroxy-1,2,3,4-tetrahydronaphthalene-2,4'-piperidine];
4-[(4-N,N-diethylaminocarbonyl)butyl]-spiro[6-aminocarbonyl-1,2,3,4-tetrahydronaphthalene-2,4'-piperidine];
4-[(4-N,N-diethylaminocarbonyl)butyl]-spiro[6-N-methylaminocarbonyl-1,2,3,4-tetrahydronaphthalene-2,4'-piperidine]; and
4-[(4-N,N-diethylaminocarbonyl)butyl]-spiro[6-N-ethylcarbonyl-1,2,3,4-tetrahydronaphthalene-2,4'-piperidine];
or a pharmaceutically acceptable salt thereof.

Still more preferably, the compounds of the invention are selected from the group consisting of:
4-[4-(N,N-diethylaminocarbonyl)butyl]-spiro[5-hydroxy-3,4-dihydro-2H,1-benzopyran-2,4'-piperidine];
4-[(4-N,N-diethylaminocarbonyl)butyl]-spiro[6-hydroxy-1,2,3,4-tetrahydronaphthalene-2,4'-piperidine];
4-[(4-N,N-diethylaminocarbonyl)butyl]-spiro[6-aminocarbonyl-1,2,3,4-tetrahydronaphthalene-2,4'-piperidine];
4-[(4-N,N-diethylaminocarbonyl)butyl]-spiro[6-N-methylaminocarbonyl-1,2,3,4-tetrahydronaphthalene-2,4'-piperidine]; and
4-[(4-N,N-diethylaminocarbonyl)butyl]-spiro[6-N-ethylcarbonyl-1,2,3,4-tetrahydronaphthalene-2,4'-piperidine];
or a pharmaceutically acceptable salt thereof.

In any of the above teachings, a compound of the invention may be either a compound of one of the formulae herein described, or a stereoisomer, prodrug, pharmaceutically acceptable salt, hydrate, solvate, acid salt hydrate, N-oxide or isomorphic crystalline form thereof.

The compounds employed in the methods and compositions of the present invention may exist in prodrug form. As used herein, "prodrug" is intended to include any covalently bonded carriers which release the active parent drug, for example, as according to formula I or other formulas or compounds as described herein, in vivo when such prodrug is administered to a mammalian subject. Since prodrugs are known to enhance numerous desirable qualities of pharmaceuticals (e.g., solubility, bioavailability, manufacturing, etc.), the compounds described herein may, if desired, be delivered in prodrug form. Thus, the present invention contemplates compositions and methods involving prodrugs. Prodrugs of the compounds employed in the present invention, for example formula I, II, III, IV, or V, may be prepared by modifying functional groups present in the compound in such a way that the modifications are cleaved, either in routine manipulation or in vivo, to the parent compound.

Accordingly, prodrugs include, for example, compounds described herein in which a hydroxy, amino, or carboxy group is bonded to any group that, when the prodrug is administered to a mammalian subject, cleaves to form a free hydroxyl, free amino, or carboxylic acid, respectively. Examples include, but are not limited to, acetate, formate and benzoate derivatives of alcohol and amine functional groups; and alkyl, cycloalkyl, aryl, and alkylaryl esters such as methyl, ethyl, propyl, isopropyl, butyl, isobutyl, sec-butyl, tert-butyl, cyclopropyl, phenyl, benzyl, and phenethyl esters, and the like.

Compounds described herein may contain one or more asymmetrically substituted carbon atoms, and may be isolated in optically active or racemic forms. Thus, all isomeric forms of a structure, including all stereogenic (such as enantiomeric, diastereomeric, and/or meso forms, whether chiral or racemic), all achiral, all geometric, and/or all conformational isomeric forms are intended, unless the specific stereochemical or other isomeric form is specifically indicated and/or achiral. It is well known in the art how to prepare and isolate such isomeric forms of a structure including those having stereogenic centers including those stereogenic forms wherein the structure is present in optically active form. For example, mixtures of stereoisomers may be separated by standard techniques including, but not limited to, resolution of racemic forms, normal, reverse-phase, and chiral chromatography, preferential salt formation, recrystallization, and the like, or by chiral synthesis either from chiral starting materials or by deliberate synthesis of target chiral centers.

The compounds of the present invention may be prepared in a number of ways well known to those skilled in the art. The compounds can be synthesized, for example, by the methods described below, or variations thereon as appreciated by the skilled artisan. All processes disclosed in association with the present invention are contemplated to be practiced on any scale, including milligram, gram, multigram, kilogram, multikilogram or commercial industrial scale.

As will be readily understood, functional groups present may contain protecting groups during the course of synthesis. Protecting groups are known per se as chemical functional groups that can be selectively appended to and removed from functionalities, such as hydroxyl groups and carboxyl groups. These groups are present in a chemical compound to render such functionality inert to chemical reaction conditions to which the compound is exposed. Any of a variety of protecting groups may be employed with the present invention. Preferred protecting groups include the benzyloxycarbonyl group and the tert-butyloxycarbonyl group. Other preferred protecting groups that may be employed in accordance with the present invention may be described in Greene, T. W. and Wuts, P. G. M., *Protective Groups in Organic Synthesis* 2nd. Ed., Wiley & Sons, 1991, the disclosures of which are hereby incorporated herein by reference, in their entirety.

The δ-agonist compounds of the present invention may be administered by any means that results in the contact of the active agent with the agent's site of action in the body of a patient. The compounds may be administered by any conventional means available for use in conjunction with pharmaceuticals, either as individual therapeutic agents or in a combination of therapeutic and/or prophylactic agents. For example, they may be administered as the sole active agent in a pharmaceutical composition, or they can be used in combination with other therapeutically active ingredients including, for example, opioid analgesic agents. In such combinations, selected compounds of the invention may provide equivalent or even enhanced therapeutic activity such as, for example, pain ameliorization, while providing reduced adverse side effects associated with opioids, such as addiction or pruritus, by lowering the amount of opioid required to achieve a therapeutic effect.

Generally speaking, therapeutic compounds of this invention may be administered to a patient alone or in combination with a pharmaceutically acceptable carrier. Accordingly, the compounds of the invention, for example, compounds of formulas I, II, III, IV, and/or V, are preferably combined with a pharmaceutical carrier selected on the basis of the chosen route of administration and standard pharmaceutical practice as described, for example, in *Remington's Pharmaceutical Sciences* (Mack Publishing Co., Easton, Pa., 1980), the disclosures of which are hereby incorporated herein by reference, in their entireties. The carrier(s) must be acceptable in the sense of being compatible with the other ingredients of the composition and not deleterious to the recipient thereof.

In addition to the pharmaceutical carrier, the compound of the invention, for example, compounds of formula I, II, III, IV, and/or V, may be co-administered with at least one opioid, preferably a μ opioid receptor modulator compound. In certain embodiments, the combination of the compounds of formula I, II, III, IV, or V, with at least one opioid, preferably a μ opioid receptor modulator compound, provides a synergistic analgesic effect. The utility of such combination products may be determined by those skilled in the art using established animal models. Suitable opioids include, without limitation, alfentanil, allylprodine, alphaprodine, anileridine, benzyl-morphine, bezitramide, buprenorphine, butorphanol, clonitazene, codeine, cyclazocine, desomorphine, dextromoramide, dezocine, diampromide, diamorphone, dihydrocodeine, dihydromorphine, dimenoxadol, dimepheptanol, dimethylthiambutene, dioaphetylbutyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacylmorphan, lofentanil, loperamide, meperidine (pethidine), meptazinol, metazocine, methadone, metopon, morphine, myrophine, nalbuphine, narceine, nicomorphine, norlevorphanol, normethadone, nalorphine, normorphine, norpinanone, opium, oxycodone, oxymorphone, papavereturn, pentazocine, phenadoxone, phenomorphan, phanazocine, phenoperidine, piminodine, piritramide, propheptazine, promedol, properidine, propiram, propoxyphene, sulfentanil, tilidine, tramadol, diastereoisomers thereof, pharmaceutically acceptable salts thereof, complexes thereof; and mixtures thereof.

The pain ameliorating and/or opioid combination products of the present compositions may further include one or more other active ingredients that may be conventionally employed in analgesic and/or cough-cold-antitussive combination products. Such conventional ingredients include, for example, aspirin, acetaminophen, phenylpropanolamine, phenylephrine, chlorpheniramine, caffeine, and/or guaifenesin. Typical or conventional ingredients that may be included in the opioid component are described, for example, in the *Physicians' Desk Reference*, 1999, the disclosure of which is hereby incorporated herein by reference, in its entirety.

In addition, the opioid component may further include one or more compounds that may be designed to enhance the analgesic potency of the opioid and/or to reduce analgesic tolerance development. Such compounds include, for example, dextromethorphan or other NMDA antagonists (Mao, M. J. et al., *Pain* 1996, 67, 361), L-364,718 and other CCK antagonists (Dourish, C. T. et al., *Eur. J. Pharmacol.* 1988, 147, 469), NOS inhibitors (Bhargava, H. N. et al., *Neuropeptides* 1996, 30, 219), PKC inhibitors (Bilsky, E. J. et al., *J. Pharmacol. Exp. Ther.* 1996, 277, 484), and dynorphin antagonists or antisera (Nichols, M. L. et al., *Pain* 1997, 69, 317). The disclosures of each of the foregoing documents are hereby incorporated herein by reference, in their entireties.

Other opioids, optional conventional opioid components, and optional compounds for enhancing the analgesic potency of the opioid and/or for reducing analgesic tolerance development, that may be employed in the methods and compositions of the present invention, in addition to those exemplified above, would be readily apparent to one of ordinary skill in the art, once armed with the teachings of the present disclosure.

Compounds of the present invention can be administered to a mammalian host in a variety of forms adapted to the chosen route of administration, e.g., orally or parenterally. Parenteral administration in this respect includes administration by the following routes: intravenous, intramuscular, subcutaneous, rectal, intraocular, intrasynovial, transepithelial including transdermal, ophthalmic, sublingual and buccal; topically including ophthalmic, dermal, ocular, rectal, and nasal inhalation via insufflation aerosol.

The active compound may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the active compound may be incorporated with excipient and used in the form of ingestible tablets, buccal tablets, troches, capsules, elixirs, suspensions, syrups, wafers, and the like. Such compositions and preparations should preferably contain at least 0.1% of active compound. The percentage concentration of active compound in the compositions and preparations may, of course, be varied, and the relative proportions of active ingredient and carrier may be determined, for example, by the solubility and chemical nature of the compound, chosen route of administration and standard pharmaceutical practice. Generally speaking, the concentration of active agent may be, for example, from about 2 to about 6% of the weight of the unit. The amount of active compound in such therapeutically useful compositions is preferably such that a suitable dosage will be obtained. Preferred compositions or preparations according to the present invention may be prepared so that an oral dosage unit form contains from about 0.1 to about 1000 mg of active compound (and all combinations and subcombinations of dosage ranges and specific dosage amounts therein).

The tablets, troches, pills, capsules and the like may also contain one or more of the following: a binder, such as gum tragacanth, acacia, corn starch or gelatin; an excipient, such as dicalcium phosphate; a disintegrating agent, such as corn starch, potato starch, alginic acid and the like; a lubricant, such as magnesium stearate; a sweetening agent such as sucrose, lactose or saccharin; or a flavoring agent, such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup or elixir may contain the active compound, sucrose as a sweetening agent, methyl and propylparabens as preservatives, a dye and flavoring, such as cherry or orange flavor. Of course, any material used in preparing any dosage unit form is preferably pharmaceutically pure and substantially non-toxic in the amounts employed. In addition, the active compound may be incorporated into sustained-release preparations and formulations.

The active compound may also be administered parenterally or intraperitoneally. Solutions of the active compound as a free base or a pharmacologically acceptable salt can be prepared in water suitably mixed with a surfactant, such as hydroxypropylcellulose. A dispersion can also be prepared in glycerol, liquid polyethylene glycols and mixtures thereof and in oils. Under ordinary conditions of storage and use, these preparations may contain a preservative to prevent the growth of microorganisms.

The pharmaceutical forms suitable for injectable use include, for example, sterile aqueous solutions or dispersions and sterile powders for the extemporaneous preparation of sterile injectable solutions or dispersions. In all cases, the form is preferably sterile and fluid to provide easy syringability. It is preferably stable under the conditions of manufacture and storage and is preferably preserved against the contaminating action of microorganisms such as bacteria and fungi. The carrier may be a solvent or dispersion medium containing, for example, water, ethanol, polyol (for example, glycerol, propylene glycol, liquid polyethylene glycol and the like), suitable mixtures thereof, and vegetable oils. The proper fluidity can be maintained, for example, by the use of a coating, such as lecithin, by the maintenance of the required particle size in the case of a dispersion, and by the use of surfactants. The prevention of the action of microorganisms may be achieved by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions may be achieved by the use of agents delaying absorption, for example, aluminum monostearate and gelatin.

Sterile injectable solutions may be prepared by incorporating the active compound in the required amount, in the appropriate solvent, with various of the other ingredients enumerated above, as required, followed by filtered sterilization. Generally, dispersions may be prepared by incorporating the sterilized active ingredient into a sterile vehicle that contains the basic dispersion medium and the required other ingredients from those enumerated above. In the case of sterile powders for the preparation of sterile injectable solutions, the preferred methods of preparation may include vacuum drying and the freeze-drying technique that yield a powder of the active ingredient, plus any additional desired ingredient from the previously sterile-filtered solution thereof.

The dosage of the compounds of the present invention that will be most suitable for prophylaxis or treatment will vary with the form of administration, the particular compound chosen and the physiological characteristics of the particular patient under treatment. Generally, small dosages may be used initially and, if necessary, increased by small increments until the desired effect under the circumstances is reached. The therapeutic human dosage, based on physiological studies using rats, may generally range from about 0.01 mg to about 100 mg/kg of body weight per day, and all combinations and subcombinations of ranges and specific dosages therein. Alternatively, the therapeutic human dosage may be from about 0.4 mg to about 10 g or higher, and may be administered in several different dosage units from once to several times a day. Generally speaking, oral administration may require higher dosages.

It will be further appreciated that the amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations; such as multiple inhalations from an insufflator or by application of a plurality of drops into the eye.

Combination products of this invention, such as pharmaceutical compositions comprising the compounds of the present invention, for example, compounds of formulas I, II, II, IV, and/or V, in combination with other therapeutic compounds described herein may be in any dosage form, such as those described herein, and can also be administered in various ways, as described herein. In a preferred embodiment, the combination products of the invention are formulated together, in a single dosage form (that is, combined together in one capsule, tablet, powder, or liquid, etc.). When the combination products are not formulated together in a single dosage form, the compounds of the present invention and other therapeutic compounds described herein may be administered at the same time (that is, together), or in any order. When not administered at the same time, preferably the administration of a compound of the invention and other therapeutic compounds as described herein occurs less than about one hour apart, more preferably less than about 30 minutes apart, even more preferably less than about 15 minutes apart, and still more preferably less than about 5 minutes apart. Preferably, administration of the combination products of the invention is oral, although other routes of administration, as described above, are contemplated to be within the scope of the present invention. Although it is preferable that the compound of the invention and other therapeutic compounds as described herein are both administered in the same fashion (that is, for example, both orally), if desired, they may each be administered in different fashions (that is, for example, one component of the combination product may be administered orally, and another component may be administered intravenously). The dosage of the combination products of the invention may vary depending upon various factors such as the pharmacodynamic characteristics of the particular agent and its mode and route of administration, the age, health and weight of the recipient, the nature and extent of the symptoms, the kind of concurrent treatment, the frequency of treatment, and the effect desired.

Although the proper dosage of the combination products of this invention will be readily ascertainable by one skilled in the art, once armed with the present disclosure, by way of general guidance, where one or more compounds of the present invention is combined with one or more other therapeutic compounds as described herein, for example, typically a daily dosage may range from about 0.01 to about 100 milligrams of the compound of the invention (and all combinations and subcombinations of ranges therein) and about 0.001 to about 100 milligrams of other therapeutic compounds as described herein (and all combinations and subcombinations of ranges therein), per kilogram of patient body weight. Preferably, a daily dosage may be about 0.1 to about 10 milligrams of the compound of the invention and about 0.01 to about 10 milligrams of other therapeutic compounds as described herein per kilogram of patient body weight. Even more preferably, the daily dosage may be about 1.0 milligrams of the compound of the invention and about 0.1 milligrams of other therapeutic compounds as described herein per kilogram of patient body weight. With regard to a typical dosage form of this type of combination product, such as a tablet, the compound of the invention generally may be present in an amount of about 15 to about 200 milligrams, and the other therapeutic compounds as described herein in an amount of about 0.1 to about 4 milligrams.

Particularly when provided as a single dosage form, the potential exists for a chemical interaction between the combined active ingredients (for example, a compound of the invention and other therapeutic compounds as described herein). For this reason, the preferred dosage forms of the combination products of this invention are formulated such that although the active ingredients are combined in a single dosage form, the physical contact between the active ingredients is minimized (that is, reduced).

In order to minimize contact, one embodiment of this invention where the product is orally administered provides for a combination product wherein one active ingredient is enteric coated. By enteric coating one or more of the active ingredients, it is possible not only to minimize the contact between the combined active ingredients, but also, it is possible to control the release of one of these components in the gastrointestinal tract such that one of these components is not released in the stomach but rather is released in the intestines. Another embodiment of this invention where oral administration is desired provides for a combination product wherein one of the active ingredients is coated with a sustained-release material that effects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

Dosage forms of the combination products of the present invention wherein one active ingredient is enteric coated can be in the form of tablets such that the enteric coated component and the other active ingredient are blended together and then compressed into a tablet or such that the enteric coated component is compressed into one tablet layer and the other active ingredient is compressed into an additional layer. Optionally, in order to further separate the two layers, one or more placebo layers may be present such that the placebo layer is between the layers of active ingredients. In addition, dosage forms of the present invention can be in the form of capsules wherein one active ingredient is compressed into a tablet or in the form of a plurality of microtablets, particles, granules or non-perils, which are then enteric coated. These enteric coated microtablets, particles, granules or non-perils are then placed into a capsule or compressed into a capsule along with a granulation of the other active ingredient.

These as well as other ways of minimizing contact between the components of combination products of the present invention, whether administered in a single dosage form or administered in separate forms but at the same time by the same manner, will be readily apparent to those skilled in the art, once armed with the present disclosure.

The dose may also be provided by controlled release of the compound, by techniques well known to those in the art.

The compounds of the invention may also be formulated with other optional active ingredients, in addition to or instead of the optional opioids, and in addition to the optional pharmaceutical-acceptable carriers. Other active ingredients include, but are not limited to, antibiotics, antivirals, antifungals, anti-inflammatories, including steroidal and non-steroidal anti-inflammatories, anesthetics, cardioprotective agents, and mixtures thereof. Such additional ingredients include any of the following:

a. Antibacterial Agents

Aminoglycosides, such as Amikacin, Apramycin, Arbekacin, Bambermycins, Butirosin, Dibekacin, Dihydrostreptomycin, Fortimicin(s), Fradiomycin, Gentamicin, Ispamicin, Kanamycin, Micronomicin, Neomycin, Neomycin Undecylenate, Netilmicin, Paromomycin, Ribostamycin, Sisomicin, Spectinomycin, Streptomycin, Streptonicozid and Tobramycin;

Amphenicols, such as Azidamfenicol, Chloramphenicol, Chloramphenicol Palmirate, Chloramphenicol Pantothenate, Florfenicol, Thiamphenicol;

Ansamycins, such as Rifamide, Rifampin, Rifamycin and Rifaximin;

β-Lactams;

Carbapenems, such as Imipenem;

Cephalosporins, such as 1-Carba (dethia) Cephalosporin, Cefactor, Cefadroxil, Cefamandole, Cefatrizine, Cefazedone, Cefazolin, Cefixime, Cefmenoxime, Cefodizime, Cefonicid, Cefoperazone, Ceforanide, Cefotaxime, Cefotiam, Cefpimizole, Cefpirimide, Cefpodoxime Proxetil, Cefroxadine, Cefsulodin, Ceftazidime, Cefteram, Ceftezole, Ceftibuten, Ceftizoxime, Ceftriaxone, Cefuroxime, Cefuzonam, Cephacetrile Sodium, Cephalexin, Cephaloglycin, Cephaloridine, Cephalosporin, Cephalothin, Cephapirin Sodium, Cephradine and Pivcefalexin;

Cephamycins such as Cefbuperazone, Cefmetazole, Cefminox, Cefetan and Cefoxitin;

Monobactams such as Aztreonam, Carumonam and Tigemonan;

Oxacephems such as Flomoxef and Moxolactam;

Penicillins such as Amidinocillin, Amdinocillin, Pivoxil, Amoxicillin, Ampicillan, Apalcillin, Aspoxicillin, Azidocillan, Azlocillan, Bacampicillin, Benzylpenicillinic Acid, Benzylpenicillin, Carbenicillin, Carfecillin, Carindacillin, Clometocillin, Cloxacillin, Cyclacillin, Dicloxacillin, Diphenicillin, Epicillin, Fenbenicillin, Floxicillin, Hetacillin, Lenampicillin, Metampicillin, Methicillin, Mezlocillin, Nafcillin, Oxacillin, Penamecillin, Penethamate Hydriodide, Penicillin G Benethamine, Penicillin G Benzathine, Penicillin G Benzhydrylamine, Penicillin G Calcium, Penicillin G Hydragamine, Penicillin G Potassium, Penicillin G. Procaine, Penicillin N, Penicillin O, Penicillin V, Penicillin V Benzathine, Penicillin V Hydrabamine, Penimepicycline, Phenethicillin, Piperacillin, Pivapicillin, Propicillin, Quinacillin, Sulbenicillin, Talampicillin, Temocillin and Ticarcillin;

Lincosumides such as Clindamycin and Lincomycin;

Macrolides such as Azithromycin, Carbomycin, Clarithromycin, Erythromycin(s) and Derivatives, Josamycin, Leucomycins, Midecamycins, Miokamycin, Oleandomycin, Primycin, Rokitamycin, Rosaramicin, Roxithromycin, Spiramycin and Troleandomycin;

Polypeptides such as Amphomycin, Bacitracin, Capreomycin, Colistin, Enduracidin, Enviomycin, Fusafungine, Gramicidin(s), Gramicidin S, Mikamycin, Polymyxin, Polymyxin β-Methanesulfonic Acid, Pristinamycin, Ristocetin, Teicoplanin, Thiostrepton, Tuberactinomycin, Tyrocidine, Tyrothricin, Vancomycin, Viomycin(s), Virginiamycin and Zinc Bacitracin;

Tetracyclines such as Spicycline, Chlortetracycline, Clomocycline, Demeclocycline, Doxycycline, Guamecycline, Lymecycline, Meclocycline, Methacycline, Minocycline, Oxytetracycline, Penimepicycline, Pipacycline, Rolitetracycline, Sancycline, Senociclin and Tetracycline; and others such as Cycloserine, Mupirocin, Tuberin.

b. Synthetic Antibacterials 2,4-Diaminopyrimidines such as Brodimoprim, Tetroxoprim and Trimethoprim;

Nitrofurans such as Furaltadone, Furazolium, Nifuradene, Nifuratel, Nifurfoline, Nifurpirinol, Nifurprazine, Nifurtoinol and Nitrofurantoin;

Quinolones and analogs thereof, such as Amifloxacin, Cinoxacin, Ciprofloxacin, Difloxacin, Enoxacin, Fleroxacin, Flumequine, Lomefloxacin, Miloxacin, Nalidixic Acid, Norfloxacin, Ofloxacin, Oxolinic Acid, Perfloxacin, Pipemidic Acid, Piromidic Acid, Rosoxacin, Temafloxacin and Tosufloxacin;

Sulfonamides such as Acetyl Sulfamethoxypyrazine, Acetyl Sulfisoxazole, Azosulfamide, Benzylsulfamide, Chloramine-β, Chloramine-T, Dichloramine-T, Formosulfathiazole, $N^2$-Formyl-sulfisomidine, $N^4$-β-D-Glucosylsulfanilamide, Mafenide, 4'-(Methyl-sulfamoyl)sulfanilanilide, p-Nitrosulfathiazole, Noprylsulfamide, Phthalylsulfacetamide, Phthalylsulfathiazole, Salazosulfadimidine, Succinylsulfathiazole, Sulfabenzamide, Sulfacetamide, Sulfachlorpyridazine, Sulfachrysoidine, Sulfacytine, Sulfadiazine, Sulfadicramide, Sulfadimethoxine, Sulfadoxine, Sulfaethidole, Sulfaguanidine, Sulfaguanol, Sulfalene, Sulfaloxic Acid, Sulfamerazine, Sulfameter, Sulfamethazine, Sulfamethizole, Sulfamethomidine, Sulfamethoxazole, Sulfamethoxypyridazine, Sulfametrole, sulfamidochrysoidine, Sulfamoxole, Sulfanilamide, Sulfanilamidomethanesulfonic Acid Triethanolamine Salt, 4-Sulfanilamidosalicyclic Acid, $N^4$-Sulfanilylsulfanilamide, Sulfanilylurea, N-Sulfanilyl-3, 4-xylamide, Sulfanitran, Sulfaperine, Sulfaphenazole, Sulfaproxyline, Sulfapyrazine, Sulfapyridine, Sulfasomizole, Sulfasymazine, Sulfathiazole, Sulfathiourea, Sulfatolamide, Sulfisomidine and Sulfisoxazole;

Sulfones, such as Acedapsone, Acediasulfone, Acetosulfone, Dapsone, Diathymosulfone, Glucosulfone, Solasulfone, Succisulfone, Sulfanilic Acid, p-Sulfanilylbenzylamine, p,p'-sulfonyldianiline-N,N'-digalactoside, Sulfoxone and Thiazolsulfone;

Others such as Clofoctol, Hexedine, Magainins, Methenamine, Methenamine Anhydromethylene-citrate, Methenamine Hippurate, Methenamine Mandelate, Methenamine Sulfosalicylate, Nitroxoline, Squalamine and Xibomol.

c. Antifungal (Antibiotics)

Polyenes such as Amphotericin-B, Candicidin, Dermostatin, Filipin, Fungichromin, Hachimycin, Hamycin, Lucensomycin, Mepartricin, Natamycin, Nystatin, Pecilocin, Perimycin; and others, such as Azaserine, Griseofulvin, Oligomycins, Pyrrolnitrin, Siccanin, Tubercidin and Viridin.

d. Antifungal (Synthetic)

Allylamines such as Naftifine and terbinafine;

Imidazoles such as Bifonazole, Butoconazole, Chlordantoin, Chlormidazole, Cloconazole, Clotrimazole, Econazole, Enilconazole, Finticonazole, Isoconazole, Ketoconazole, Miconazole, Omoconazole, Oxiconazole Nitrate, Sulconazole and Tioconazole;

Triazoles such as Fluconazole, Itraconazole, Terconazole;

Others such as Acrisorcin, Amorolfine, Biphenamine, Bromosalicylchloranilide, Buclosamide, Chlophenesin, Ciclopirox, Cloxyquin, Coparaffinate, Diamthazole, Dihydrochloride, Exalamide, Flucytosine, Halethazole, Hexetidine, Loflucarban, Nifuratel, Potassium Iodide, Propionic Acid, Pyrithione, Salicylanilide, Sulbentine, Tenonitrozole, Tolciclate, Tolindate, Tolnaftate, Tricetin, Ujothion, and Undecylenic Acid.

e. Antiglaucoma Agents

Antiglaucoma agents, such as Dapiprazoke, Dichlorphenamide, Dipivefrin and Pilocarpine.

f. Anti-inflammatory Agents

Corticosteroids, aminoarylcarboxylic Acid Derivatives such as Etofenamate, Meclofenamic Acid, Mefanamic Acid, Niflumic Acid;

Arylacetic Acid Derivatives such as Acemetacin, Amfenac Cinmetacin, Clopirac, Diclofenac, Fenclofenac, Fenclorac, Fenclozic Acid, Fentiazac, Glucametacin, Isozepac, Lonazolac, Metiazinic Acid, Oxametacine, Proglumetacin, Sulindac, Tiaramide and Tolmetin;

Arylbutyric Acid Derivatives such as Butibufen and Fenbufen;

Arylcarboxylic Acids such as Clidanac, Ketorolac and Tinoridine;

Arylpropionic Acid Derivatives such as Bucloxic Acid, Carprofen, Fenoprofen, Flunoxaprofen, Ibuprofen, Ibuproxam, Oxaprozin, Piketoprofen, Pirprofen, Pranoprofen, Protizinic Acid and Tiaprofenic Add;

Pyrazoles such as Mepirizole;

Pyrazolones such as Clofezone, Feprazone, Mofebutazone, Oxyphenbutazone, Phenylbutazone, Phenyl Pyrazolidininones, Suxibuzone and Thiazolinobutazone;

Salicylic Acid Derivatives such as Bromosaligenin, Fendosal, Glycol Salicylate, Mesalamine, 1-Naphthyl Salicylate, Olsalazine and Sulfasalazine;

Thiazinecarboxamides such as Droxicam, Isoxicam and Piroxicam;

Others such as e-Acetamidocaproic Acid, S-Adenosylmethionine, 3-Amino-4-hydroxybutyric Acid, Amixetrine, Bendazac, Bucolome, Carbazones, Difenpiramide, Ditazol, Guaiazulene, Heterocyclic Aminoalkyl Esters of Mycophenolic Acid and Derivatives, Nabumetone, Nimesulide, Orgotein, Oxaceprol, Oxazole Derivatives, Paranyline, Pifoxime, 2-substituted-4,6-di-tertiary-butyl-s-hydroxy-1,3-pyrimidines, Proquazone and Tenidap.

g. Antiseptics

Guanidines such as Alexidine, Ambazone, Chlorhexidine and Picloxydine;

Halogens/Halogen Compounds such as Bomyl Chloride, Calcium Iodate, Iodine, Iodine Monochloride, Iodine Trichloride, Iodoform, Povidone-Iodine, Sodium Hypochlorite, Sodium Iodate, Symclosene, Thymol Iodide, Triclocarban, Triclosan and Troclosene Potassium;

Nitrofurans such as Furazolidone, 2-(Methoxymethyl)-5-Nitrofuran, Nidroxyzone, Nifuroxime, Nifurzide and Nitrofurazone;

Phenols such as Acetomeroctol, Chloroxylenol, Hexachlorophene, 1-Naphthyl Salicylate, 2,4,6-Tribromo-m-cresol and 3',4',5-Trichlorosalicylanilide;

Quinolines such as Aminoquinuride, Chloroxine, Chlorquinaldol, Cloxyquin, Ethylhydrocupreine, Halquinol, Hydrastine, 8-Hydroxyquinoline and Sulfate; and others, such as Boric Acid, Chloroazodin, m-Cresyl Acetate, Cupric sulfate and Ichthammol.

h. Antivirals

Purines/Pyrimidinones, such as 2-Acetyl-Pyridine 5-((2-pyridylamino)thiocarbonyl) Thiocarbonohydrazone, Acyclovir, Dideoxyadenosine, Dideoxycytidine, Dideoxyinosine, Edoxudine, Floxuridine, Ganciclovir, Idoxuridine, MADU, Pyridinone, Trifluridine, Vidrarbine and Zidovudline;

others such as Acetylleucine Monoethanolamine, Acridinamine, Alkylisooxazoles, Amantadine, Amidinomycin, Cuminaldehyde Thiosemicarbzone, Foscamet Sodium, Kethoxal, Lysozyme, Methisazone, Moroxydine, Podophyllotoxin, Ribavirin, Rimantadine, Stallimycin, Statolon, Thymosins, Tromantadine and Xenazoic Acid.

i. Agents for Neuralgia/Neuropathic Pain

Mild OTC (over the counter) analgesics, such as aspirin, acetaminophen, and ibuprophen.

Narcotic analgesics, such as codeine.

Anti seizure medications, such as carbamazepine, gabapentin, lamotrigine and phenyloin.

Anti-depressants, such as amitryptiline.

j. Agents for the Treatment of Depression

Selective serotonin re-uptake inhibitors (SSRIs), such as Fluoxetine, Paroxetine, Fluvoxamine, Citaprolam, and Sertraline.

Tricyclics, such as Imipramine, Amitriptyline, Desipramine, Nortriptyline Protriptyline, Trimipramine, Doxepin, Amoxapine, and Clomipramine.

Monoamine Oxidase Inhibitors (MAOIs), such as Tranylcypromine, Phenelzine, and Isocarboxazid.

Heterocyclics, such as Amoxipine, Maprotiline and Trazodone.

others such as Venlafaxine, Nefazodone and Mirtazapine.

k. Agents for the Treatment of Incontinence

Anticholinergic agents such as propantheline.

Antispasmodic medications such as oxybutynin, tolterodine, and flavoxate.

Tricyclic antidepressants such as imipramine, and doxepin.

Calcium channel blockers such as tolterodine.

Beta agonists such as terbutaline.

l. AntiParkinson's Agents

Deprenyl, Amantadine, Levodopa, and Carbidopa.

m. Agents for the Treatment of Cardiac Disorders

Nitrates, beta-adrenergic blockers, calcium channel antagonists, ACE inhibitors, non-peptide angiotension II antagonists, IIb/IIIa antagonists, and aspirin.

Pharmaceutical kits useful in, for example, the treatment of pain, which comprise a therapeutically effective amount of a compound of the invention and/or opioid and/or other therapeutic compounds described herein, in one or more sterile containers, are also within the ambit of the present invention. Sterilization of the container may be carried out using conventional sterilization methodology well known to those skilled in the art. The sterile containers of materials may comprise separate containers, or one or more multi-part containers, as exemplified by the UNIVIAL™ two-part container (available from Abbott Labs, Chicago, Ill.), as desired. The compound of the invention and/or opioid and/or other therapeutic compound as described herein may be separate, or combined into a single dosage form as described above. Such kits may further include, if desired, one or more of various conventional pharmaceutical kit components, such as for example, one or more pharmaceutically acceptable carriers, additional vials for mixing the components, etc., as will be readily apparent to those skilled in the art. Instructions, either as inserts or as labels, indicating quantities of the components to be administered, guidelines for administration, and/or guidelines for mixing the components, may also be included in the kit.

In certain embodiments, the pharmaceutical compositions may further comprise an effective amount of at least one of the group consisting of: an opioid, an agent for the treatment of neuralgia/neuropathic pain, an agent for the treatment of depression, an agent for the treatment of incontinence, an anti-Parkinson's agent, and an agent for the treatment of cardiac disorders. Even more preferably, the pharmaceutical compositions may further comprise an antibiotic, antiviral, antifungal, anti-inflammatory, anesthetic, or mixture thereof.

In certain aspects, the compounds of the invention are ligands of the δ-opioid receptor. As such, the invention, in part, is directed to methods of binding opioid receptors, preferably δ-opioid receptors, in a patient in need thereof, comprising the step of administering to said patient an effective amount of a compound of the invention including, for example, a compound of formula I, II, III, IV, and/or V. The δ-opioid receptors may be located in the central nervous system or located peripherally to the central nervous system. In certain preferred embodiments, the binding of the present compounds modulates the activity, preferably as an agonist, of said opioid receptors. In certain preferred embodiments, the compound of formula I, II, III, IV, or V does not substantially cross the blood-brain barrier. Preferably, the compounds of the present invention are peripherally selective.

The spirocyclic heterocyclic derivatives of the present invention and pharmaceutical compositions containing these compounds may be utilized in a number of ways. In certain embodiments, the spirocyclic heterocyclic derivatives are ligands of the δ-opioid receptor and are useful, inter alia, in methods for treating pain, gastrointestinal dysfunction, urogenital tract disorders including incontinence, for example, stress urinary incontinence, urge urinary incontinence and benign prostatic hyperplasia, and overactive bladder disorder (see, e.g., R. B. Moreland et al., *Perspectives in Pharmacology*, Vol. 308(3), pp. 797-804 (2004) and M. O. Fraser, *Annual Reports in Medicinal Chemistry*, Chapter 6, pp. 51-60 (2003), the disclosures of which are hereby incorporated herein by reference, in their entireties), immunomodulatory disorders, inflammatory disorders, respiratory function disorders, depression, anxiety, attention deficit hyperactivity disorder, mood disorders, stress-related disorders, sympathetic nervous system disorder, tussis, motor disorder, traumatic injury to the central nervous system, stroke, cardiac arrhythmia, glaucoma, sexual dysfunction, shock, brain edema, cerebral ischemia, cerebral deficits subsequent to cardiac bypass surgery and grafting, systemic lupus erythematosus, Hodgkin's disease, Sjogren's disease, epilepsy, and rejection in organ transplants and skin grafts, and substance addiction. In certain other embodiments, the spirocyclic heterocyclic derivatives are ligands of the δ-opioid receptor and are useful, inter alia, in methods for providing cardioprotection, in methods for reducing the need for anesthesia, in methods for providing and maintaining an anesthetic state, in methods for improving organ and cell survival, and in methods of detecting, imaging, or monitoring degeneration or dysfunction of opioid receptors in a patient.

Compounds of the invention may be useful as analgesic agents for use during general anesthesia and monitored anesthesia care. Combinations of agents with different properties are often used to achieve a balance of effects needed to maintain the anesthetic state (e.g., amnesia, analgesia, muscle relaxation and sedation). Included in this combination are inhaled anesthetics, hypnotics, anxiolytics, neuromuscular blockers and opioids.

Thus, in accordance with preferred aspects of the invention, there are provided methods of treating pain, comprising the step of administering to a patient an effective amount of a compound of the invention including, for example, a compound of formula I, II, III, IV, and/or V. In certain preferred embodiments, the method further comprises administering to the patient an effective amount of an opioid, the opioid preferably selected from the group consisting of: alfentanil, allylprodine, alphaprodine, anileridine, benzyl-morphine, bezitramide, buprenorphine, butorphanol, clonitazene, codeine, cyclazocine, desomorphine, dextromoramide, dezocine, diampromide, diamorphone, dihydrocodeine, dihydromorphine, dimenoxadol, dimepheptanol, dimethylthiambutene, dioaphetylbutyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levallorphan, levorphanol, levophenacylmorphan, lofentanil, loperamide, meperidine, meptazinol, metazocine, methadone, metopon, morphine, myrophine, nalbuphine, narceine, nicomorphine, norlevorphanol, normethadone, nalorphine, normorphine, norpinanone, opium, oxycodone, oxymorphone, papaveretum, pentazocine, phenadoxone, phenomorphan, phanazocine, phenoperidine, piminodine, piritramide, propheptazine, promedol, properidine, propiram, propoxyphene, sulfentanil, tilidine, and tramadol, or a mixture thereof.

In other preferred aspects of the invention, there are provided methods of treating gastrointestinal dysfunction, comprising the step of administering to a patient an effective amount of a compound of the invention including, for example, a compound of formula I, II, III, IV, and/or V.

In some preferred aspects of the invention, there are provided methods of treating a urogenital tract disorder, the urogenital tract disorder preferably selected from overactive bladder and incontinence, wherein the incontinence is preferably stress urinary or urge urinary incontinence, more preferably overactive bladder, comprising the step of administering to a patient an effective amount of a compound of the invention including, for example, a compound of formula I, II, III, IV, and/or V. Thus, in some preferred methods of treating urogenital tract disorder, the method further comprises administering to the patient an effective amount of an agent for the treatment of incontinence.

In certain preferred aspects of the invention, there are provided methods of treating an immunomodulatory disorder, the immunomodulatory disorder preferably selected from the group consisting of an autoimmune disease, a collagen disease, an allergy, a side effect associated with the administration of an anti-tumor agent, and a side effect associated with the administration of an antiviral agent, comprising the step of administering to a patient an effective amount of a compound of the invention including, for example, a compound of formula I, II, III, IV, and/or V. Thus, in some preferred methods of treating an immunomodulatory disorder, the autoimmune disease treated is selected from the group consisting of arthritis, an autoimmune disorder associated with a skin graft, an autoimmune disorder associated with organ transplant, and an autoimmune disorder associated with surgery.

In certain other preferred aspects of the invention, there are provided methods of treating an inflammatory disorder, the inflammatory disorder preferably selected from the group consisting of arthritis, psoriasis, asthma, or inflammatory bowel disease, comprising the step of administering to a patient an effective amount of a compound of the invention including, for example, a compound of formula I, II, III, IV, and/or V.

In yet other preferred aspects of the invention, there are provided methods of treating a respiratory function disorder, the respiratory function disorder preferably selected from the group consisting of asthma and lung edema, comprising the step of administering to a patient an effective amount of a compound of the invention including, for example, a compound of formula I, II, III, IV, and/or V.

In certain other preferred aspects of the invention, there are provided methods of treating anxiety, comprising the step of administering to a patient an effective amount of a compound of the invention including, for example, a compound of formula I, II, III, IV, and/or V.

In certain other preferred aspects of the invention, there are provided methods of treating a mood disorder, wherein the mood disorder is preferably selected from the group consisting of depression, bipolar manic-depression, and seasonal affective disorder, comprising the step of administering to a patient an effective amount of a compound of the invention including, for example, a compound of formula I, II, III, IV, and/or V. In certain of the methods herein provided for treating a mood disorder, the method further comprises the step of administering to said patient an effective amount of an agent for the treatment of depression.

In certain other preferred aspects of the invention, there are provided methods of treating a stress-related disorder, wherein the stress-related disorder is preferably selected from the group consisting of post-traumatic stress disorder, panic disorder, generalized anxiety disorder, social phobia, and obsessive-compulsive disorder, comprising the step of administering to a patient an effective amount of a compound of the invention including, for example, a compound of formula I, II, III, IV, and/or V.

In certain other preferred aspects of the invention, there are provided methods of treating attention deficit hyperactivity disorder, comprising the step of administering to a patient an effective amount of a compound of the invention including, for example, a compound of formula I, II, III, IV, and/or V.

In certain other preferred aspects of the invention, there are provided methods of treating a sympathetic nervous system disorder, preferably hypertension, comprising the step of administering to a patient an effective amount of a compound of the invention including, for example, a compound of formula I, II, III, IV, and/or V.

In certain other preferred aspects of the invention, there are provided methods of treating tussis, comprising the step of administering to a patient an effective amount of a compound of the invention including, for example, a compound of formula I, II, III, IV, and/or V.

In certain other preferred aspects of the invention, there are provided methods of treating a motor disorder, wherein the motor disorder is preferably selected from the group consisting of tremors, Parkinson's disease, Tourette's syndrome, and dyskenesia, more preferably tremors, comprising the step of administering to a patient an effective amount of a compound of the invention including, for example, a compound of formula I, II, III, IV, and/or V. In certain methods of treating tremors, the method further comprises the step of administering to said patient an effective amount of an anti-Parkinson's agent.

In certain other preferred aspects of the invention, there are provided methods of treating a traumatic injury to the central nervous system, wherein the traumatic injury to the central nervous system is preferably selected from the group consisting of a traumatic injury to the spinal cord or brain, comprising the step of administering to a patient an effective amount of a compound of the invention including, for example, a compound of formula I, II, III, IV, and/or V.

In certain other preferred aspects of the invention, there are provided methods of treating a stroke, comprising the step of administering to a patient an effective amount of a compound of the invention including, for example, a compound of formula I, II, III, IV, and/or V.

In certain other preferred aspects of the invention, there are provided methods of treating a cardiac arrhythmia, comprising the step of administering to a patient an effective amount of a compound of the invention including, for example, a compound of formula I, II, III, IV, and/or V.

In certain other preferred aspects of the invention, there are provided methods of treating glaucoma, comprising the step of administering to a patient an effective amount of a compound of the invention including, for example, a compound of formula I, II, III, IV, and/or V.

In certain other preferred aspects of the invention, there are provided methods of treating sexual dysfunction, wherein the sexual dysfunction is preferably premature ejaculation, comprising the step of administering to a patient an effective amount of a compound of the invention including, for example, a compound of formula I, II, III, IV, and/or V.

In certain other preferred aspects of the invention, there are provided methods of treating substance addiction, wherein the substance addiction is preferably alcohol addiction, nicotine addiction, or drug addiction, more preferably drug addiction, especially where the drugs are opioids, comprising the step of administering to a patient an effective amount of a compound of the invention including, for example, a compound of formula I, II, III, IV, and/or V.

In certain other preferred aspects of the invention, there are provided methods of treating a condition selected from the group consisting of shock, brain edema, cerebral ischemia, cerebral deficits subsequent to cardiac bypass surgery and grafting, systemic lupus erythematosus, Hodgkin's disease, Sjogren's disease, epilepsy, and rejection in organ transplants and skin grafts, comprising the step of administering to a patient an effective amount of a compound of the invention including, for example, a compound of formula I, II, III, IV, and/or V.

In certain other preferred aspects of the invention, there are provided methods for improving organ and cell survival, comprising the step of administering to a patient an effective amount of a compound of the invention including, for example, a compound of formula I, II, III, IV, and/or V.

Techniques for evaluating and/or employing the present compounds in methods for improving organ and cell survival and organ preservation are described, for example, in C. V. Borlongan et al., *Frontiers in Bioscience* (2004), 9(Suppl.), 3392-3398, Su, *Journal of Biomedical Science* (Basel) (2000), 7(3), 195-199, and U.S. Pat. No. 5,656,420, the disclosures of each of which are hereby incorporated herein by reference in their entireties.

In certain other preferred aspects of the invention, there are provided methods for providing cardioprotection, comprising the step of administering to a patient an effective amount of a compound of the invention including, for example, a compound of formula I, II, III, IV, and/or V. In preferred form, the methods may be used in the treatment of ischemic damage.

Accordingly, the methods and compositions of the present invention may be employed to protect against ischemia and reperfusion injuries.

In connection with preferred embodiments, the compound of the invention may be administered prior to, during, or after the ischemic event. In embodiments involving patients who are to undergo heart surgery, the compound of the invention may preferably be administered before the surgery. Also in certain preferred embodiments, the methods may further comprise the co-administration of an agent for treating a cardiac disorder.

Techniques for evaluating and/or employing the present compounds in methods for providing cardioprotection are described, for example, in Watson, et al., *J. Pharm. Exp. Ther.* 316: 423-430 (2006), WO 2004/060321 A2 and WO 99/04795, the disclosures of each of which are hereby incorporated herein by reference in their entireties.

In certain other preferred aspects of the invention, there are provided methods for reducing the need for anesthesia, comprising the step of administering to a patient an effective amount of a compound of the invention including, for example, a compound of formula I, II, III, IV, and/or V.

In certain other preferred aspects of the invention, there are provided methods for producing or maintaining an anesthetic state, comprising the step of administering to a patient an effective amount of a compound of the invention including, for example, a compound of formula I, II, III, IV, and/or V. In some more preferred embodiments, the method further comprises administering to the patient an anesthetic agent selected from the group consisting of an inhaled anesthetic, an hypnotic, an anxiolytic, a neuromuscular blocker, and an opioid, with co-administration of the anesthetic agent and the compound of the invention being even more preferred.

Additional diseases and/or disorders which may be treated with the compounds and pharmaceutical compositions of the present invention include those described, for example, in WO2004/062562 A2, WO 2004/063157 A1, WO 2004/063193 A1, WO 2004/041801 A1, WO 2004/041784 A1, WO 2004/041800 A1, WO 2004/060321 A2, WO 2004/035541 A1, WO 2004/035574 A2, WO 2004/041802 A1, US 2004082612 A1, WO 2004026819 A2, WO 2003057223 A1, WO 2003037342 A1, WO 2002094812 A1, WO 2002094810 A1, WO 2002094794 A1, WO 2002094786 A1, WO 2002094785 A1, WO 2002094784 A1, WO 2002094782 A1, WO 2002094783 A1, WO 2002094811 A1, the disclosures of each of which are hereby incorporated herein by reference in their entireties.

In certain aspects, the present invention is directed to radio-labeled derivatives and isotopically labeled derivatives of compounds of the invention including, for example, compounds of formula I, II, III, IV, and/or V. Suitable labels include, for example, $^2H$, $^3H$, $^{11}C$, $^{13}C$, $^{13}N$, $^{15}N$, $^{15}O$, $^{18}O$, $^{18}F$ and $^{34}S$. Such labeled derivatives may be useful for biological studies and/or diagnostic imaging including, for example, using positron emission tomography, for metabolite identification studies and the like. Such diagnostic imaging methods may comprise, for example, administering to a patient a radiolabeled derivative or isotopically labeled derivative of a compound of the invention including, for example a compound of formula I, II, III, IV, and/or V, and imaging the patient, for example, by application of suitable energy, such as in positron emission tomography. Isotopically- and radio-labeled derivatives may be prepared utilizing techniques well known to the ordinarily skilled artisan.

The present invention will now be illustrated by reference to the following specific, non-limiting examples. Those skilled in the art of organic synthesis may be aware of still other synthetic routes to the invention compounds. The reagents and intermediates used herein are commercially available or may be prepared according to standard literature procedures.

Methods of Preparation

The synthesis of compounds 1A-1E is outlined in Scheme 1. Palladium catalyzed Negishi-type coupling of 1.1 [Dolle, R. E.; et al., WO2005033073] with zinc bromide reagents 1.2 or 1.3, conducted in tetrahydrofuran using tetrakistriphenylphosphine palladium (0) as catalyst, provided the methyl esters 1.4a and 1.4b, respectively. The esters 1.4a and 1.4b were hydrolyzed under basic conditions to give carboxylic acid derivatives 1.5a and 1.5b, respectively. Coupling of carboxylic acid derivatives 1.5a and 1.5b with diethylamine (1.6) using O-benzotriazol-1-yl-N,N,N',N'-tetramethyluronium tetrafluoroborate (TBTU) as coupling agent afforded tertiary amides 1.7a and 1.7b, respectively. Treatment of the Boc derivatives 1.7a, 1.7b and 1.4b with hydrochloric acid provided the final compounds 1A, 1B, and 1E, respectively. Palladium catalyzed hydrogenation of 1A and 1B provided the compounds 1C and 1D, respectively.

Scheme 1:

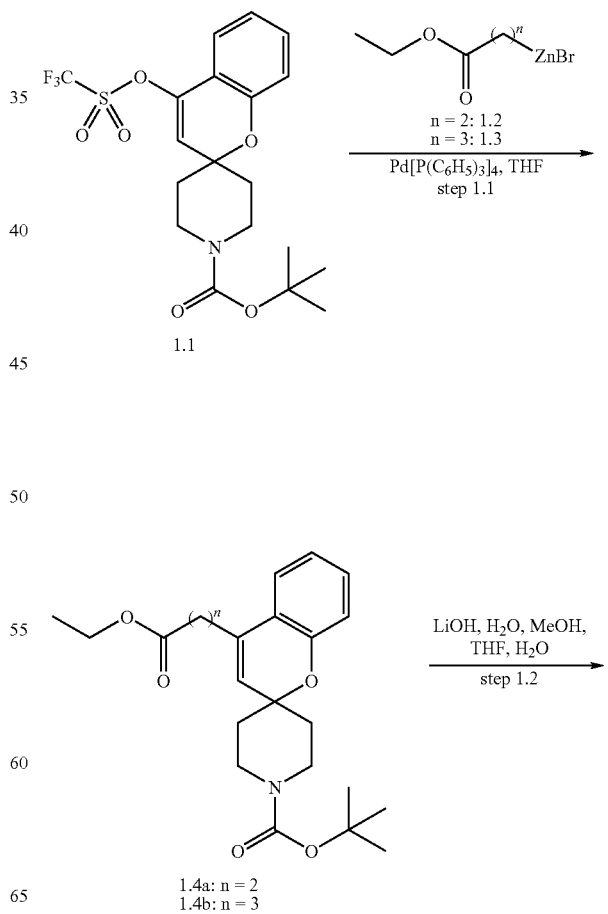

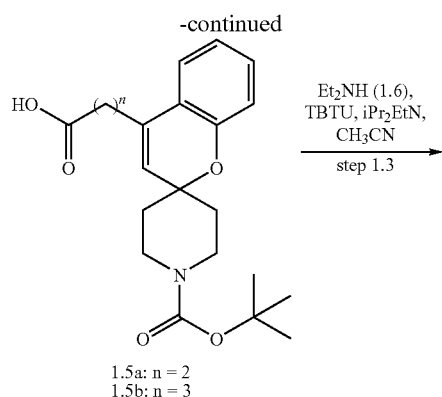

1.5a: n = 2
1.5b: n = 3

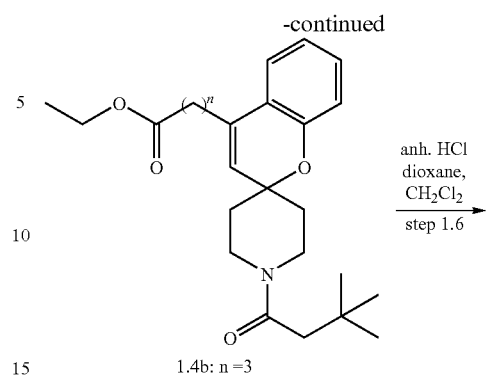

1.4b: n = 3

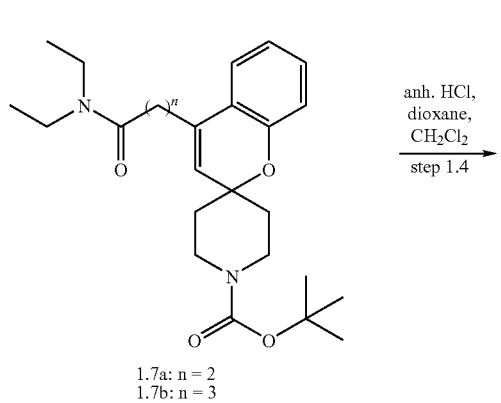

1.7a: n = 2
1.7b: n = 3

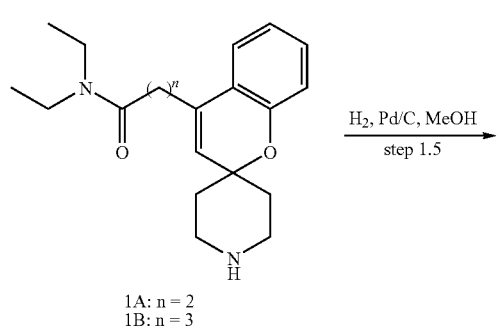

1A: n = 2
1B: n = 3

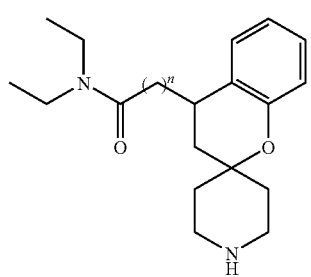

1E

The synthesis of compounds 2A-2G is outlined in Scheme 2. Palladium catalyzed hydrogenation of 1.4b provided the provided the ester 2.1. The ester 2.1 was hydrolyzed under basic conditions to give the carboxylic acid derivative 2.2. Coupling of the carboxylic acid 2.2 with the amines 2.3a, 2.3b, 2.3c or 2.3d, using 2-chloro-1-methylpyridinium iodide (Mukaiyama acylating reagent) as coupling agent afforded the corresponding aminocarbonyl derivatives 2.5, which were converted to the compounds 2A-D under acidic conditions. Palladium catalyzed Negishi-type coupling of 1.1 with zinc bromide reagent 2.6, conducted in tetrahydrofuran using tetrakistriphenylphosphine palladium (0) as catalyst, provided the ester 2.7, which was converted to 2.8 by hydrogenation. The ester 2.8 was hydrolyzed under basic conditions to give the carboxylic acid derivative 2.9. Coupling of the carboxylic acid 2.9 with diethylamine (1.6), using 2-chloro-1-methylpyridinium iodide (Mukaiyama acylating reagent) as coupling agent afforded the corresponding aminocarbonyl derivative 2.10, which was converted to the compound 2E under acidic conditions. Palladium catalyzed Negishi-type coupling of 1.1 with zinc bromide reagent 2.11, conducted in tetrahydrofuran using tetrakistriphenylphosphinepalladium (0) as catalyst, provided the ester 2.12, which was converted to 2.13 by hydrogenation. The ester 2.13 was hydrolyzed under basic conditions to give the carboxylic acid derivative 2.14. Coupling of the carboxylic acid 2.14 with the amines 1.6 or 2.3a, using 2-chloro-1-methylpyridinium iodide (Mukaiyama acylating reagent) as coupling agent afforded the corresponding aminocarbonyl derivatives 2.15, which were converted to the compounds 2F-G, respectively, under acidic conditions.

Scheme 2
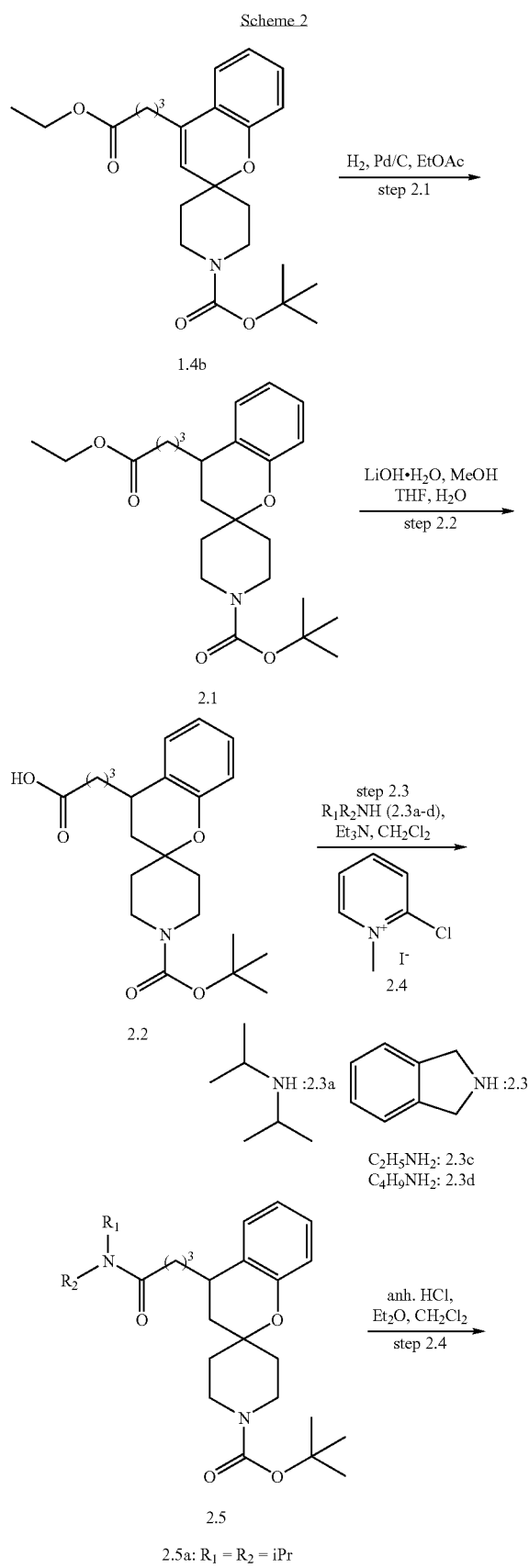
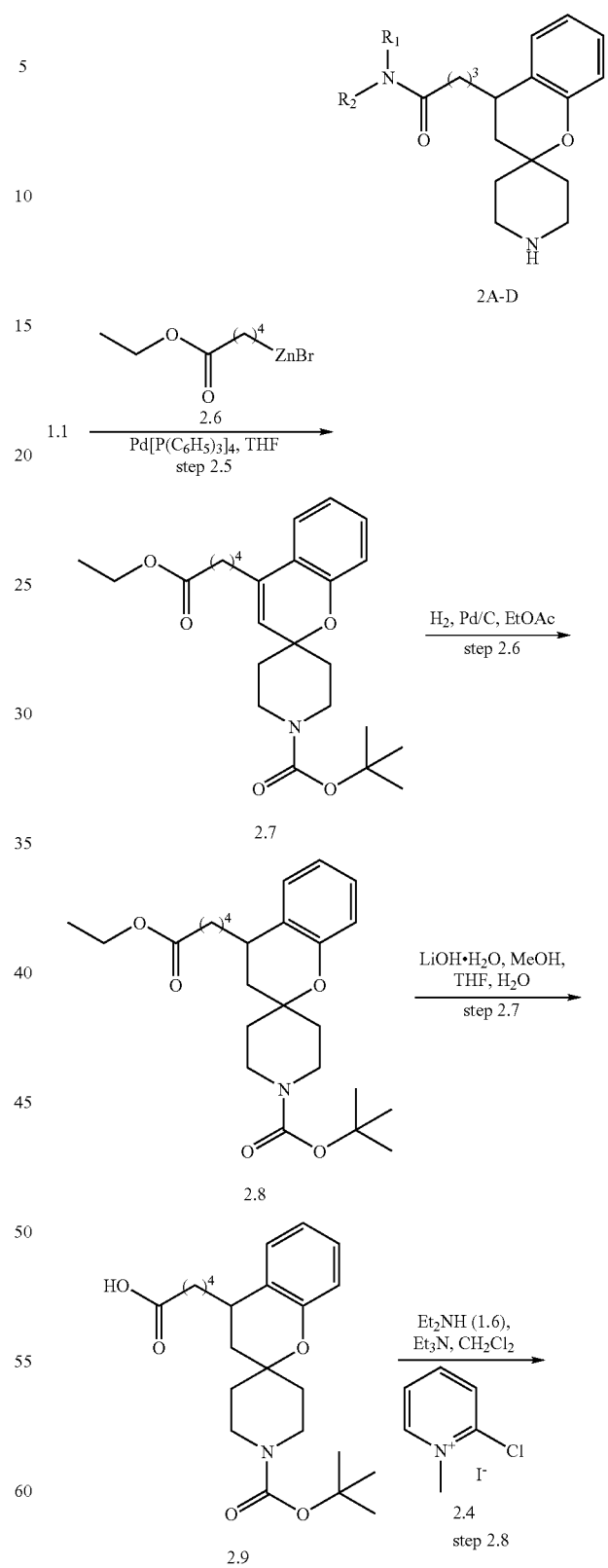
2.5a: R₁ = R₂ = iPr

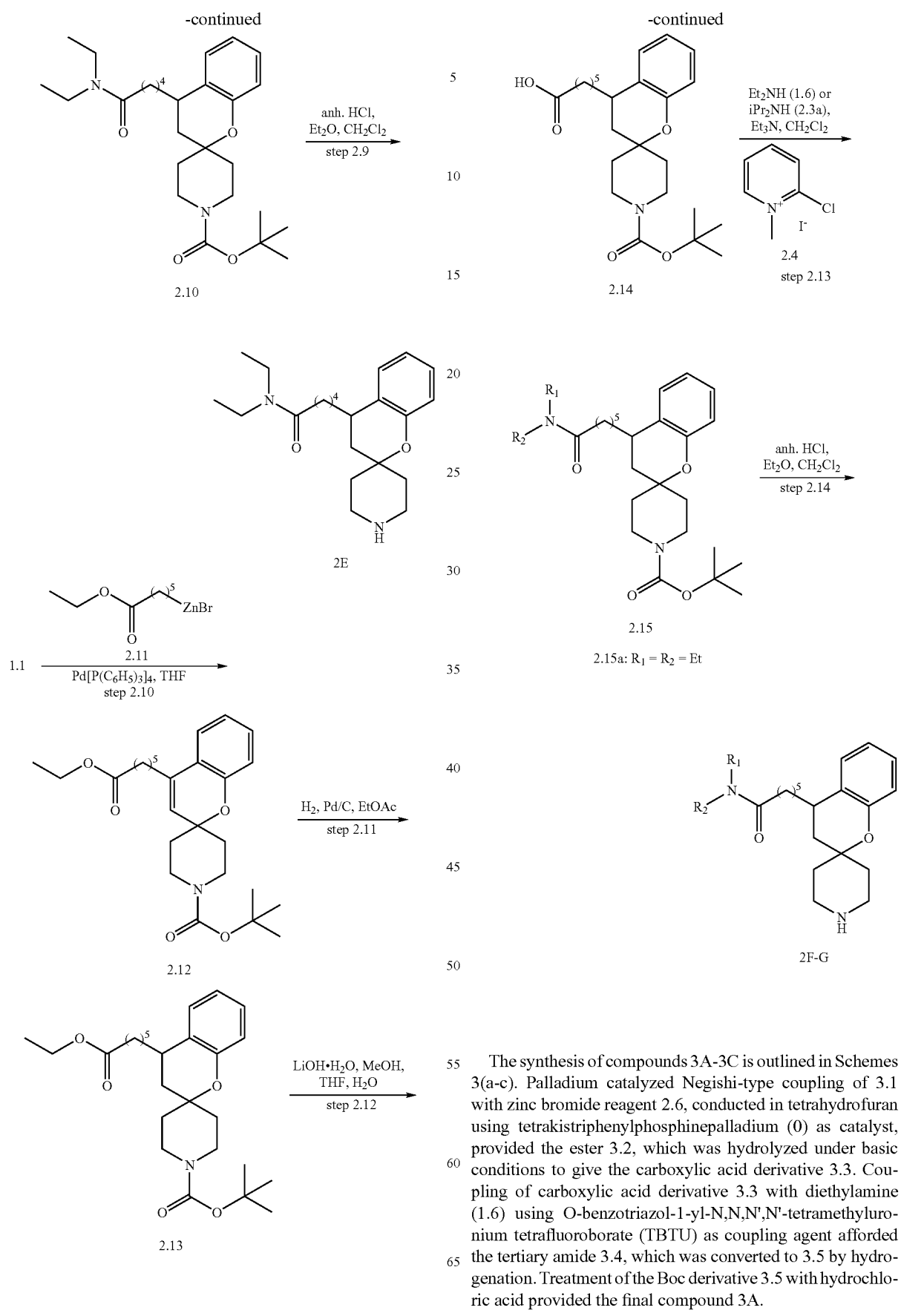

The synthesis of compounds 3A-3C is outlined in Schemes 3(a-c). Palladium catalyzed Negishi-type coupling of 3.1 with zinc bromide reagent 2.6, conducted in tetrahydrofuran using tetrakistriphenylphosphinepalladium (0) as catalyst, provided the ester 3.2, which was hydrolyzed under basic conditions to give the carboxylic acid derivative 3.3. Coupling of carboxylic acid derivative 3.3 with diethylamine (1.6) using O-benzotriazol-1-yl-N,N,N',N'-tetramethyluronium tetrafluoroborate (TBTU) as coupling agent afforded the tertiary amide 3.4, which was converted to 3.5 by hydrogenation. Treatment of the Boc derivative 3.5 with hydrochloric acid provided the final compound 3A.

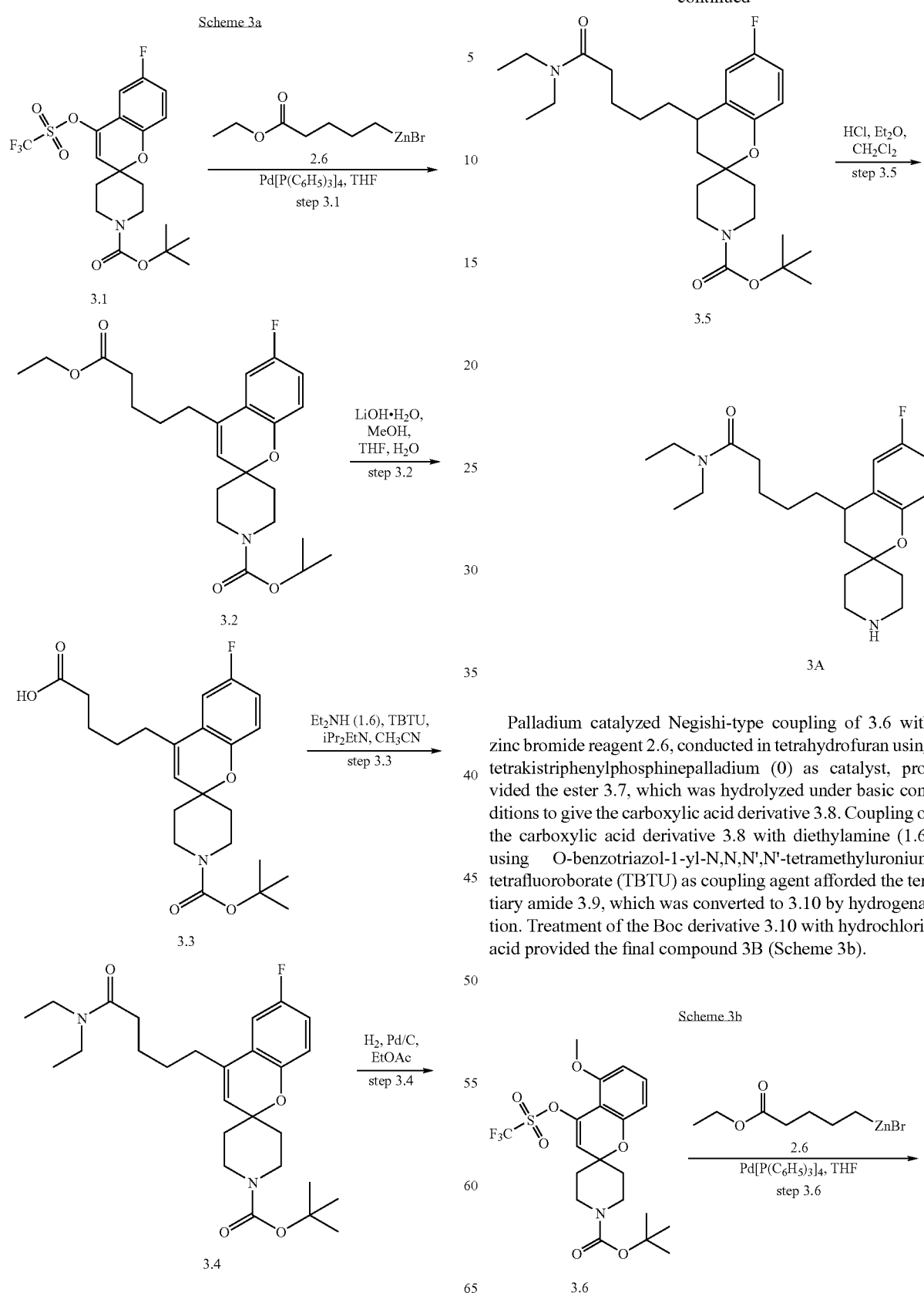

Palladium catalyzed Negishi-type coupling of 3.6 with zinc bromide reagent 2.6, conducted in tetrahydrofuran using tetrakistriphenylphosphinepalladium (0) as catalyst, provided the ester 3.7, which was hydrolyzed under basic conditions to give the carboxylic acid derivative 3.8. Coupling of the carboxylic acid derivative 3.8 with diethylamine (1.6) using O-benzotriazol-1-yl-N,N,N',N'-tetramethyluronium tetrafluoroborate (TBTU) as coupling agent afforded the tertiary amide 3.9, which was converted to 3.10 by hydrogenation. Treatment of the Boc derivative 3.10 with hydrochloric acid provided the final compound 3B (Scheme 3b).

-continued

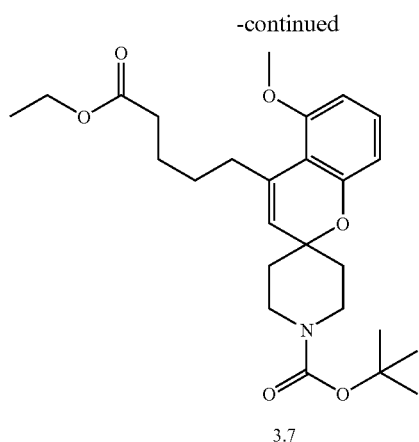

3.7

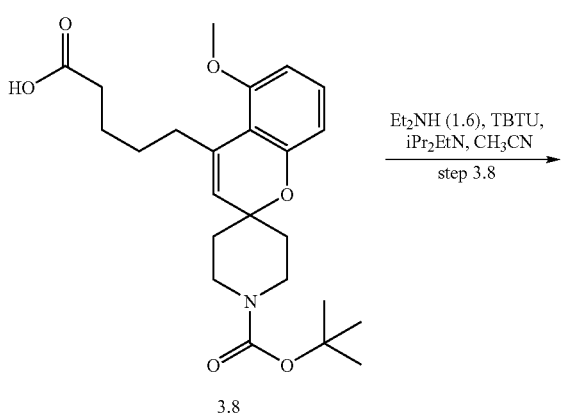

3.8

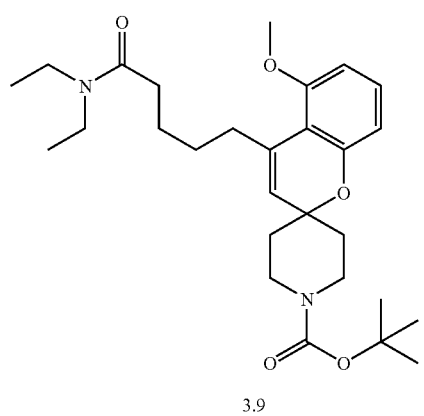

3.9

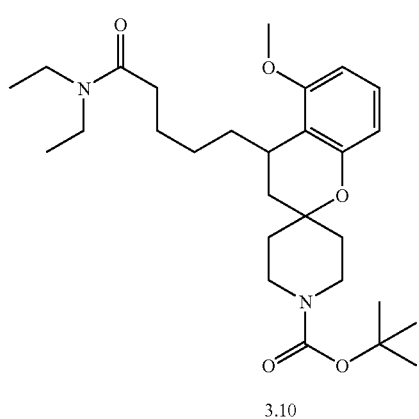

3.10

-continued

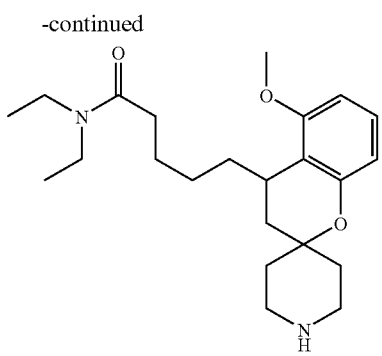

3B

Palladium catalyzed Negishi-type coupling of 3.11 with zinc bromide reagent 2.6, conducted in tetrahydrofuran using tetrakistriphenylphosphinepalladium (0) as catalyst, provided the ethyl ester 3.12, which was hydrolyzed under basic conditions to give the carboxylic acid derivative 3.13. Coupling of carboxylic acid derivative 3.13 with diethylamine (1.6) using O-benzotriazol-1-yl-N,N,N',N'-tetramethyluronium tetrafluoroborate (TBTU) as coupling agent afforded the tertiary amide 3.14, which was converted to 3.15 by hydrogenation. Treatment of the N-Boc, O-MOM derivative 3.15 with hydrochloric acid provided the final compound 3C.

Scheme 3c

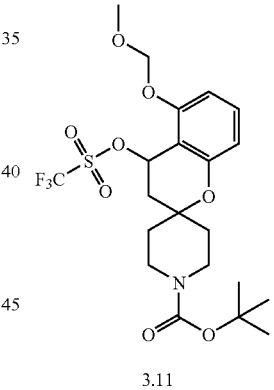

3.11

3.12

-continued

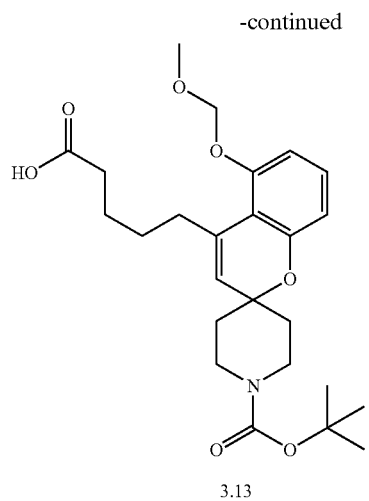

3.13

Et₂NH (1.6), TBTU,
iPr₂EtN, CH₃CN
─────────────→
step 3.13

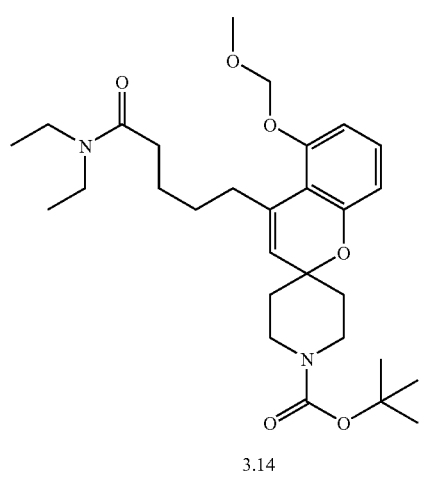

3.14

H₂, Pd/C,
MeOH
─────────→
step 3.14

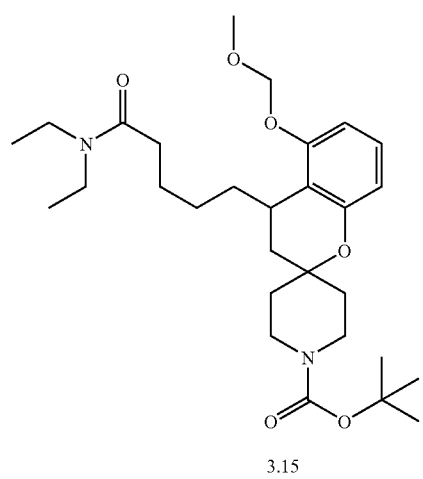

3.15

HCl, dioxane,
MeOH
─────────→
step 3.15

-continued

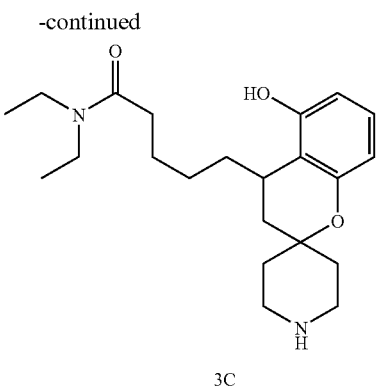

3C

The synthesis of compounds 4A-4E is outlined in Schemes 4(a-c). The Negishi coupling of the enol triflate 1.1 with zinc bromide reagent 4.1 in tetrahydrofuran in the presence of tetrakistriphenylphosphinepalladium (0) gave the nitrile 4.2, which was converted to 4.3 by hydrogenation. Treatment of 4.3 with borane-dimethyl sulfide complex afforded the primary amine 4.4. Coupling of 4.4 with diethylcarbamoyl chloride (4.5) afforded the urea 4.6, which was converted to 4A under acidic conditions.

Scheme 4a

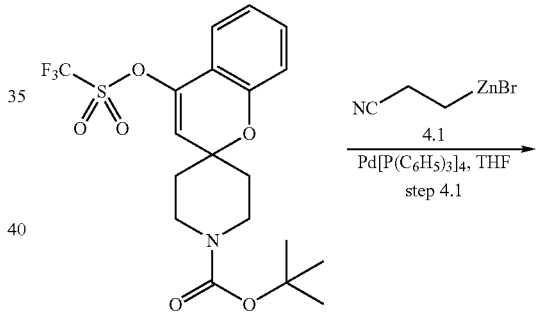

1.1        4.1

Pd[P(C₆H₅)₃]₄, THF
─────────────→
step 4.1

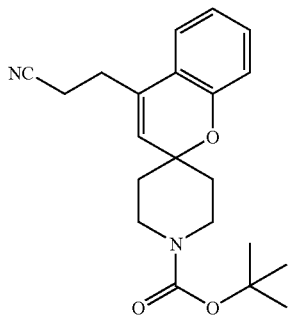

4.2

H₂, Pd/C, MeOH
─────────────→
step 4.2

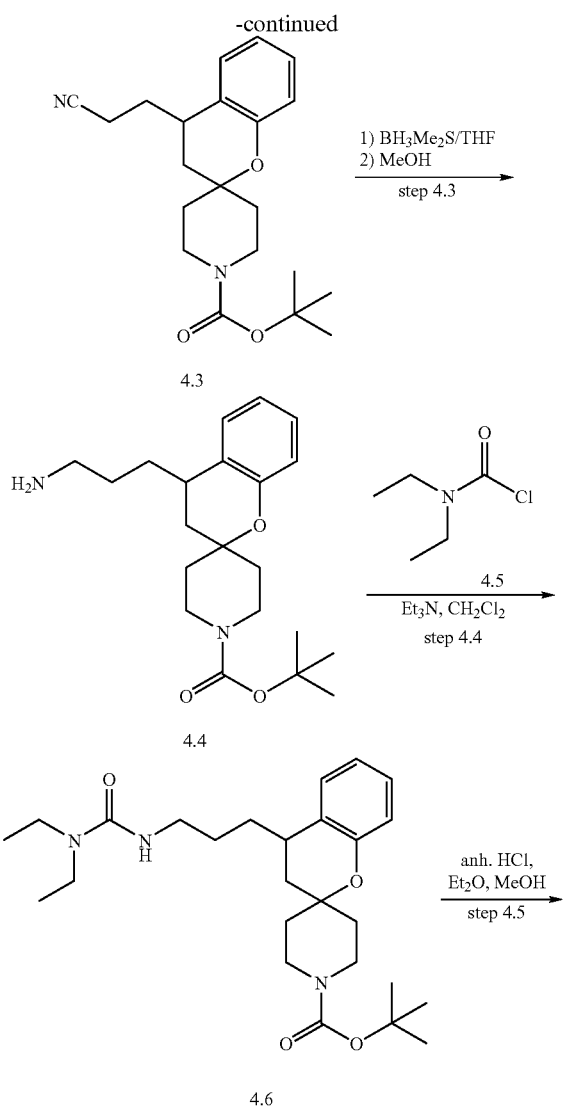
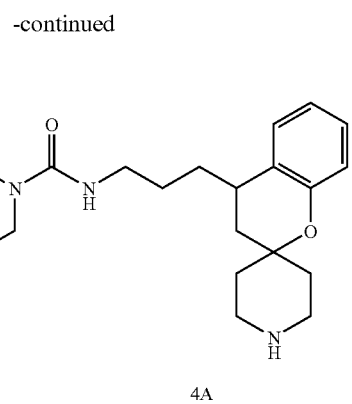

4A

Coupling of 4.4 with 2-ethylbutanoyl chloride (4.7) provided the amide 4.8, which was converted to 4B under acidic conditions. Treatment of 4.8 with methyl iodide (4.9) in the presence of sodium hydride afforded the tertiary amide derivative 4.10, which was converted to 4C under acidic condition. Coupling of 4.4 with ethanesulfonyl chloride (4.11) provided the sulfonamide 4.12, which was converted to 4D under acidic conditions. Treatment of 4.12 with methyl iodide (4.9) in the presence of sodium hydride afforded the tertiary sulfonamide derivative 4.13, which was converted to 4E under acidic condition.

Scheme 4b

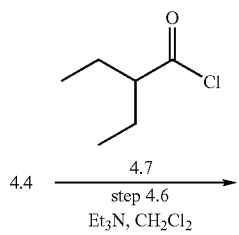

-continued
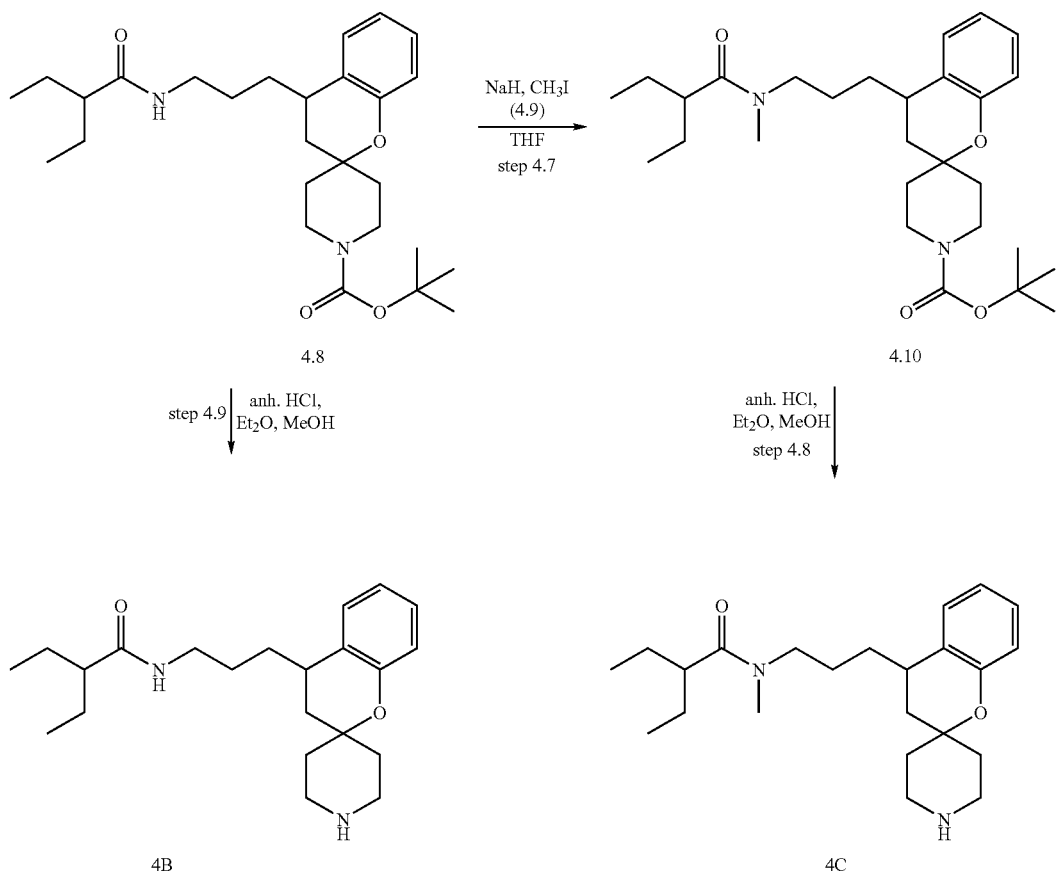
Scheme 4c
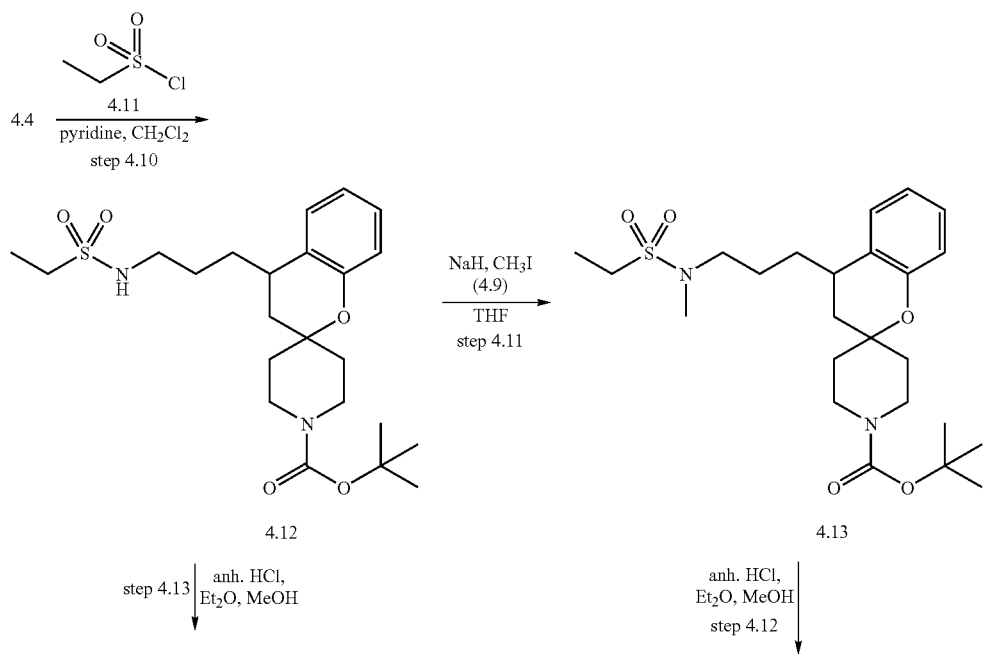

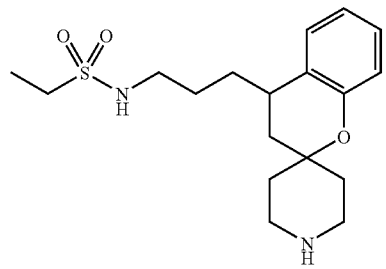

4D

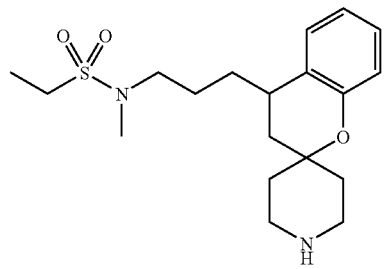

4E

The synthesis of compounds 5A and 5B is outlined in Schemes 5a and 5b. Wittig olefination of 5.1 with ethyl 2-(diethoxyphosphoryl)acetate (5.2) in the presence of sodium hydride, provided a mixture of the olefins 5.3, 5.4 and 5.5. Hydrogenation of this mixture provided the ethyl ester 5.6, which was hydrolyzed under basic conditions to give the carboxylic acid derivative 5.7. Coupling of the carboxylic acid derivative 5.7 with diethylamine (1.6) using O-benzotriazol-1-yl-N,N,N',N'-tetramethyluronium tetrafluoroborate (TBTU) as coupling agent afforded the tertiary amide 5.8, which was converted to 5A under acidic conditions. Coupling of the carboxylic acid derivative 5.7 with glycine methyl ester (5.9) using O-benzotriazol-1-yl-N,N,N',N'-tetramethyluronium tetrafluoroborate (TBTU) as coupling agent afforded the amide 5.10, which was hydrolyzed under basic conditions to give the carboxylic acid derivative 5.11. Coupling of 5.11 with diethylamine (1.6) provided the diethylcarboxamide derivative 5.12, which was converted to 5B under acidic conditions.

Scheme 5a

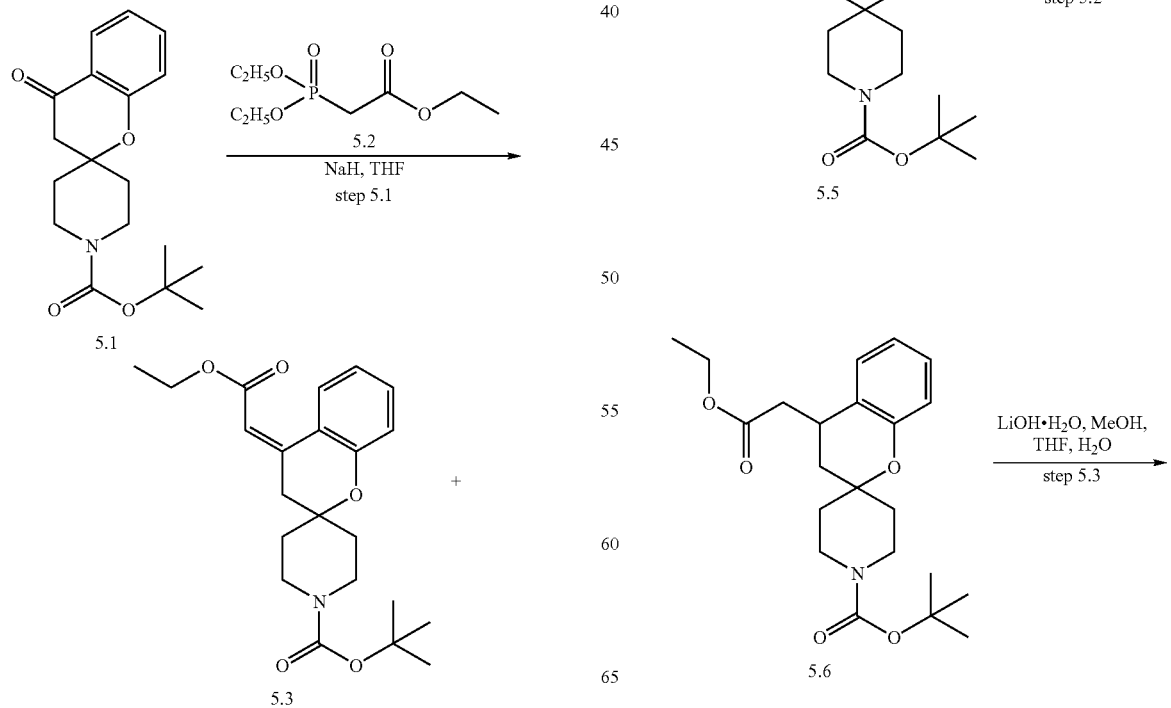

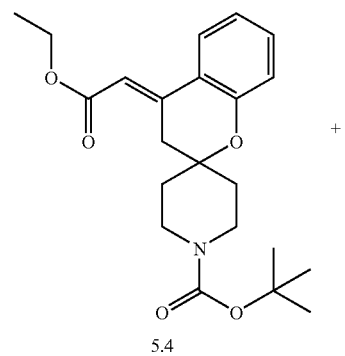

5.4

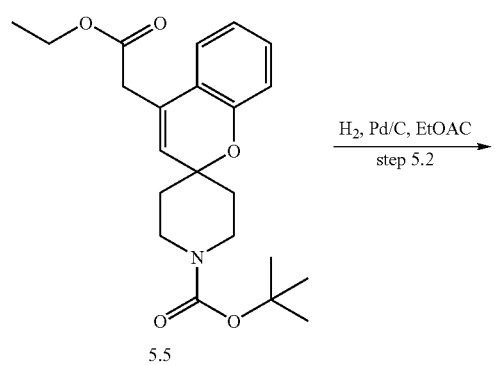

5.5

H$_2$, Pd/C, EtOAC
step 5.2

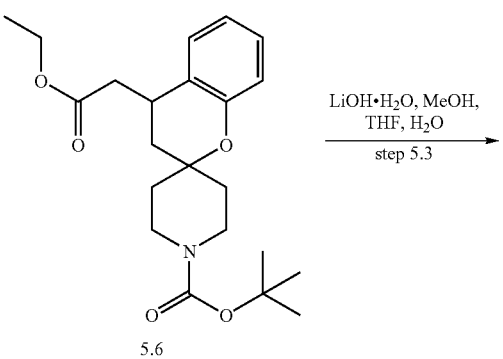

5.6

LiOH•H$_2$O, MeOH, THF, H$_2$O
step 5.3

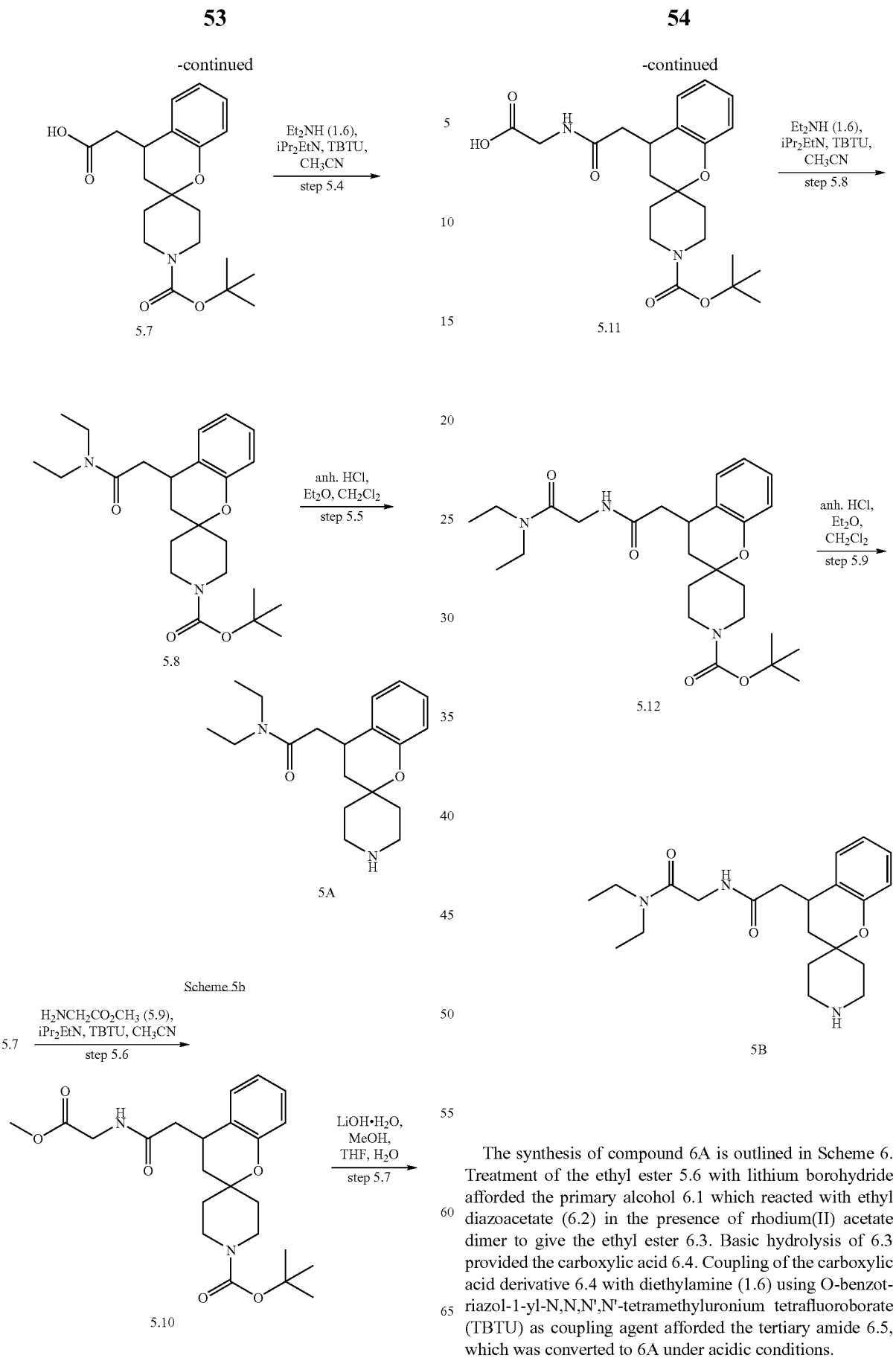

The synthesis of compound 6A is outlined in Scheme 6. Treatment of the ethyl ester 5.6 with lithium borohydride afforded the primary alcohol 6.1 which reacted with ethyl diazoacetate (6.2) in the presence of rhodium(II) acetate dimer to give the ethyl ester 6.3. Basic hydrolysis of 6.3 provided the carboxylic acid 6.4. Coupling of the carboxylic acid derivative 6.4 with diethylamine (1.6) using O-benzotriazol-1-yl-N,N,N',N'-tetramethyluronium tetrafluoroborate (TBTU) as coupling agent afforded the tertiary amide 6.5, which was converted to 6A under acidic conditions.

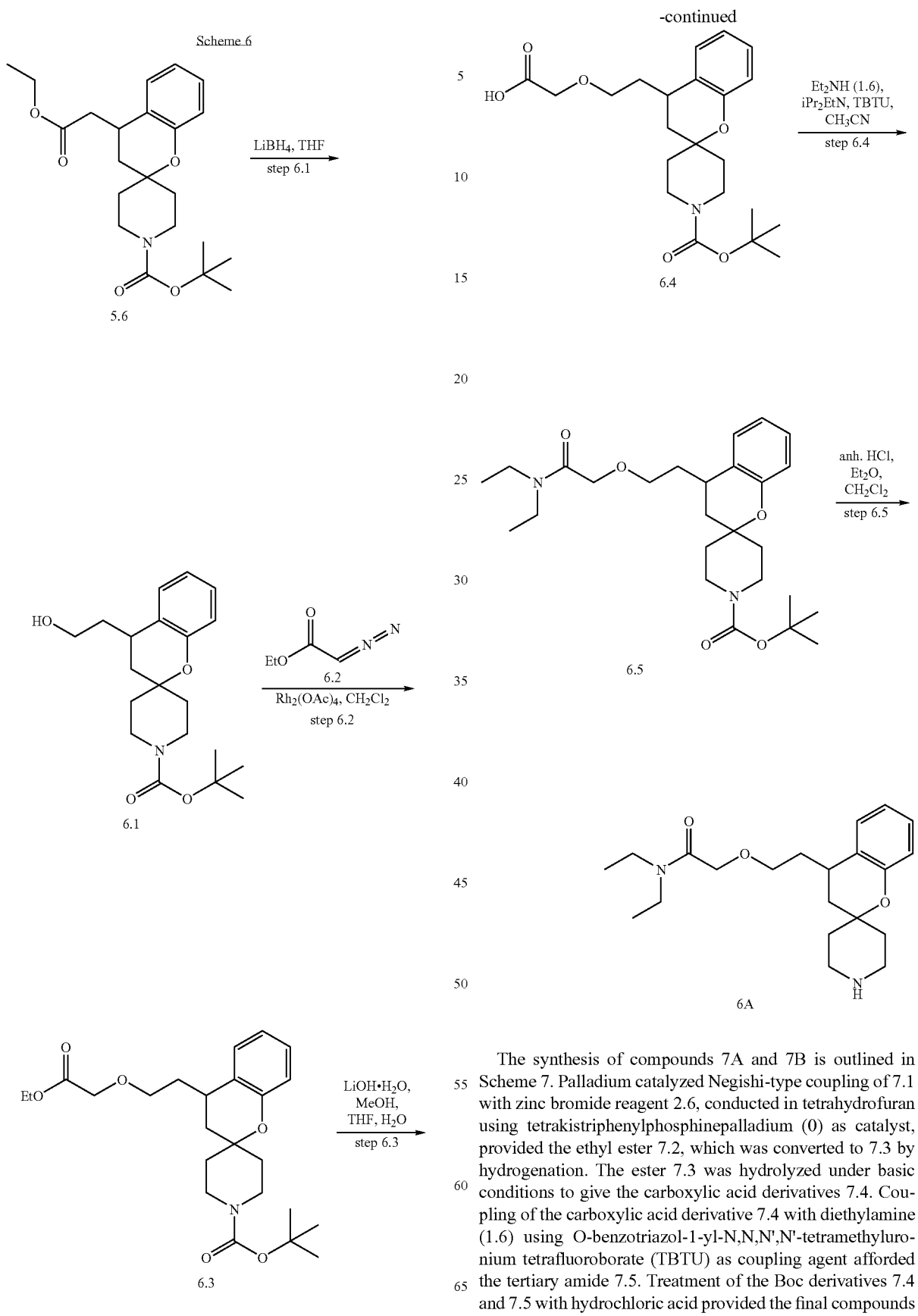

The synthesis of compounds 7A and 7B is outlined in Scheme 7. Palladium catalyzed Negishi-type coupling of 7.1 with zinc bromide reagent 2.6, conducted in tetrahydrofuran using tetrakistriphenylphosphinepalladium (0) as catalyst, provided the ethyl ester 7.2, which was converted to 7.3 by hydrogenation. The ester 7.3 was hydrolyzed under basic conditions to give the carboxylic acid derivatives 7.4. Coupling of the carboxylic acid derivative 7.4 with diethylamine (1.6) using O-benzotriazol-1-yl-N,N,N',N'-tetramethyluronium tetrafluoroborate (TBTU) as coupling agent afforded the tertiary amide 7.5. Treatment of the Boc derivatives 7.4 and 7.5 with hydrochloric acid provided the final compounds 7A and 7B, respectively.

Scheme 7:
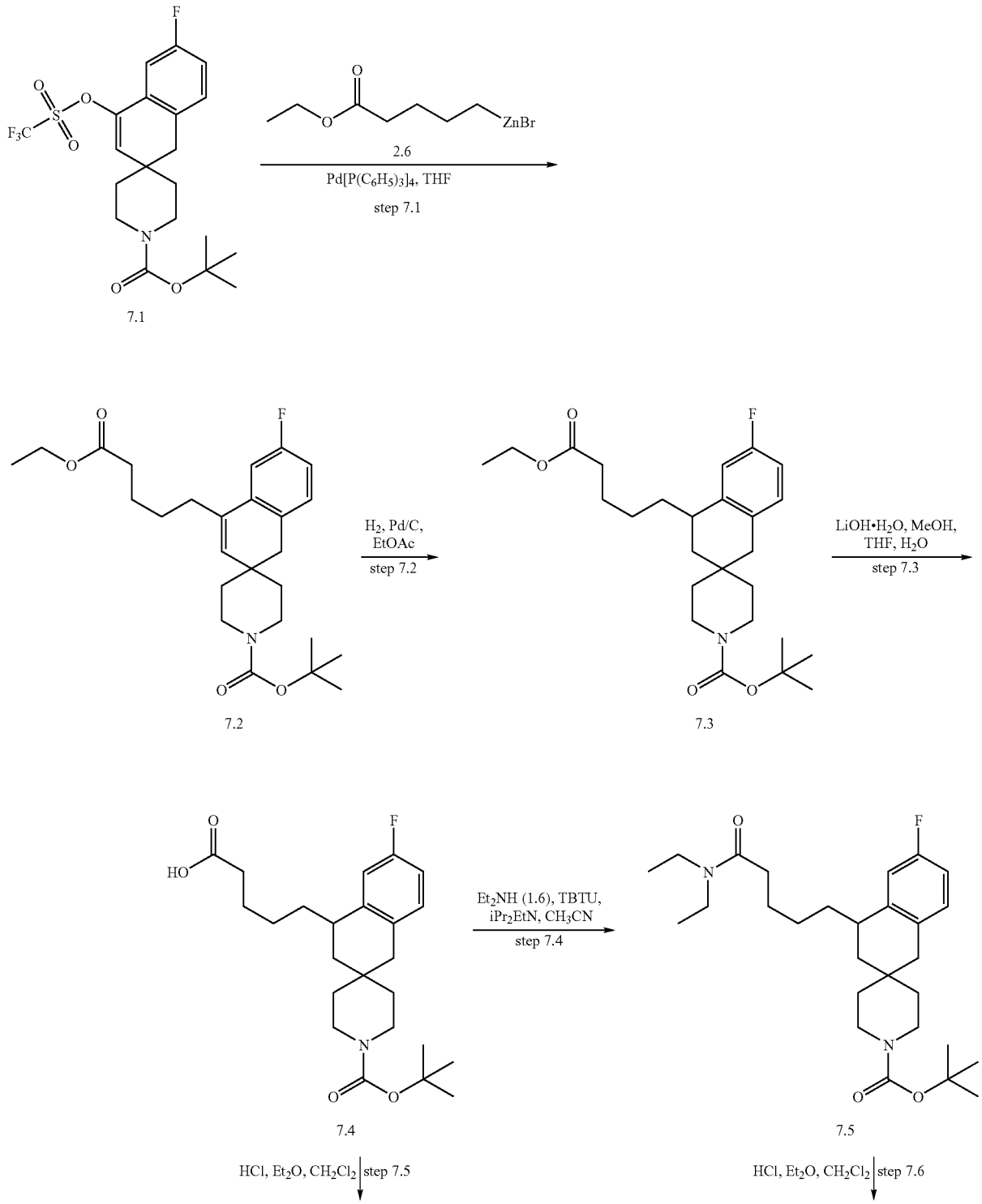

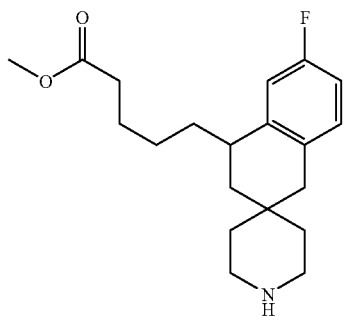

7A

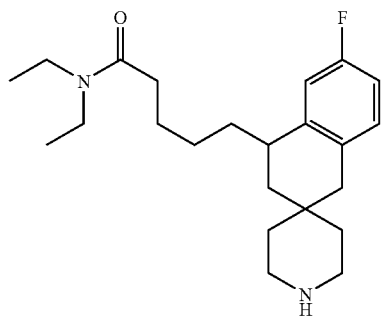

7B

-continued

The synthesis of compounds 8A-8C is outlined in Schemes 8a and 8b. Palladium catalyzed Negishi-type coupling of 8.1 with zinc bromide reagent 2.6, conducted in tetrahydrofuran using tetrakistriphenylphosphinepalladium (0) as catalyst, provided the ethyl ester 8.2, which was hydrolyzed under basic conditions to give the carboxylic acid derivative 8.3. Coupling of the carboxylic acid derivative 8.3 with diethylamine (1.6) using O-benzotriazol-1-yl-N,N,N',N'-tetramethyluronium tetrafluoroborate (TBTU) as coupling agent afforded the tertiary amide 8.4. Hydrogenation of 8.4 under acidic conditions provided the final compound 8A. Palladium catalyzed Negishi-type coupling of 8.5 with zinc bromide reagent 2.6, conducted in tetrahydrofuran using tetrakistriphenylphosphinepalladium (0) as catalyst, provided the ethyl ester 8.6, which was hydrolyzed under basic conditions to give the carboxylic acid derivative 8.7. Coupling of the carboxylic acid derivative 8.7 with diethylamine (1.6) using O-benzotriazol-1-yl-N,N,N',N'-tetramethyluronium tetrafluoroborate (TBTU) as coupling agent afforded the tertiary amide 8.8. Hydrogenation of 8.8 provided the final compound 8B. Treatment of 8.8 with boron tribromide afforded the phenolic derivative 8.9, which was converted to 8C by hydrogenation.

Scheme 8a

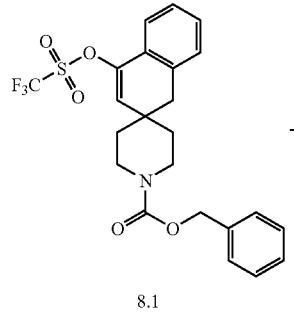

8.1

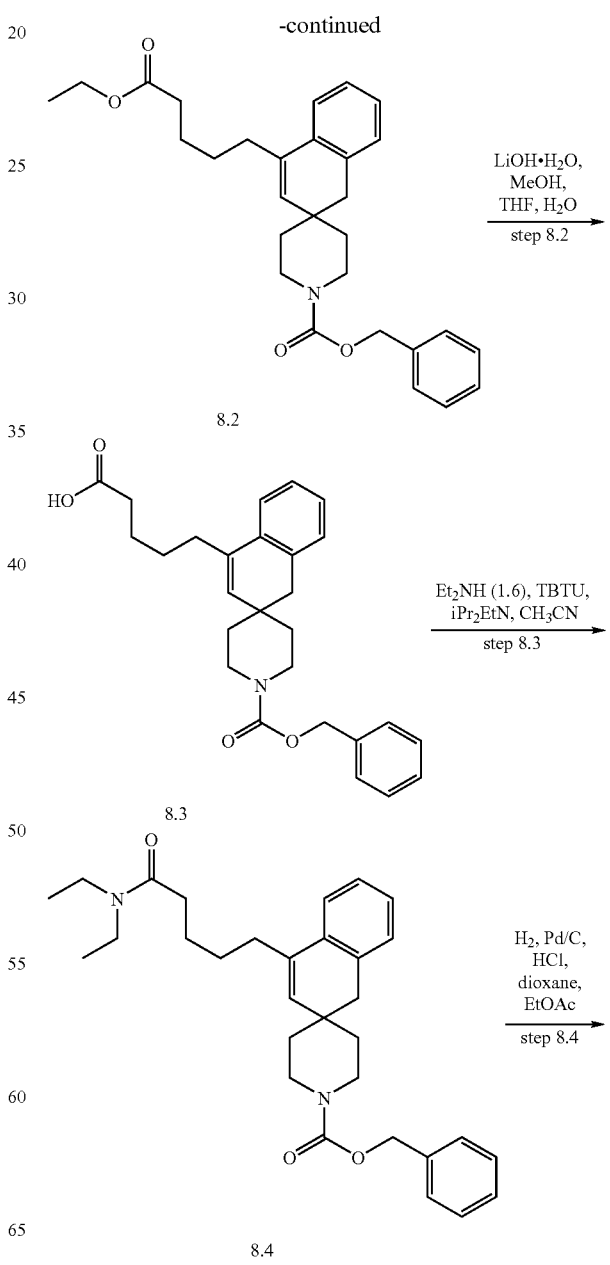

-continued
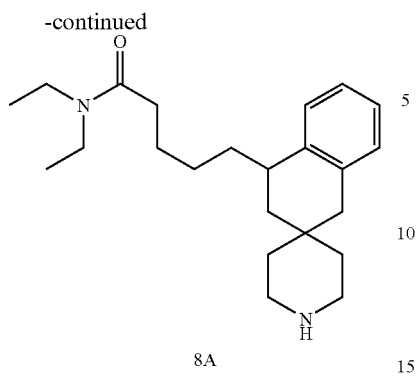
8A
Scheme 8b
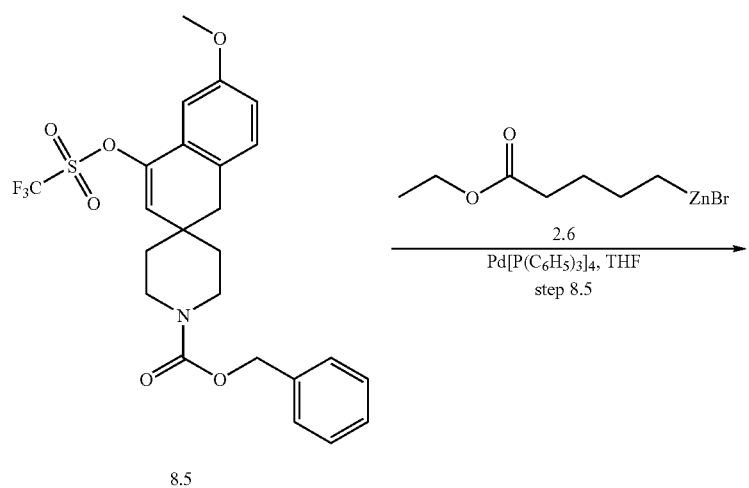
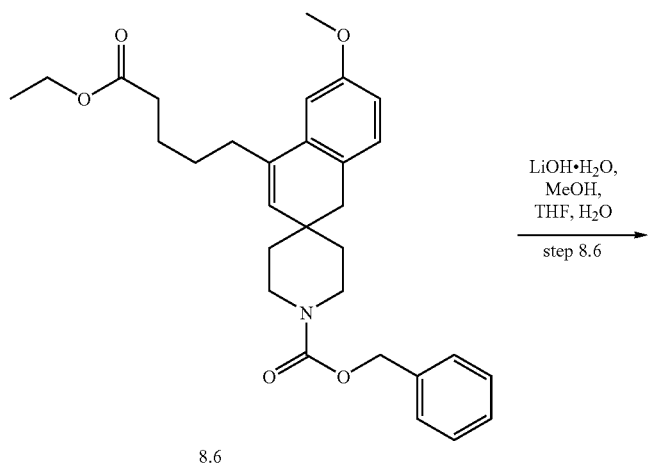

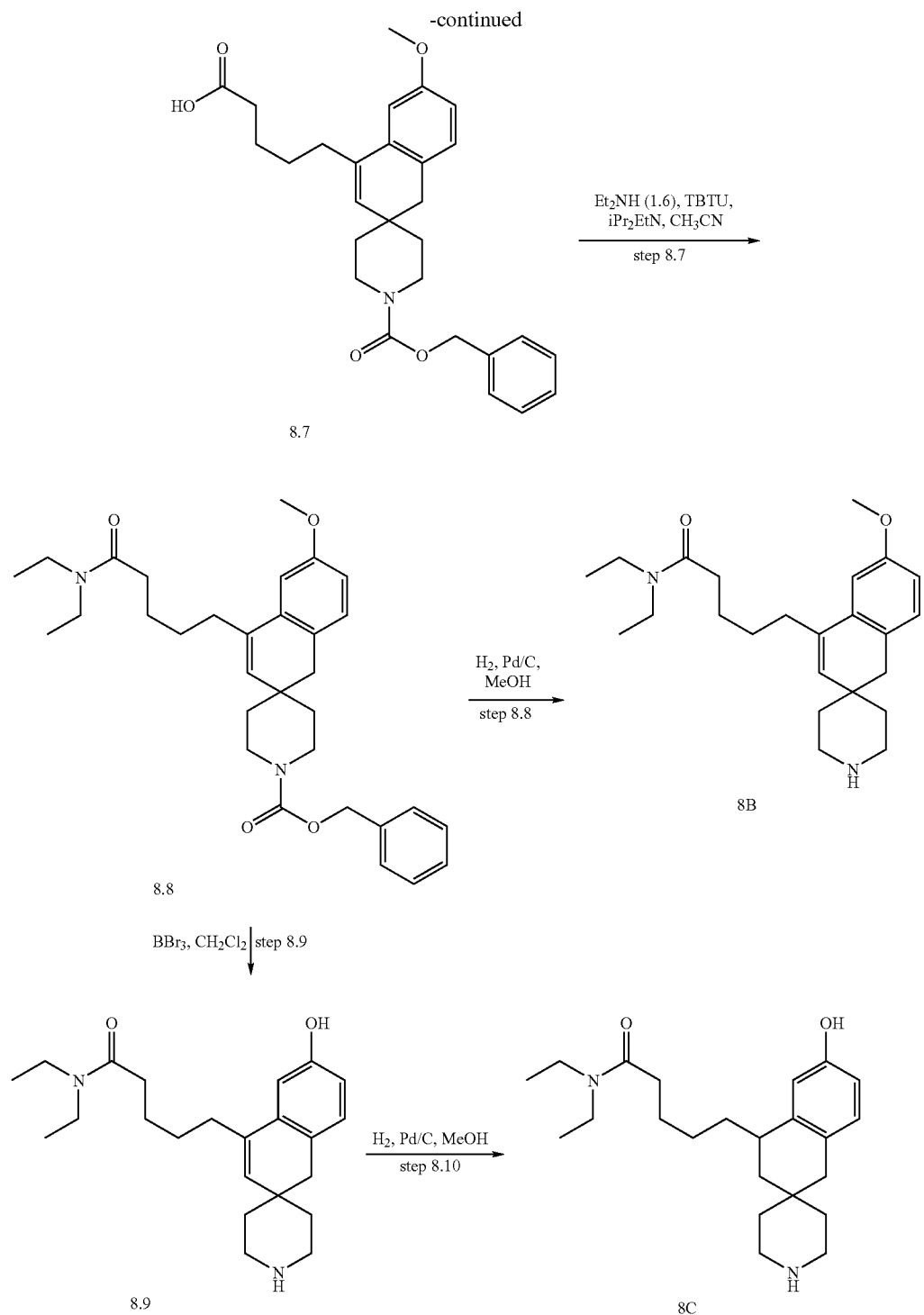

The synthesis of compounds 9A-9D is outlined in Scheme 9. Treatment of 8.9 with di-tert-butyl dicarbonate (7.7) provided the Boc derivative 9.1, which was converted to 9.2 by hydrogenation. Conversion of the phenol 9.2 to the triflate derivative 9.3 was achieved using N-phenylbis(trifluoromethanesulphonimide) 7.9 as triflating reagent. Palladium catalyzed carbonylation of 9.3, conducted in a mixture N,N-dimethylformamide/methanol using palladium (II) acetate, 1,1'-bis(diphenylphosphino)propane (dppp), and carbon monoxide, provided the methyl ester 9.4, which was hydrolyzed under basic conditions to give the carboxylic acid derivative 9.5. Coupling of the carboxylic acid 9.5 with various amines (9.6a; 9.6b or 2.3c) using O-benzotriazol-1-yl-N,N,N',N'-tetramethyluronium tetrafluoroborate (TBTU) as coupling agent afforded the amides 9.7. Treatment of the Boc derivatives of carboxylic acid 9.5 and the three 9.7 amides with hydrochloric acid provided the final compounds 9A-9D.

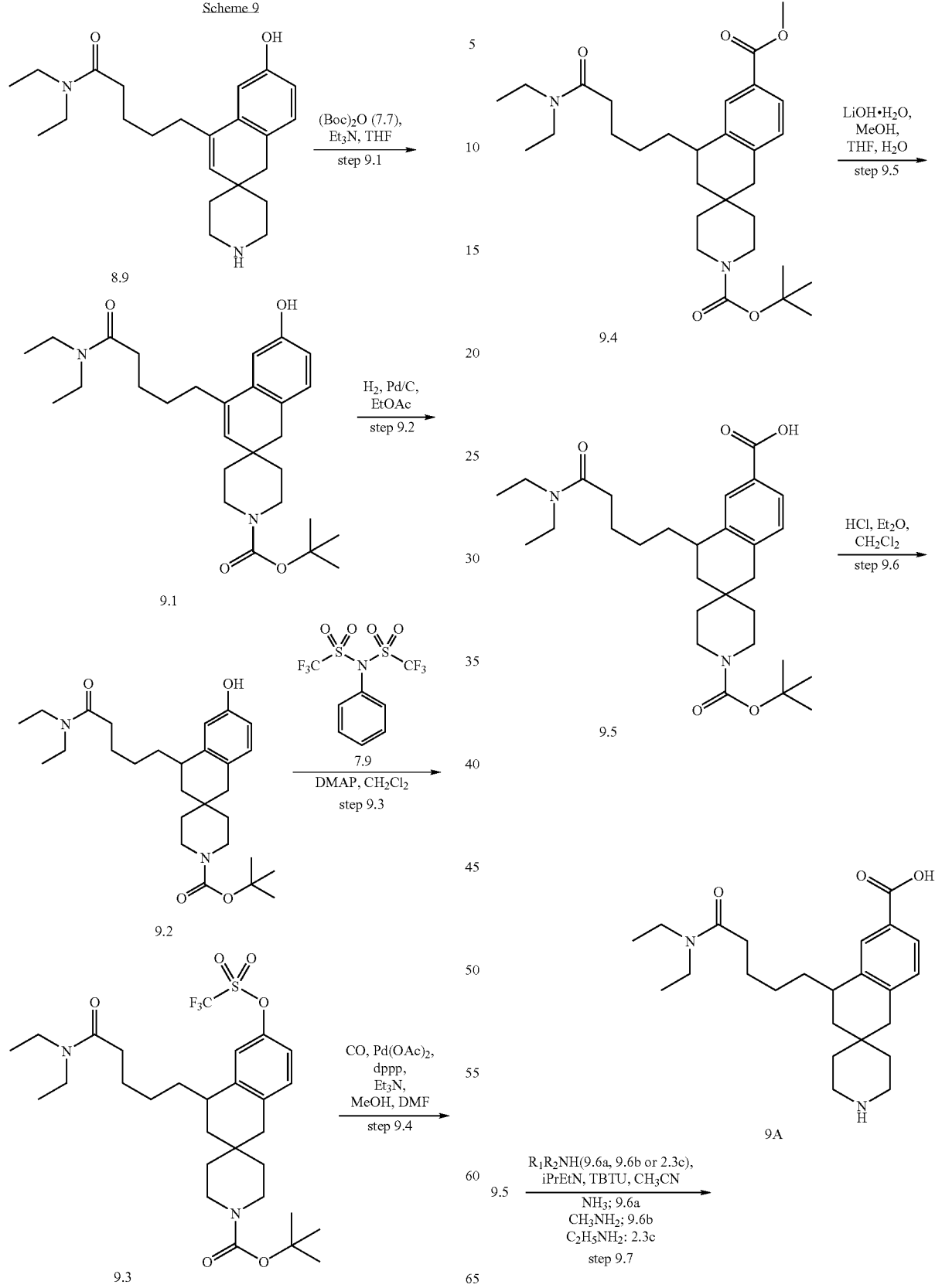

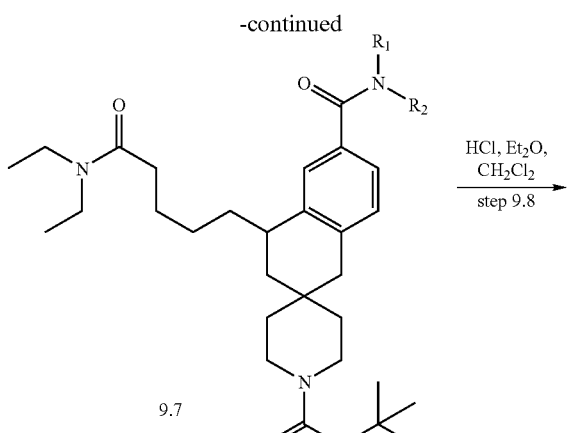

9.7

9.7a: R₁ = R₂ = H
9.7b: R₁ = methyl R₂ = H
9.7c: R₁ = Ethyl R₂ = H

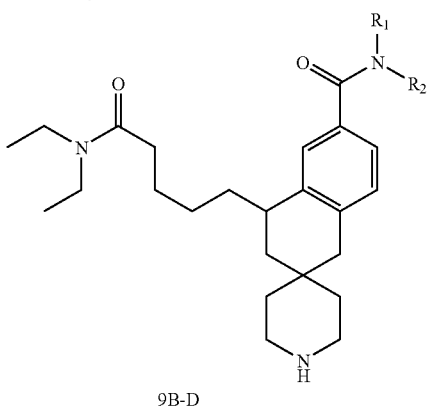

9B-D

EXPERIMENTAL PROCEDURES

Example 1A

Preparation of 1.4a:

To a solution of 1.1 (2.25 g, 5 mmol, 1 eq.) in dry tetrahydrofuran (40 mL) was added tetrakis(triphenylphosphine)palladium(0) (290 mg, 0.25 mmol, 0.05 eq.) followed by (3-ethoxy-3-oxopropyl)zinc(II) bromide 1.2 (0.5M solution in THF, 16 mL, 8 mmol, 1.6 eq.) dropwise. The reaction mixture was stirred at room temperature for 10 hours and then quenched with aqueous ammonium chloride (50 mL). The product was extracted with diethyl ether (3×100 mL) and the combined extracts were washed with brine, dried over sodium sulfate, filtered, and concentrated under reduced pressure. The crude product was purified by column chromatography (eluent: hexane/ethyl acetate mixture of increasing polarity). Yield: 62.5%

$^1$H NMR (400 MHz, CDCl$_3$) δ 7.23-7.12 (m, 2H), 6.95-6.83 (m, 2H), 5.36 (s, 1H), 4.14 (q, 2H), 3.82 (m,b, 2H), 3.27 (m,b, 2H), 2.74 (m, 2H), 2.54 (m, 2H), 1.93 (m, 2H), 1.60-1.45 (m, 11H), 1.26 (t, 3H). Mass Spectral Analysis m/z=402.0 (M+H)$^+$ Preparation of 1.5a:

To a solution of 1.4a (0.92 g, 2.3 mol, 1 eq.) in a mixture methanol (20 mL)/tetrahydrofuran (20 mL)/water (20 mL) was added lithium hydroxide monohydrate (0.39 g, 9.2 mmol, 4 eq.) in one portion. The reaction mixture was stirred at room temperature for 10 hours. The volatiles were removed under reduced pressure and the remaining aqueous solution was acidified with 1N hydrochloric acid until pH 2~3. The product was extracted with dichloromethane (3×100 mL) and the combined organics were dried over sodium sulfate, filtered, and concentrated under reduced pressure. The product was used for the next step without further purification. Yield: 98%

$^1$H NMR (400 MHz, DMSO-d$_6$) δ 12.17 (s, 1H), 7.24 (m, 1H), 7.16 (m, 1H), 6.92 (m, 1H), 6.86 (m, 1H), 5.56 (s, 1H), 3.65 (m, 2H), 3.20 (m, 2H), 2.61 (m, 2H), 2.43 (m, 2H), 1.76 (m, 2H), 1.56 (m, 2H), 1.40 (s, 9H). Mass Spectral Analysis m/z=371.9 (M−H)$^−$ Preparation of 1.7a:

To a solution of 1.5a (0.65 g, 1.74 mol, 1 eq.) in acetonitrile (30 mL) was slowly added diisopropylethylamine (0.73 mL, 4.18 mmol, 2.4 eq.), diethylamine 1.6 (0.54 mL, 5.22 mmol, 3 eq.) at room temperature and 10 minutes later at 0° C., O-benzotriazol-1-yl-N,N,N',N'-tetramethyluronium tetrafluoroborate (TBTU) (0.67 g, 2.09 mmol, 1.2 eq.) portionwise. The reaction mixture was slowly warmed to room temperature and stirred at room temperature for 10 hours. The volatiles were removed under reduced pressure and the residue was dissolved in ethyl acetate (200 mL). The organic solution was washed with 1M aqueous sodium bicarbonate (3×50 mL), brine, dried over sodium sulfate, filtered, and concentrated under reduced pressure. The crude product was purified by column chromatography (eluent: hexane/ethyl acetate mixture of increasing polarity). Yield: 91%

$^1$H NMR (400 MHz, CDCl$_3$) δ 7.23 (m, 1H), 7.15 (m, 1H), 6.94-6.84 (m, 2H), 5.39 (s, 1H), 3.83 (m, 2H), 3.38 (q, 2H), 3.33-3.20 (m, 4H), 2.78 (m, 2H), 2.49 (m, 2H), 1.93 (m, 2H), 1.61-1.41 (m, 11H), 1.11 (m, 6H). Mass Spectral Analysis m/z=429.0 (M+H)$^+$ Preparation of 1A:

To a solution of 1.7a (0.52 g, 1.2 mmol, 1 eq.) in dichloromethane (30 mL) was slowly added 4.0 M hydrogen chloride in dioxane (1.5 mL, 6 mmol, 5 eq.). The mixture was stirred at room temperature for 10 hours and two regioisomers were detected by LC/MS. The reaction mixture was concentrated under reduced pressure and 100 mg of the isomers were purified by preparative liquid chromatography to provide 65 mg of the pure product 1A as its trifluoroacetic acid salt.

$^1$H NMR (400 MHz, CDCl$_3$) δ 9.52 (s, 1H), 9.07 (s, 1H), 7.33-7.16 (m, 2H), 6.97 (m, 1H), 6.89 (m, 1H), 5.38 (s, 1H), 3.40 (m, 4H), 3.27 (m, 4H), 2.80 (m, 2H), 2.53 (m, 2H), 2.18 (m, 2H), 1.98 (m, 2H), 1.14 (m, 6H). Mass Spectral Analysis m/z=329.0 (M+H)$^+$

Example 1B

Preparation of 1.4b:

To a solution of 1.1 (2.25 g, 5 mmol, 1 eq.) in dry tetrahydrofuran (40 mL) was added tetrakis(triphenylphosphine)palladium(0) (290 mg, 0.25 mmol, 0.05 eq.) followed by (5-ethoxy-5-oxopentyl)zinc(II) bromide 1.3 (0.5M solution in THF, 16 mL, 8 mmol, 1.6 eq.) dropwise. The reaction mixture was stirred at room temperature for 10 hours and then quenched with aqueous ammonium chloride (50 mL). The product was extracted with diethyl ether (3×100 mL) and the combined extracts were washed with brine, dried over sodium sulfate, filtered, and concentrated under reduced pressure. The crude product was purified by column chromatography (eluent: hexane/ethyl acetate mixture of increasing polarity). Yield: 58%

¹H NMR (400 MHz, CDCl₃) δ 7.20 (dd, 1H), 7.14 (m, 1H), 6.90 (m, 1H), 6.86 (dd, 1H), 5.35 (s, 1H), 4.14 (q, 2H), 3.82 (m, 2H), 3.28 (m, 2H), 2.43 (m, 2H), 2.36 (t, 2H), 1.99-1.83 (m, 4H), 1.63-1.51 (m, 2H), 1.47 (s, 9H), 1.26 (t, 3H). Mass Spectral Analysis m/z=416.0 (M+H)⁺

Preparation of 1.5b:

To a solution of 1.4b (1.05 g, 2.5 mol, 1 eq.) in a mixture methanol (20 mL)/tetrahydrofuran (20 mL)/water (20 mL) was added lithium hydroxide monohydrate (0.42 g, 10 mmol, 4 eq.) in one portion. The reaction mixture was stirred at room temperature for 10 hours. The volatiles were removed under reduced pressure and the remaining aqueous solution was acidified with 1N hydrochloric acid until pH 2~3. The product was extracted with dichloromethane (3×100 mL) and the combined organics were dried over sodium sulfate, filtered, and concentrated under reduced pressure. The product was used for the next step without further purification. Yield: 96%

¹H NMR (400 MHz, DMSO-d₆) δ 12.07 (s, 1H), 7.26 (m, 1H), 7.14 (m, 1H), 6.91 (m, 1H), 6.86 (m, 1H), 5.54 (s, 1H), 3.68 (m, 2H), 3.20 (m, 2H), 2.38 (m, 2H), 2.28 (t, 2H), 1.78 (m, 2H), 1.68 (m, 2H), 1.58 (m, 2H), 1.41 (s, 9H). Mass Spectral Analysis m/z=386.0 (M−H)⁻

Preparation of 1.7b:

To a solution of 1.5b (0.73 g, 1.88 mol, 1 eq.) in acetonitrile (30 mL) was slowly added diisopropylethylamine (0.8 mL, 4.52 mmol, 2.4 eq.), diethylamine 1.6 (0.59 mL, 5.65 mmol, 3 eq.) at room temperature and 10 minutes later at 0° C., O-benzotriazol-1-yl-N,N,N',N'-tetramethyluronium tetrafluoroborate (TBTU) (0.73 g, 2.26 mmol, 1.2 eq.) portionwise. The reaction mixture was slowly warmed to room temperature and stirred at room temperature for 10 hours. The volatiles were removed under reduced pressure and the residue was dissolved in ethyl acetate (200 mL). The organic solution was washed with 1M aqueous sodium bicarbonate (3×50 mL), brine, dried over sodium sulfate, filtered, and concentrated under reduced pressure. The crude product was purified by column chromatography (eluent: hexane/ethyl acetate mixture of increasing polarity). Yield: 90%

¹H NMR (400 MHz, CDCl₃) δ 7.23 (m, 1H), 7.13 (m, 1H), 6.90 (m, 1H), 6.85 (m, 1H), 5.37 (s, 1H), 3.82 (m, 2H), 3.38 (q, 2H), 3.34-3.20 (m, 4H), 2.45 (m, 2H), 2.35 (t, 2H), 1.92 (m, 4H), 1.56 (m, 2H), 1.47 (s, 9H), 1.15 (t, 3H), 1.11 (t, 3H).
Mass Spectral Analysis m/z=443.0 (M+H)⁺

Preparation of 1B:

To a solution of 1.7b (0.65 g, 1.47 mmol, 1 eq.) in dichloromethane (30 mL) was slowly added 4.0M hydrogen chloride in dioxane (1.8 mL, 7.2 mmol, 5 eq.). The mixture was stirred at room temperature for 10 hours and two regioisomers were detected by LC/MS. The reaction mixture was concentrated under reduced pressure and 100 mg of the isomers were purified by preparative liquid chromatography to provide 78 mg of the pure product 1B as trifluoroacetic acid salt.

¹H NMR (400 MHz, CDCl₃) δ 9.48 (s, 1H), 9.04 (s, 1H), 7.32-7.14 (m, 2H), 6.95 (m, 1H), 6.88 (m, 1H), 5.38 (s, 1H), 3.46-3.22 (m, 8H), 2.52-2.35 (m, 4H), 2.17 (m, 2H), 2.03-1.84 (m, 4H), 1.25-1.09 (m, 6H). Mass Spectral Analysis m/z=343.0 (M+H)⁺

Example 1C

Preparation of 1C:

1C (hydrochloric acid salt) was obtained according to a procedure similar to the one described for 1D (hydrochloric acid salt) with the following exceptions:

Step 1.5: 1B was replaced by 1A.

¹H NMR (400 MHz, DMSO-d₆) δ 8.94 (m, 2H), 7.31 (m, 1H), 7.11 (m, 1H), 6.90 (m, 1H), 6.83 (m, 1H), 3.32-3.20 (m, 6H), 3.11 (m, 1H), 2.90 (m, 2H), 2.31 (m, 3H), 2.03 (m, 1H), 1.88 (m, 3H), 1.68 (m, 2H), 1.50 (m, 1H), 1.08 (t, 3H), 1.00 (t, 3H)

Mass Spectral Analysis m/z=331.0 (M+H)⁺

Example 1D

Preparation of 1D:

To a solution of the regioisomers from step 1.4 of the preparation of 1B (0.42 g, 1.1 mmol, 1 eq.) in methanol (20 mL) was added palladium [84 mg, 10 wt. % (dry basis) on activated carbon, 20% wt. eq.]. The reaction mixture was stirred under hydrogen atmosphere using a hydrogen balloon at room temperature for 10 hours. The palladium on activated carbon was filtered off using a celite pad and the filtrate was concentrated under reduced pressure to give 1D as hydrochloric acid salt. Yield: 100%

¹H NMR (400 MHz, DMSO-d₆) δ 8.91 (m, 2H), 7.28 (m, 1H), 7.10 (m, 1H), 6.89 (m, 1H), 6.83 (m, 1H), 3.32-3.18 (m, 6H), 3.11 (m, 1H), 2.89 (m, 2H), 2.31 (m, 2H), 2.05-1.82 (m, 5H), 1.72 (m, 1H), 1.51 (m, 4H), 1.10 (t, 3H), 1.00 (t, 3H)

Mass Spectral Analysis m/z=345.0 (M+H)⁺

Example 1E

Preparation of 1E:

To a solution of 1.4b (0.3 g, 0.72 mol, 1 eq.) in dichloromethane (50 mL) was slowly added 4.0M hydrogen chloride in dioxane (0.9 mL, 3.6 mmol, 5 eq.). The mixture was stirred at room temperature for 10 hours and then concentrated under reduced pressure. The resulting solids were collected by filtration and washed with ether (2×10 mL) to give 1E as hydrochloric acid salt. Yield: 95%

¹H NMR (400 MHz, DMSO-d₆) δ 8.91 (m, 2H), 7.30 (m, 1H), 7.19 (m, 1H), 6.94 (m, 2H), 5.59 (s, 1H), 4.06 (q, 2H), 3.16 (m, 4H), 2.58-2.33 (m, 4H), 1.99 (m, 2H), 1.87 (m, 2H), 1.73 (m, 2H), 1.17 (t, 3H) Mass Spectral Analysis m/z=316.0 (M+H)⁺

Example 2A

Preparation of 2.1:

Compound 1.4b (9.0 g, 21.7 mmol) was dissolved in ethyl acetate (500 mL), and the solution was hydrogenated in the presence of 10% Pd/C (2.7 g) at atmospheric pressure. After 2 days at room temperature, the reaction mixture was filtered and the filtrate was concentrated in vacuo to give the saturated ester 2.1. Yield: 100%

¹H NMR (400 MHz, CDCl₃) δ 7.21 (d, 1H), 7.10 (m, 1H), 6.88 (m, 1H), 6.81 (d, 1H), 3.84 (m, 2H), 3.35 (m, 1H), 3.01 (m, 1H), 2.90 (m, 1H), 2.35 (m, 2H), 2.0-1.40 (m, 10H), 1.48 (s, 9H), 1.25 (t, 3H).

Preparation of 2.2:

Lithium hydroxide monohydrate (5.04 g, 120 mmol) was added to the solution of ester 2.1 (8.34 g, 20 mmol) in a mixed solvent of methanol (150 mL), tetrahydrofuran (150 mL) and water (150 mL). The reaction mixture was stirred at room temperature overnight, concentrated in vacuo, and then washed with diethyl ether. The aqueous layer was acidified with 1N HCl to pH~4, and extracted with methylene chloride.

The combined organic extracts were dried over sodium sulfate and concentrated in vacuo to give the carboxylic acid 2.2. Yield: 93.8%

$^1$H NMR (400 MHz, DMSO $d_6$) δ 12.03 (brs, 1H), 7.26 (d, 1H), 7.08 (t, 1H), 6.87 (m, 1H), 6.78 (d, 1H), 3.70 (m, 2H), 3.27 (m, 1H), 2.90 (m, 2H), 2.25 (m, 2H), 1.98 (m, 2H), 1.66-1.45 (m, 8H), 1.40 (s, 9H).

Preparation of 2.5:

To a solution of the carboxylic acid 2.2 (778 mg, 2.0 mmol) in methylene chloride (60 mL) was added diisopropylamine (2.3a) (0.56 mL, 4 mmol), followed by triethylamine (1.12 ml, 8 mmol) and the Mukaiyama acylating reagent, [2-chloro-1-methylpyridinium iodide (2.4) (614 mg, 2.4 mmol)]. The reaction mixture was stirred at room temperature for 2 days and washed with saturated aqueous sodium bicarbonate, and dried over sodium sulfate. Evaporation of the solvent and purification of the residue by column chromatography on silica gel using hexane:ethyl acetate (2:1) as eluent, yielded the amide 2.5a. Yield: 53%

$^1$H NMR (400 MHz, CDCl$_3$) δ 7.22 (d, 1H), 7.10 (t, 1H), 6.85 (m, 2H), 3.96-3.78 (m, 3H), 3.40 (m, 2H), 2.98 (m, 2H), 2.30 (m, 2H), 2.05-1.40 (m, 10H), 1.48 (s, 9H), 1.38 (m, 6H), 1.19 (m, 6H).

Preparation of 2A:

To a solution of compound 2.5a (480 mg, 1.02 mmol) in methylene chloride (6 mL) was added a 2.0M anhydrous solution of hydrogen chloride in diethyl ether (20 mL, 40 mmol). The reaction mixture was stirred at room temperature overnight. Diethyl ether (50 mL) was then added to the reaction mixture, which was stirred for an additional 2 hours at room temperature. The clear upper solution was decanted, and the product was washed with diethyl ether. The product was then dissolved in methylene chloride. The resulting solution was concentrated and the resulting product was dried in vacuo to furnished 2A isolated as its hydrochloric acid salt. Yield: 90%

$^1$H NMR (400 MHz, DMSO $d_6$) δ 9.12 (brd, 2H), 7.26 (d, 1H), 7.08 (m, 1H), 6.84 (m, 2H), 3.96 (m, 1H), 3.83 (m, 1H), 3.20 (m, 2H), 3.10 (m, 1H), 2.89 (m, 2H), 2.29 (m, 2H), 1.95-1.73 (m, 6H), 1.50 (m, 4H), 1.29 (m, 6H), 1.15 (m, 6H). Mass Spectral Analysis m/z=373.4 (M+H)$^+$ Example 2B Preparation of 2B:

2B (hydrochloric acid salt) was obtained according to a procedure similar to the one described for 2A (hydrochloric acid salt) with the following exceptions:

Step 2.3: 2.3a was replaced by 2.3b.

$^1$H NMR (400 MHz, DMSO $d_6$) δ 9.13 (brd, 2H), 7.30 (m, 5H), 7.10 (m, 1H), 6.85 (m, 2H), 4.88 (d, 1H), 4.80 (d, 1H), 4.68 (d, 1H), 4.60 (d, 1H), 3.20 (m, 2H), 3.10 (m, 1H), 2.90 (m, 2H), 2.40 (m, 2H), 2.00-1.50 (m, 10H). Mass Spectral Analysis m/z=391.3 (M+H)$^+$ Example 2C Preparation of 2C:

2C (hydrochloric acid salt) was obtained according to a procedure similar to the one described for 2A (hydrochloric acid salt) with the following exceptions: Step 2.3: 2.3a was replaced by 2.3c.

$^1$H NMR (400 MHz, DMSO $d_6$) δ 9.20 (brs, 2H), 7.84 (brs, 1H), 7.26 (d, 1H), 7.10 (t, 1H), 6.90 (t, 1H), 3.20 (m, 2H), 3.08 (m, 3H), 2.89 (m, 2H), 2.10-1.75 (m, 8H), 1.50 (m, 4H), 1.0 (t, 3H). Mass Spectral Analysis m/z=317.3 (M+H)$^+$ Example 2D Preparation of 2D:

2D (hydrochloric acid salt) was obtained according to a procedure similar to the one described for 2A (hydrochloric acid salt) with the following exceptions: Step 2.3: 2.3a was replaced by 2.3d.

$^1$H NMR (400 MHz, DMSO $d_6$) δ 9.10 (brd, 2H), 7.81 (t, 1H), 7.23 (d, 1H), 7.10 (t, 1H), 6.90 (t, 1H), 6.84 (d, 1H), 3.20 (m, 2H), 3.04 (m, 3H), 2.89 (m, 2H), 2.10-1.75 (m, 8H), 1.50-1.28 (m, 8H), 0.88 (t, 3H). Mass Spectral Analysis m/z=317.3 (M+H)$^+$ Example 2E Preparation of 2.7:

To a solution of 1.1 (1.85 g, 4.12 mmol) in anhydrous tetrahydrofuran (50 mL) at room temperature was added under nitrogen atmosphere a 0.5M solution of 5-ethoxy-5-oxopentylzinc bromide (2.6) in tetrahydrofuran (13 mL, 6.5 mmol) followed by tetrakis(triphenylphosphine)palladium (0) (232 mg, 0.2 mmol). The reaction mixture was stirred at 50° C. overnight and concentrated in vacuo. The residue was partitioned in diethyl ether and saturated aqueous ammonium chloride. The organic layer was separated, washed with water, brine and dried over sodium sulfate. Evaporation of the solvent and purification of the residue by column chromatography on silica gel using hexane/ethyl acetate (10:1) as eluent, yielded the desired product 2.7. Yield: 49%.

$^1$H NMR (400 MHz, CDCl$_3$) δ 7.15 (m, 2H), 6.90 (m, 2H), 5.32 (s, 1H), 4.12 (q, 2H), 3.81 (m, 2H), 3.29 (m, 2H), 2.41 (t, 2H), 2.31 (t, 2H), 1.95 (m, 2H), 1.70-1.58 (m, 6H), 1.48 (s, 9H), 1.28 (t, 3H).

Preparation of 2.8:

Compound 2.7 (830 mg, 1.9 mmol) was dissolved in ethyl acetate (60 mL) and hydrogenated in the presence of 10% Pd/C (162 mg) at room temperature overnight. The reaction mixture was filtered and the filtrate was concentrated in vacuo to yield the saturated ester 2.8. Yield: 98.3%.

$^1$H NMR (400 MHz, CDCl$_3$) δ 7.22 (d, 1H), 7.10 (t, 1H), 6.90 (t, 1H), 6.83 (d, 1H), 4.10 (q, 2H), 3.88 (m, 2H), 3.38 (m, 1H), 2.97 (m, 2H), 2.32 (t, 2H), 2.0-1.38 (m, 12H), 1.48 (s, 9H), 1.29 (t, 3H).

Preparation of 2.9:

To a solution of 2.8 (820 mg, 1.9 mmol) in a mixture of methanol (15 mL)/tetrahydrofuran (15 mL)/water (15 mL) was added lithium hydroxide monohydrate (504 mg, 12 mmol). The reaction mixture was stirred at room temperature overnight, concentrated in vacuo and washed with diethyl ether. The aqueous layer was acidified with 1N HCl to pH ~4 and extracted with methylene chloride. The combined organic extracts were dried over sodium sulfate and concentrated to give the carboxylic acid 2.9. Yield: 100%.

$^1$H NMR (400 MHz, DMSO-$d_6$) δ12.0 (s, 1H), 7.29 (d, 1H), 7.08 (t, 1H), 6.88 (t, 1H), 6.79 (d, 1H), 3.70 (m, 2H), 3.30 (m, 1H), 2.90 (m, 1H), 2.12 (t, 2H), 1.98 (m, 2H), 1.62-1.30 (m, 10H), 1.40 (s, 9H).

Preparation of 2.10:

To a solution of 2.9 (806 mg, 2.0 mmol) in methylene chloride (60 mL) was added diethylamine (1.6) (0.43 mL, 4 mmol), followed by triethylamine (1.12 ml, 8 mmol) and Mukaiyama acylating reagent, [2-chloro-1-methylpyridinium iodide (2.4) (614 mg, 2.4 mmol)]. The reaction mixture was stirred at room temperature overnight, washed with saturated aqueous sodium bicarbonate, and dried over sodium sulfate. Evaporation of the solvent and purification of the residue by column chromatography on silica gel using hexane/ethyl acetate (1:1) as eluent, yielded the amide 2.10. Yield: 83.7%.

$^1$H NMR (400 MHz, CDCl$_3$) δ 7.22 (d, 1H), 7.10 (t, 1H), 6.88 (t, 1H), 6.80 (d, 1H), 3.85 (m, 2H), 3.38-3.28 (m, 5H), 2.95 (m, 2H), 2.30 (t, 2H), 2.05-1.40 (m, 12H), 1.47 (s, 9H), 1.19 (t, 3H), 1.10 (t, 3H).

Preparation of 2E:

To a solution of 2.10 (740 mg, 1.62 mmol) in methylene chloride (10 mL) was added a 2.0M anhydrous solution of hydrogen chloride in diethyl ether (30 mL, 60 mmol). The reaction mixture was stirred at room temperature overnight. Diethyl ether (80 mL) was added to the reaction mixture, which was stirred for an additional 2 hours at room temperature. The clear upper solution was decanted, and the product was washed with diethyl ether. The residue was dissolved in methylene chloride. The resulting solution was concentrated and the product was dried in vacuo to furnish the 2E isolated as its hydrochloric acid salt. Yield: 95.8%.

$^1$H NMR (400 MHz, DMSO d$_6$) δ 9.09 (brs, 2H), 7.30 (d, 1H), 7.10 (t, 1H), 6.90 (t, 1H), 6.81 (d, 1H), 3.22 (m, 6H), 3.10 (m, 1H), 2.89 (m, 2H), 2.29 (t, 2H), 2.0-1.30 (m, 12H), 1.10 (t, 3H), 1.0 (t, 3H). Mass Spectral Analysis m/z=359.4 (M+H)$^+$ Example 2F Preparation of 2.12:

To a solution of enol triflate 1.1 (5.84 g, 12 mmol) in anhydrous tetrahydrofuran (150 mL) at room temperature was added under nitrogen atmosphere a 0.5M solution of 6-ethoxy-6-oxohexylzinc bromide (2.11) in tetrahydrofuran (13 mL, 6.5 mmol) followed by tetrakis(triphenylphosphine)palladium(0) (925 mg, 0.8 mmol). The reaction mixture was stirred at 50° C. overnight and then cooled to room temperature. The reaction mixture was quenched with water and extracted with ethyl acetate. The combined organic extracts were dried over sodium sulfate and concentrated in vacuo. The residue was purified by column chromatography on silica gel using hexane/ethyl acetate (8:1) as eluent. Yield: 31%.

$^1$H NMR (400 MHz, CDCl$_3$) δ 7.12 (m, 2H), 6.88 (m, 2H), 5.30 (s, 1H), 4.12 (q, 2H), 3.81 (m, 2H), 3.28 (m, 2H), 2.38 (t, 2H), 2.30 (t, 2H), 1.92 (m, 2H), 1.65-1.40 (m, 8H), 1.48 (s, 9H), 1.26 (t, 3H).

Preparation of 2.13:

Compound 2.12 (1.6 g, 3.61 mmol) was dissolved in ethyl acetate (120 mL), and hydrogenated in the presence of 10% Pd/C (480 mg) using a hydrogen balloon. After 2 days at room temperature, the reaction mixture was filtered and the filtrate was concentrated in vacuo to give the saturated ester 2.13. Yield: ~100%.

$^1$H NMR (400 MHz, CDCl$_3$) δ 7.21 (d, 1H), 7.10 (t, 1H), 6.88 (t, 1H), 6.82 (d, 1H), 4.11 (q, 2H), 3.84 (m, 2H), 3.36 (m, 1H), 2.92 (m, 2H), 2.30 (t, 2H), 2.0-1.38 (m, 14H), 1.48 (s, 9H), 1.29 (t, 3H).

Preparation of 2.14:

Lithium hydroxide monohydrate (924 g, 22 mmol) was added to a solution of ester 2.13 (1.58 g, 3.55 mmol) in a mixture of methanol (30 mL), tetrahydrofuran (30 mL) and water (30 mL). The reaction mixture was stirred at room temperature overnight, concentrated in vacuo and washed with diethyl ether. The aqueous layer was acidified with 1N HCl to pH~4 and extracted with methylene chloride. The combined organic extracts were dried over sodium sulfate and concentrated in vacuo to give the carboxylic acid 2.14. Yield: ~100%.

$^1$H NMR (400 MHz, DMSO d$_6$) δ 12.00 (brs, 1H), 7.28 (d, 1H), 7.06 (t, 1H), 6.88 (t, 1H), 6.79 (d, 1H), 3.70 (m, 2H), 3.30 (m, 1H), 2.90 (m, 2H), 2.20 (t, 2H), 1.98 (m, 2H), 1.65-1.30 (m, 12H), 1.40 (s, 9H).

Preparation of 2.15a:

To the solution of 2.14 (700 mg, 1.68 mmol) in methylene chloride (50 mL) was added diethylamine (1.6) (0.36 mL, 3.36 mmol), followed by triethylamine (0.94 ml, 6.72 mmol) and the Mukaiyama acylating reagent, [2-chloro-1-methylpyridinium iodide (2.4) (516 mg, 2.02 mmol)]. The reaction mixture was stirred at room temperature overnight, washed with saturated aqueous sodium bicarbonate, and dried over sodium sulfate. Evaporation of the solvent and purification of the residue by column chromatography on silica gel using hexane/ethyl acetate (1:1) as eluent, yielded the amide 2.15a. Yield: 75.7%.

$^1$H NMR (400 MHz, CDCl$_3$) δ 7.25 (d, 1H), 7.10 (t, 1H), 6.87 (t, 1H), 6.80 (d, 1H), 3.86 (m, 2H), 3.40-3.30 (m, 5H), 2.95 (m, 2H), 2.30 (t, 2H), 2.0-1.4 (m, 14H), 1.48 (s, 9H), 1.19 (t, 3H), 1.10 (t, 3H).

Preparation of 2F:

To a solution of compound 2.15a (550 mg, 1.17 mmol) in methylene chloride (10 mL) was added a 2.0M anhydrous solution of hydrogen chloride in diethyl ether (30 mL, 60 mmol). The reaction mixture was stirred at room temperature overnight. Diethyl ether (80 mL) was added to the reaction mixture, which was stirred for an additional 2 hours at room temperature. The clear upper solution was decanted, and the product was washed with diethyl ether. The product was dissolved in methylene chloride and the resulting solution was concentrated in vacuo. The product was dried in vacuo to furnish the 2F isolated as its hydrochloric acid salt. Yield: ~100%.

$^1$H NMR (400 MHz, DMSO d$_6$) δ 9.06 (brs, 2H), 7.29 (d, 1H), 7.10 (m, 1H), 6.90 (t, 1H), 6.81 (d, 1H), 3.22 (m, 6H), 3.10 (m, 1H), 2.89 (m, 2H), 2.25 (t, 2H), 1.96-1.70 (m, 6H), 1.50-1.30 (m, 8H), 1.10 (t, 3H), 1.0 (t, 3H). Mass Spectral Analysis m/z=373.5 (M+H)$^+$ Example 2G Preparation of 2G:

2G (hydrochloric acid salt) was obtained according to a procedure similar to the one described for 2F (hydrochloric acid salt) with the following exception: Step 2.13: 1.6 was replaced by 2.3a.

$^1$H NMR (400 MHz, DMSO d$_6$) δ 9.12 (brs, 2H), 7.29 (d, 1H), 7.10 (m, 1H), 6.90 (t, 1H), 6.81 (d, 1H), 4.30 (m, 1H), 3.98 (m, 1H), 3.20 (m, 2H), 3.10 (m, 1H), 2.86 (m, 2H), 2.22 (t, 2H), 1.98-1.72 (m, 6H), 1.48-1.32 (m, 8H), 1.29 (d, 6H), 1.12 (d, 6H).

Mass Spectral Analysis m/z=401.5 (M+H)$^+$

Example 3A

Preparation of 3.2:

To a solution of 3.1 (4.67 g, 10 mmol, 1 eq.) in dry tetrahydrofuran (100 mL) was added tetrakis(triphenylphosphine)palladium(0) (580 mg, 0.5 mmol, 0.05 eq.) followed by a 0.5 M solution of (5-ethoxy-5-oxopentyl)zinc(II) bromide 2.6 in tetrahydrofuran (32 mL, 16 mmol, 1.6 eq.) dropwise. The reaction mixture was stirred at 45° C. for 10 hours and quenched with aqueous ammonium chloride (100 mL) at room temperature. The product was extracted with ether (3×100 mL) and the combined extracts were washed with water, brine, dried over sodium sulfate, filtered, and concentrated under reduced pressure. The crude product was purified by column chromatography (eluent: hexane/ethyl acetate mixture of increasing polarity). Yield: 46%

$^1$H NMR (400 MHz, CDCl$_3$) δ 6.89-6.76 (m, 3H), 5.39 (s, 1H), 4.13 (q, 2H), 3.83 (m, 2H), 3.25 (m, 2H), 2.34 (m, 4H), 1.92 (m, 2H), 1.70 (m, 2H), 1.62-1.44 (m, 13H), 1.25 (t, 3H). Mass Spectral Analysis m/z=448.8 (M+H)$^+$ Preparation of 3.3:

To a solution of 3.2 (2.08 g, 4.6 mmol, 1 eq.) in a mixture of methanol (20 mL), tetrahydrofuran (20 mL) and water (20 mL) was added lithium hydroxide monohydrate (0.78 g, 18.6 mmol, 4 eq.) in one portion. The reaction mixture was stirred at room temperature for 10 hours. The volatiles were removed under reduced pressure and the remaining aqueous solution was acidified with 1N hydrochloric acid until pH 2~3. The product was extracted with dichloromethane (3×100 mL) and the combined extracts were dried over sodium sulfate, filtered, and concentrated under reduced pressure. The product was used for the next step without further purification. Yield: 98%

$^1$H NMR (400 MHz, CDCl$_3$) δ 6.88-6.77 (m, 3H), 5.39 (s, 1H), 3.83 (m, 2H), 3.25 (m, 2H), 2.38 (m, 4H), 1.92 (m, 2H), 1.72 (m, 2H), 1.64-1.51 (m, 4H), 1.47 (s, 9H)

Mass Spectral Analysis m/z=418.84 (M−H)$^-$

Preparation of 3.4:

To a solution of 3.3 (1.4 g, 3.3 mmol, 1 eq.) in acetonitrile (50 mL) was slowly added diisopropylethylamine (1.38 mL, 7.92 mmol, 2.4 eq.), diethylamine 1.6 (0.68 mL, 6.6 mmol, 2 eq.) at room temperature and 10 minutes later at 0° C., O-benzotriazol-1-yl-N,N,N',N'-tetramethyluronium tetrafluoroborate (TBTU) (1.27 g, 3.96 mmol, 1.2 eq.) portionwise. The reaction mixture was slowly warmed to room temperature and stirred at room temperature for 10 hours. The volatiles were removed under reduced pressure and the residue was dissolved in ethyl acetate (200 mL). The resulting solution was washed with 1M aqueous sodium bicarbonate (5×100 mL), brine, dried over sodium sulfate, filtered, and concentrated under reduced pressure. The crude product was purified by column chromatography (eluent: hexane/ethyl acetate mixture of increasing polarity). Yield: 80%

$^1$H NMR (400 MHz, CDCl$_3$) δ 6.90-6.76 (m, 3H), 5.40 (s, 1H), 3.82 (m, 2H), 3.37 (q, 2H), 3.33-3.16 (m, 4H), 2.34 (m, 4H), 1.91 (m, 2H), 1.73 (m, 2H), 1.63-1.51 (m, 4H), 1.46 (s, 9H), 1.16 (t, 3H), 1.11 (t, 3H). Mass Spectral Analysis m/z=475.85 (M+H)$^+$ Preparation of 3.5:

To a solution of 3.4 (1.25 g, 2.6 mmol, 1 eq.) in ethyl acetate (30 mL) was added palladium [250 mg, 10 wt. % (dry basis) on activated carbon, 20% wt. eq.]. The reaction mixture was stirred under hydrogen atmosphere using a hydrogen balloon at room temperature for 10 hours. The palladium on activated carbon was filtered off on a celite pad and the filtrate was concentrated under reduced pressure. The crude product was purified by column chromatography (eluent: ethyl acetate/hexane mixture of increasing polarity). Yield: 100%

$^1$H NMR (400 MHz, CDCl$_3$) δ 6.92 (dd, 1H), 6.83-6.78 (m, 2H), 4.01-3.69 (m, 2H), 3.43-3.25 (m, 5H), 3.08-2.80 (m, 2H), 2.32 (m, 2H), 1.95 (m, 1H), 1.86 (m, 1H), 1.82-1.60 (m, 5H), 1.57-1.31 (m, 14H), 1.17 (t, 3H), 1.11 (t, 3H). Mass Spectral Analysis m/z=477.86 (M+H)$^+$ Preparation of 3A:

To a solution of 3.5 (1.25 g, 2.6 mmol, 1 eq.) in dichloromethane (50 mL) was slowly added a 2.0M anhydrous solution of hydrogen chloride in diethyl ether (7.8 mL, 15.6 mmol, 6 eq.). The mixture was stirred at room temperature for 10 hours and then concentrated under reduced pressure. The crude was purified by column chromatography (eluent: methanol/dichloromethane mixture of increasing polarity) to give 3A isolated as its hydrochloric acid salt. Yield: 85%

$^1$H NMR (400 MHz, DMSO-d$_6$) δ 8.93 (s, b, 2H), 7.15 (dd, 1H), 6.94 (m, 1H), 6.84 (dd, 1H), 3.32-3.15 (m, 6H), 3.09 (m, 1H), 2.87 (m, 2H), 2.28 (t, 2H), 2.03-1.80 (m, 5H), 1.70 (m, 1H), 1.63-1.39 (m, 4H), 1.32 (m, 2H), 1.09 (t, 3H), 0.99 (t, 3H)

Mass Spectral Analysis m/z=377.45 (M+H)$^+$

Example 3B

Preparation of 3.7:

To a solution of 3.6 (74.20 g, 153.2 mmol, 1 eq.) in dry tetrahydrofuran (700 mL) under nitrogen was added tetrakis(triphenylphosphine)palladium(0) (8.85 g, 7.66 mmol, 0.05 eq.) and then a 0.50M solution of 5-ethoxy-5-oxopentylzinc bromide (2.6) in tetrahydrofuran (460 mL, 230 mmol, 1.5 eq.) over a 20 minute period. The mixture was stirred at 45° C. for 10 hours. Additional amount of a 0.50M solution of 5-ethoxy-5-oxopentylzinc bromide (2.6) in tetrahydrofuran (150 mL, 75 mmol, 0.5 eq.) was added to the mixture, which was stirred at 45° C. for another 10 hours. The volatiles were removed under reduced pressure and the crude product was partitioned between diethyl ether (800 mL) and saturated ammonium chloride (500 mL). The two phases were separated and the organics were washed with water (3×150 mL), brine, dried over sodium sulfate, filtered, and concentrated under reduced pressure. The crude product was purified by column chromatography (eluent: ethyl acetate/hexane mixture of increasing polarity). Yield: 54%

$^1$H NMR (400 MHz, CDCl$_3$) δ 7.08 (m, 1H), 6.55 (dd, 1H), 6.48 (dd, 1H), 5.30 (s, 1H), 4.10 (q, 2H), 3.80 (s, 3H), 3.75 (m, 2H), 3.27 (m, 2H), 2.59 (m, 2H), 2.28 (t, 2H), 1.90 (m, 2H), 1.69-1.37 (m, 15H), 1.24 (t, 3H). Mass Spectral Analysis m/z=460.51 (M+H)$^+$ Preparation of 3.8:

To a solution of 3.7 (38.4 g, 83.6 mmol, 1 eq.) in a mixture of methanol (200 mL), tetrahydrofuran (200 mL) and water (200 mL) was added lithium hydroxide monohydrate (14.0 g, 334 mmol, 4 eq.) portionwise. The mixture was stirred at room temperature for 10 hours. The volatiles were removed under reduced pressure. Water (500 mL) was added to the mixture, which was washed with diethyl ether (300 mL). The aqueous phase was acidified with 1N hydrochloric acid until pH 4. The product was then extracted with dichloromethane (1×500 mL, 3×150 mL) and the combined extracts were dried over sodium sulfate, filtered, and concentrated under reduced pressure. The product was used for the next step without further purification. Yield: 95%

$^1$H NMR (400 MHz, CDCl$_3$) δ 7.08 (m, 1H), 6.55 (dd, 1H), 6.48 (dd, 1H), 5.31 (s, 1H), 3.80 (s, 3H), 3.76 (m, 2H), 3.28 (m, 2H), 2.60 (m, 2H), 2.34 (t, 2H), 1.90 (m, 2H), 1.70-1.40 (m, 15H).

Mass Spectral Analysis m/z=430.54 (M−H)$^-$

Preparation of 3.9:

To a solution of 3.8 (34.45 g, 79.8 mmol, 1 eq.) in acetonitrile (200 mL) was added N,N-diisopropylethylamine (34.76 mL, 199.6 mmol, 2.5 eq.), and diethylamine 1.6 (16.52 mL, 159.7 mmol, 2 eq.). The mixture was cooled to 0° C. and O-benzotriazol-1-yl-N,N,N',N'-tetramethyluronium tetrafluoroborate (TBTU) (28.20 g, 87.82 mmol, 1.1 eq.) was added portionwise. The reaction was gradually warmed at room temperature and stirred at room temperature for 10 hours. The volatiles were removed under reduced pressure and the residue was dissolved in diethyl ether (800 mL). The mixture was washed with saturated sodium bicarbonate and with 1N hydrochloric acid (4×100 mL). The organics were dried over sodium sulfate, filtered and then concentrated. The product was used for the next step without further purification. Yield: 98%

$^1$H NMR (400 MHz, CDCl$_3$) δ 7.07 (m, 1H), 6.55 (dd, 1H), 6.48 (dd, 1H), 5.32 (s, 1H), 3.80 (s, 3H), 3.74 (m, 2H), 3.36 (q, 2H), 3.32-3.21 (m, 4H), 2.62 (m, 2H), 2.27 (t, 2H), 1.90 (m, 2H), 1.73-1.37 (m, 15H), 1.14 (t, 3H), 1.11 (t, 3H)

Mass Spectral Analysis m/z=487.54 (M+H)$^+$

Preparation of 3.10:

To a solution of 3.9 (38 g, 78 mmol, 1 eq.) in methanol (300 mL) was added palladium [5.78 g, 10 wt. % (dry basis) on activated carbon, 15% wt. eq.]. The reaction mixture was stirred under hydrogen atmosphere using a hydrogen balloon at room temperature for 10 hours. The palladium on activated carbon was filtered off on a celite pad and the filtrate was concentrated under reduced pressure. The product was used for the next step without further purification. Yield: 100%

$^1$H NMR (400 MHz, CDCl$_3$) δ 7.05 (m, 1H), 6.49 (dd, 1H), 6.44 (dd, 1H), 3.95-3.65 (m, 5H), 3.41-3.24 (m, 5H), 2.95 (m, 2H), 2.29 (m, 2H), 2.05 (m, 1H), 1.92 (m, 1H), 1.85-1.27 (m, 19H), 1.16 (t, 3H), 1.10 (t, 3H). Mass Spectral Analysis m/z=489.54 (M+H)$^+$ Preparation of 3B:

To a solution of 3.10 (38.0 g, 77.8 mmol, 1 eq.) in methylene chloride (500 mL) was added a 2.0M anhydrous solution of hydrogen chloride in diethyl ether (230 mL, 460 mmol, 6 eq.) dropwise. The mixture was stirred at room temperature for 10 hours. The organic solvents were removed under reduced pressure and the residue was dried in vacuo. The crude product was purified by column chromatography (eluent: methanol/dichloromethane mixture of increasing polarity) to give 3β isolated as its hydrochloric acid salt.

$^1$H NMR (400 MHz, DMSO-d$_6$) δ 8.91 (s, b, 2H), 7.06 (m, 1H), 6.6.55 (dd, 1H), 6.48 (dd, 1H), 3.76 (s, 3H), 3.31-3.02 (m, 7H), 2.85 (m, 2H), 2.25 (m, 2H), 2.05-1.86 (m, 4H), 1.80-1.61 (m, 3H), 1.57-1.37 (m, 3H), 1.25 (m, 2H), 1.08 (t, 3H), 0.98 (t, 3H)

Mass Spectral Analysis m/z=389.4 (M+H)$^+$

Example 3C

Preparation of 3.12:

To a solution of 3.11 (4.72 g, 9.27 mmol, 1 eq.) in dry tetrahydrofuran (70 mL) under nitrogen was added tetrakis(triphenylphosphine)palladium(0) (0.53 g, 0.46 mmol, 0.05 eq.) and then a 0.50M solution of 5-ethoxy-5-oxopentylzinc bromide (2.6) in tetrahydrofuran (37 mL, 18.5 mmol, 2 eq.) slowly. The mixture was stirred at 45° C. for 10 hours. Additional amount of a 0.50M solution of 5-ethoxy-5-oxopentylzinc bromide (2.6) in tetrahydrofuran (18.54 mL, 9.27 mmol, 1 eq.) was added to the mixture, which was stirred at 45° C. for an additional 10 hours. The volatiles were removed under reduced pressure and the crude product was partitioned between diethyl ether (300 mL) and saturated ammonium chloride (200 mL). The two phases were separated and the organics were washed with water (3×50 mL), brine, dried over sodium sulfate, filtered, and concentrated under reduced pressure. The crude product was purified by column chromatography (eluent: ethyl acetate/hexane mixture of increasing polarity).

Yield: 49%

$^1$H NMR (400 MHz, CDCl$_3$) δ 7.06 (m, 1H), 6.71 (dd, 1H), 6.59 (dd, 1H), 5.33 (s, 1H), 5.17 (s, 2H), 4.10 (q, 2H), 3.76 (m, 2H), 3.49 (s, 3H), 3.27 (m, 2H), 3.62 (m, 2H), 3.28 (t, 2H), 1.91 (m, 2H), 1.69-1.41 (m, 15H), 1.23 (t, 3H). Mass Spectral Analysis m/z=490.50 (M+H)$^+$ Preparation of 3.13:

To a solution of 3.12 (2.2 g, 4.49 mmol, 1 eq.) in a mixture of methanol (30 mL), tetrahydrofuran (30 mL) and water (30 mL) was added lithium hydroxide monohydrate (0.75 g, 18.87 mmol, 4 eq.). The mixture was stirred at room temperature for 10 hours. The organic solvents were removed under reduced pressure and the remaining aqueous solution was acidified with 1N hydrochloric acid until pH 4. The product was then extracted with dichloromethane (3×100 mL) and the combined extracts were dried over sodium sulfate, filtered, and concentrated under reduced pressure. The product was used for the next step without further purification.

Yield: 96%

$^1$H NMR (400 MHz, CDCl$_3$) δ 7.06 (m, 1H), 6.70 (dd, 1H), 6.59 (dd, 1H), 5.34 (s, 1H), 5.16 (s, 2H), 3.76 (m, 2H), 3.49 (s, 3H), 3.27 (m, 2H), 2.63 (m, 2H), 2.34 (t, 2H), 1.91 (m, 2H), 1.70-1.40 (m, 15H). Mass Spectral Analysis m/z=460.60 (M–H)$^-$ Preparation of 3.14:

To a solution of 3.13 (2 g, 4.33 mmol, 1 eq.) in acetonitrile (50 mL) was added N,N-diisopropylethylamine (2.26 mL, 13 mmol, 3 eq.), and diethylamine 1.6 (0.9 mL, 8.66 mmol, 2 eq.). The mixture was cooled to 0° C. and O-benzotriazol-1-yl-N,N,N',N'-tetramethyluronium tetrafluoroborate (TBTU) (1.53 g, 4.76 mmol, 1.1 eq.) was added portionwise. The reaction was gradually warmed to room temperature and stirred at room temperature for 10 hours. The volatiles were removed under reduced pressure and the residue was dissolved in diethyl ether (200 mL). The organic solution was washed with saturated sodium bicarbonate (4×100 mL). The organics were then dried over sodium sulfate and concentrated in vacuo. The crude product was purified by column chromatography (eluent: ethyl acetate/hexane mixture of increasing polarity). Yield: 90%

$^1$H NMR (400 MHz, CDCl$_3$) δ 7.05 (m, 1H), 6.71 (dd, 1H), 6.59 (dd, 1H), 5.35 (s, 1H), 5.17 (s, 2H), 3.76 (m, 2H), 3.49 (s, 3H), 3.35 (q, 2H), 3.32-3.21 (m, 4H), 2.64 (m, 2H), 2.27 (t, 2H), 1.90 (m, 2H), 1.72-1.42 (m, 15H), 1.14 (t, 3H), 1.11 (t, 3H)

Mass Spectral Analysis m/z=517.62 (M+H)$^+$

Preparation of 3.15:

To a solution of 3.14 (2 g, 3.87 mmol, 1 eq.) in methanol (40 mL) was added palladium [0.4 g, 10 wt. % (dry basis) on activated carbon, 20% wt. eq.]. The reaction mixture was stirred under hydrogen atmosphere using a hydrogen balloon at room temperature for 10 hours. The palladium on activated carbon was filtered off on a celite pad and the filtrate was concentrated under reduced pressure. The crude product was purified by column chromatography (eluent: ethyl acetate/hexane mixture of increasing polarity). Yield: 98%

¹H NMR (400 MHz, CDCl₃) δ 7.02 (m, 1H), 6.65 (dd, 1H), 6.53 (dd, 1H), 5.17 (q, 2H), 3.98-3.65 (m, 2H), 3.48 (s, 3H), 3.40-3.25 (m, 5H), 3.99 (m, 2H), 2.29 (m, 2H), 2.06 (m, 1H), 1.92 (m, 1H), 1.86-1.54 (m, 7H), 1.46 (s, 9H), 1.44-1.31 (m, 3H), 1.16 (t, 3H), 1.10 (t, 3H). Mass Spectral Analysis m/z=519.65 (M+H)⁺

Preparation of 3C:

To a solution of 3.15 (1.98 g, 3.82 mmol, 1 eq.) in methanol (40 mL) was added a 4.0M anhydrous solution of hydrogen chloride in dioxane (9.5 mL, 38 mmol, 10 eq.) slowly. The mixture was stirred at room temperature for 10 hours. The organic solvents were removed under reduced pressure and the crude product was purified by column chromatography (eluent: methanol/dichloromethane mixture of increasing polarity) to give 3C isolated as its hydrochloric acid salt. Yield: 94%

¹H NMR (400 MHz, DMSO-d₆) δ 9.48 (s, 1H), 8.90-8.70 (m, 2H), 6.87 (m, 1H), 6.39 (dd, 1H), 6.30 (dd, 1H), 3.31-3.03 (m, 7H), 2.90-2.76 (m, 2H), 2.25 (m, 2H), 2.11 (m, 1H), 1.99 (m, 1H), 1.93-1.35 (m, 8H), 1.27 (m, 2H), 1.08 (t, 3H), 0.98 (t, 3H)

Mass Spectral Analysis m/z=375.8 (M+H)⁺

Example 4A

Preparation of 4.2:

To a solution of 1.1 (20 g, 44.5 mmol, 1 eq.) in dry tetrahydrofuran (300 mL) was added tetrakis(triphenylphosphine)palladium(0) (2.56 g, 2.22 mmol, 0.05 eq.) followed by a 0.5M solution of (2-cyanoethyl)zinc(II) bromide 4.1 in tetrahydrofuran (133.5 mL, 66.75 mmol, 1.5 eq.) dropwise. The reaction mixture was stirred at 45° C. for 10 hours. Additional amount of a 0.5M solution of (2-cyanoethyl)zinc(II) bromide 4.1 in tetrahydrofuran (45 mL, 22.5 mol, 0.5 eq.) was added to the reaction mixture, which was stirred at 45° C. for an additional 10 hours. The reaction mixture was quenched with saturated aqueous ammonium chloride (300 mL) and the product was extracted with diethyl ether (3×300 mL). The combined organics were washed with water, brine, dried over sodium sulfate, filtered, and concentrated under reduced pressure. The crude product was purified by column chromatography (eluent: hexane/ethyl acetate mixture of increasing polarity). Yield: 78%

¹H NMR (400 MHz, CDCl₃) δ 7.13 (m, 1H), 7.08 (dd, 1H), 6.91 (m, 2H), 5.47 (s, 1H), 3.84 (m, 2H), 3.28 (m, 2H), 2.76 (m, 2H), 2.59 (t, 2H), 1.97 (m, 2H), 1.60 (m, 2H), 1.47 (s, 9H). Mass Spectral Analysis m/z=355.36 (M+H)⁺

Preparation of 4.3:

To a solution of 4.2 (12.5 g, 35 mmol, 1 eq.) in methanol (200 mL) was added palladium [3.75 mg, 10 wt. % (dry basis) on activated carbon, 20% wt. eq.]. The reaction mixture was stirred under hydrogen atmosphere using a hydrogen balloon at room temperature for 10 hours. The palladium on activated carbon was filtered off on a celite pad and the filtrate was concentrated under reduced pressure. The crude product was used for the next step without further purification. Mass Spectral Analysis m/z=357.42 (M+H)⁺

Preparation of 4.4:

To a solution of 4.3 (11 g, 30.8 mmol, 1 eq.) in dry tetrahydrofuran (200 mL) under nitrogen was added a 2.0M solution of borane-methyl sulfide in tetrahydrofuran (154 mL, 308 mmol, 10 eq.) dropwise at 0° C. The reaction mixture was stirred at room temperature for 15 minutes and then slowly heated to reflux for 90 minutes. The volatiles were removed under reduced pressure and the residue was dissolved in methanol (100 mL). The mixture was heated under reflux for 1 hour and then concentrated to provide the crude product used for the next step without further purification.

Mass Spectral Analysis m/z=361.83 (M+H)⁺

Preparation of 4.6:

To a solution of 4.4 (0.90 g, 1.25 mmol, 1 eq.) in methylene chloride (30 mL) at 0° C. was added triethylamine (1.68 mL, 12.5 mmol) and N,N-diethylcarbamoyl chloride 4.5 (0.64 mL, 5 mmol, 4 eq.) dropwise. The reaction mixture was stirred at room temperature for 10 hours and then concentrated under reduced pressure. The residue was dissolved in ethyl acetate (200 mL). The organic solution was washed with 0.5N hydrochloric acid (3×100 mL), brine, and then concentrated in vacuo. The crude product was purified by column chromatography (eluent: hexane/ethyl acetate mixture of increasing polarity). Yield: 30%

¹H NMR (400 MHz, CDCl₃) δ 7.22 (m, 1H), 7.10 (m, 1H), 6.88 (m, 1H), 6.83 (m, 1H), 4.37 (m, 1H), 4.00-3.69 (m, 2H), 3.43-3.18 (m, 7H), 3.11-2.87 (m, 2H), 2.03-1.34 (m, 19H), 1.13 (t, 6H).

Mass Spectral Analysis m/z=460.95 (M+H)⁺

Preparation of 4A:

To a solution of 4.6 (200 mg, 0.43 mmol, 1 eq.) in methanol (15 mL) was added a 2.0M anhydrous solution of hydrogen chloride in diethyl ether (2.2 mL, 4.4 mmol, 10 eq.) dropwise. The reaction was stirred at room temperature for 10 hours and then concentrated under reduced pressure. The crude product was purified by column chromatography (eluent: methanol/dichloromethane mixture of increasing polarity) to give the 4A isolated as its hydrochloric acid salt. Yield: 83.5%

¹H NMR (400 MHz, DMSO-d₆) δ 8.92 (m, 2H), 7.28 (m, 1H), 7.10 (m, 1H), 6.89 (m, 1H), 6.82 (dd, 1H), 6.20 (s, b, 1H), 3.26-2.82 (m, 11H), 2.05-1.81 (m, 5H), 1.71 (m, 1H), 1.45 (m, 4H), 1.10 (t, 6H). Mass Spectral Analysis m/z=360.4 (M+H)⁺

Example 4B

Preparation of 4.8:

To a solution of 4.4 (1.80 g, 2.75 mmol, 1 eq.) in methylene chloride (50 mL) at 0° C. was added triethylamine (1.68 mL, 12.5 mmol, 4.5 eq.) and 2-ethylbutyryl chloride 4.7 (1.06 mL, 7.5 mmol, 2.7 eq.) dropwise. The reaction mixture was stirred at room temperature for 10 hours and then concentrated under reduced pressure. The residue was dissolved in ethyl acetate (200 mL). The organic solution was washed with 0.5N hydrochloric acid (3×100 mL), brine, and concentrated in vacuo. The crude product was purified by column chromatography (eluent: hexane/ethyl acetate mixture of increasing polarity). Yield: 87%

¹H NMR (400 MHz, CDCl₃) δ 7.20 (m, 1H), 7.10 (m, 1H), 6.88 (m, 1H), 6.83 (m, 1H), 5.46 (m, 1H), 4.01-3.70 (m, 2H), 3.32 (m, 3H), 2.96 (m, 2H), 2.01 (m, 1H), 1.89-1.71 (m, 4H), 1.69-1.35 (m, 19H), 0.89 (m, 6H). Mass Spectral Analysis m/z=459.95 (M+H)⁺

Preparation of 4B:

To a solution of 4.8 (300 mg, 0.65 mmol, 1 eq.) in methanol (20 mL) was added a 2.0M anhydrous solution of hydrogen chloride in diethyl ether (3.3 mL, 6.6 mmol, 10 eq.) dropwise. The reaction mixture was stirred at room temperature for 10 hours and then concentrated under reduced pressure. The crude product was triturated with diethyl ether and collected by filtration to give 4B isolated as its hydrochloric acid salt. Yield: 80%

¹H NMR (400 MHz, DMSO-$d_6$) δ 8.86 (m, 2H), 7.85 (t, 1H), 7.27 (m, 1H), 7.10 (m, 1H), 6.89 (m, 1H), 6.82 (m, 1H), 3.22 (m, 2H), 3.10 (m, 3H), 2.88 (m, 2H), 2.03-1.81 (m, 6H), 1.71 (m, 1H), 1.51-1.27 (m, 8H), 0.78 (m, 6H).

Mass Spectral Analysis m/z=359.4 (M+H)$^+$

Example 4C

Preparation of 4.10:

To a solution of 4.8 (0.820 g, 1.79 mmol, 1 eq.) in dry tetrahydrofuran (50 mL) at 0° C. was added sodium hydride (60% in mineral oil, 143 mg, 3.58 mmol, 2 eq.) in one portion. The mixture was stirred at 0° C. for 1 hour and then methyl iodide 4.9 (0.15 mL, 2.4 mmol, 1.3 eq.) was added dropwise. The reaction mixture was stirred at 0° C. for another 30 minutes before slowly heated at 70° C. for 10 hours. The volatiles were removed under reduced pressure and the residue was partitioned between dichloromethane (100 mL) and water (100 mL). The aqueous phase was extracted with dichloromethane (3×50 mL) and the combined organics were dried over sodium sulfate, filtered, and concentrated under reduced pressure. The crude product was purified by column chromatography (eluent: hexane/ethyl acetate mixture of increasing polarity).

Yield: 86%

¹H NMR (400 MHz, CDCl$_3$) δ 7.20 (m, 1H), 7.10 (m, 1H), 6.92-6.80 (m, 2H), 3.92 (m, 1H), 3.79 (m, 1H), 3.55-3.29 (m, 3H), 3.10-2.86 (m, 5H), 2.55-2.37 (m, 1H), 2.03-1.35 (m, 23H), 0.87 (m, 6H). Mass Spectral Analysis m/z=473.56 (M+H)$^+$ Preparation of 4C:

To a solution of 4.10 (0.72 g, 1.5 mmol, 1 eq.) in methanol (15 mL) was added a 2.0M anhydrous solution of hydrogen chloride in diethyl ether (7.5 mL, 15 mmol, 10 eq.) dropwise. The reaction mixture was stirred at room temperature for 10 hours and then concentrated under reduced pressure. The crude product was purified by column chromatography (eluent: methanol/dichloromethane mixture of increasing polarity) to give 4C isolated as its hydrochloric acid salt. Yield: 77%

¹H NMR (400 MHz, DMSO-$d_6$) δ 8.98 (m, 2H), 7.27 (m, 1H), 7.10 (m, 1H), 6.88 (m, 1H), 6.83 (m, 1H), 3.41-3.28 (m, 5H), 3.22 (m, 2H), 3.10 (m, 1H), 3.01 & 2.81 (2s, 1H), 2.90 (m, 2H), 2.06-1.81 (m, 5H), 1.73 (m, 1H), 1.60-1.29 (m, 8H), 0.83-0.70 (m, 6H)

Mass Spectral Analysis m/z=373.4 (M+H)$^+$

Example 4D

Preparation of 4.12

To a solution of 4.4 (4.70 g, 6.52 mmol, 1 eq.) in methylene chloride (100 mL) at 0° C. was added pyridine (2.64 mL, 32.6 mmol, 5 eq.) and ethanesulfonyl chloride 4.11 (1.85 mL, 19.6 mmol, 3 eq.) dropwise. The reaction mixture was stirred at room temperature for 10 hours and then concentrated under reduced pressure. The residue was dissolved in ethyl acetate (500 mL). The organic solution was washed with 0.5N hydrochloric acid (3×100 mL), brine, and concentrated in vacuo. The crude product was purified by column chromatography (eluent: hexane/ethyl acetate mixture of increasing polarity).

Yield: 37%

¹H NMR (400 MHz, CDCl$_3$) δ 7.21 (m, 1H), 7.11 (m, 1H), 6.89 (m, 1H), 6.84 (m, 1H), 4.10 (m, 1H), 4.0-3.67 (m, 2H), 3.36 (m, 1H), 3.15 (m, 2H), 3.08-2.90 (m, 4H), 2.02 (m, 1H), 1.88-1.72 (m, 3H), 1.69-1.52 (m, 6H), 1.46 (s, 9H), 1.37 (t, 3H)

Mass Spectral Analysis m/z=453.48 (M+H)$^+$

Preparation of 4D:

To a solution of 4.12 (0.42 g, 0.84 mmol, 1 eq.) in methanol (15 mL) was added a 2.0M anhydrous solution of hydrogen chloride in diethyl ether (4.2 mL, 8.4 mmol, 10 eq.) dropwise. The reaction mixture was stirred at room temperature for 10 hours and then concentrated under reduced pressure. The crude product was purified by column chromatography (eluent: methanol/dichloromethane mixture of increasing polarity) to give 4D isolated as its hydrochloric acid salt. Yield: 74%

¹H NMR (400 MHz, DMSO-$d_6$) δ 8.98 (m, 2H), 7.31 (m, 1H), 7.09 (m, 2H), 6.90 (m, 1H), 6.83 (m, 1H), 3.26-3.06 (m, 3H), 3.02-2.82 (m, 6H), 2.08-1.82 (m, 5H), 1.73 (m, 1H), 1.56-1.39 (m, 4H), 1.13 (t, 3H). Mass Spectral Analysis m/z=353.3 (M+H)$^+$

Example 4E

Preparation of 4.13:

To a solution of 4.12 (0.80 g, 1.6 mmol, 1 eq.) in dry tetrahydrofuran (50 mL) at 0° C. was added sodium hydride (60% in mineral oil, 130 mg, 3.2 mmol, 2 eq.) in one portion. The mixture was stirred at 0° C. for 1 hour and then methyl iodide 4.9 (0.13 mL, 2.1 mmol, 1.3 eq.) was added dropwise. The reaction mixture was stirred at 0° C. for another 30 minutes before slowly heated at 70° C. for 10 hours. The volatiles were removed under reduced pressure and the residue was partitioned between dichloromethane (100 mL) and water (100 mL). The aqueous phase was extracted with dichloromethane (3×50 mL) and the combined organics were dried over sodium sulfate, filtered, and concentrated under reduced pressure. The crude product was purified by column chromatography (eluent: hexane/ethyl acetate mixture of increasing polarity).

Yield: 96%

¹H NMR (400 MHz, CDCl$_3$) δ 7.23 (m, 1H), 7.10 (m, 1H), 6.89 (m, 1H), 6.83 (dd, 1H), 3.93 (m, 1H), 3.79 (m, 1H), 3.36 (m, 1H), 3.22 (m, 2H), 3.98 (m, 4H), 2.86 (s, 3H), 2.00 (m, 1H), 1.89-1.73 (m, 3H), 1.70-1.52 (m, 5H), 1.46 (s, 9H), 1.41 (m, 1H), 1.35 (t, 3H)

Mass Spectral Analysis m/z=467.41 (M+H)$^+$

Preparation of 4E:

To a solution of 4.13 (0.72 g, 1.5 mmol, 1 eq.) in methanol (30 mL) was added a 2.0M anhydrous solution of hydrogen chloride in diethyl ether (7.6 mL, 15.2 mmol, 10 eq.) slowly. The reaction mixture was stirred at room temperature for 10 hours and then concentrated under reduced pressure. The crude product was purified by column chromatography (eluent: methanol/dichloromethane mixture of increasing polarity) to give 4E isolated as its hydrochloric acid salt. Yield: 91%

¹H NMR (400 MHz, DMSO-$d_6$) δ 8.76 (m, 2H), 7.29 (m, 1H), 7.10 (m, 1H), 6.90 (m, 1H), 6.83 (m, 1H), 3.23 (m, 2H), 3.18-3.02 (m, 5H), 2.90 (m, 2H), 2.77 (s, 3H), 2.08-1.81 (m, 5H), 1.76-1.37 (m, 5H), 1.19 (t, 3H). Mass Spectral Analysis m/z=367.7 (M+H)$^+$

Example 5A

Preparation of 5.6:

To a suspension of NaH (2.53 g, 95%, 0.1 mol) in THF (300 mL) at 0° C. was added dropwise triethyl phosphonoacetate (5.2) (20 mL, 0.1 mol). The reaction mixture was then stirred at room temperature for 45 minutes and then the spiroketone 5.1 (12.68 g, 0.03995 mol) was added in small portions to the mixture. The reaction mixture was stirred at ~50° C. for 16 days. The reaction was quenched with water and extracted with ethyl acetate. The combined extracts were washed with brine, dried over sodium sulfate and concentrated in vacuo. The residue was chromatographed using ethyl acetate/hexane (1:3) as eluent to give 14 g of a mixture of three very close spots corresponding to the three isomeric olefins 5.3, 5.4 and 5.5. The mixture of olefins (14 g) in ethyl acetate (450 mL) was hydrogenated in the presence of 10% Pd/C (4.2 g) at room temperature for 3 days. Filtration followed by evaporation of the solvent gave the saturated ester 5.6. Yield: 90% (2 steps)

$^1$H NMR (400 MHz, CDCl$_3$) δ 7.17 (m, 2H), 6.90 (m, 2H), 4.20 (q, 2H), 3.88 (m, 2H), 3.40 (m, 2H), 3.08 (m, 1H), 3.00 (dd, 1H), 2.40 (dd, 1H), 2.00 (m, 1H), 1.86-1.63 (m, 4H), 1.46 (s+m, 10H), 1.29 (t, 3H).

Preparation of 5.7:

To a solution of ester 5.6 (2.0 g, 5.1 mol) in a mixture of methanol (30 mL), tetrahydrofuran (30 mL) and water (30 mL) was added lithium hydroxide monohydrate (1.35 g, 32 mmol). The reaction mixture was stirred at room temperature overnight, then concentrated in vacuo, and the aqueous phase was washed with diethyl ether. The aqueous layer was acidified with 1N HCl to pH ~4 and extracted with methylene chloride. The combined organic extracts were dried over sodium sulfate, filtered and concentrated in vacuo to give the desired carboxylic acid. Yield: 100%.

$^1$H NMR (400 MHz, DMSO d$_6$) δ7.26 (m, 1H), 7.10 (m, 1H), 6.86 (m, 1H), 6.90 (m, 1H), 3.75 (m, 1H), 3.63 (m, 1H), 3.22 (m, 2H), 2.93 (m, 2H), 2.32 (dd, 1H), 2.0 (m, 1H), 2.68-2.52 (m, 4H), 1.40 (s+m, 10H).

Preparation of 5.8:

To a solution of the carboxylic acid 5.7 (433 mg, 1.2 mmol) in acetonitrile (15 mL) was added N,N-diisopropylethylamine (0.86 mL, 4.9 mmol) and diethylamine (1.6) (0.36 mL, 3.5 mmol). The reaction mixture was cooled with ice-bath and TBTU (463 mg, 1.44 mmol) was added portionwise to the reaction mixture. The reaction mixture was stirred at room temperature overnight. The reaction mixture was concentrated, dissolved in ethyl acetate. The organic solution was washed with saturated aqueous sodium bicarbonate and dried over sodium sulfate. Evaporation of the solvent gave the crude product, which was chromatographed using ethyl acetate/hexane (1:1) as eluent. Yield: 80%.

$^1$H NMR (400 MHz, CDCl$_3$) δ 7.20 (m, 1H), 7.10 (m, 1H), 6.88 (m, 2H), 3.81 (m, 2H), 3.56-3.30 (m, 6H), 3.08 (m, 1H), 2.92 (dd, 1H), 2.40 (dd, 1H), 2.12 (m, 1H), 1.83-1.62 (m, 3H), 1.48 (s+m, 11H), 1.20 (t, 3H).

Preparation of 5A:

To the solution of 5.8 (380 mg, 0.91 mmol) in methylene chloride (5 mL) was added a 2.0M anhydrous solution of hydrogen chloride in diethyl ether (15 mL). The reaction mixture was stirred for 6 hours at room temperature. Diethyl ether (80 mL) was added to the reaction mixture, which was stirred at room temperature for 2 days. The upper clear solution was decanted, the residue was washed with diethyl ether three times and dissolved in methylene chloride. The resulting solution was concentrated in vacuo. The residue was dried in vacuo to yield 5A isolated as its hydrochloric acid salt. Yield: 93%.

$^1$H NMR (400 MHz, DMSO d$_6$) δ 9.08 (brs, 2H), 7.28 (m, 1H), 7.10 (m, 1H), 6.85 (m, 2H), 3.32-2.95 (m, 10H), 2.40 (m, 1H), 2.02-1.72 (m, 5H), 1.50 (m, 1H), 1.10 (m, 6H).

Mass Spectral Analysis m/z=317.3 (M+H)$^+$

Example 5B

Preparation of 5.10:

To a solution of the carboxylic acid 5.7 (866 mg, 2.4 mmol) in acetonitrile (40 mL) was added N,N-diisopropylethylamine (2.6 mL, 15 mmol) and glycine methyl ester hydrochloride (5.9) (480 mg, 3.8 mmol). The reaction mixture was cooled with ice-bath and TBTU (930 mg, 2.9 mmol) was added in small portions to the reaction mixture. The reaction mixture was stirred at room temperature overnight. The reaction mixture was concentrated and dissolved in ethyl acetate. The organic solution was washed with saturated aqueous sodium bicarbonate and dried over sodium sulfate. Evaporation of the solvent provided the crude product, which was chromatographed using ethyl acetate/hexane (2:1) as eluent to yield the product 5.10.

Yield: 94%.

$^1$H NMR (400 MHz, CDCl$_3$) δ 7.20 (m, 1H), 7.12 (m, 1H), 6.90 (m, 2H), 6.00 (brs, 1H), 4.09 (d, 2H), 3.90 (m, 1H), 3.78 (s+m, 4H), 3.48 (m, 1H), 3.33 (m, 1H), 3.03 (m, 1H), 2.96 (dd, 1H), 2.29 (dd, 1H), 2.03 (m, 1H), 2.83-2.57 (m, 4H), 1.48 (s+m, 10H).

Preparation of 5.11:

To a solution of 5.10 (970 mg, 2.2 mmol) in a mixture of methanol (15 mL), tetrahydrofuran (15 mL) and water (15 mL) was added lithium hydroxide monohydrate (588 mg, 14 mmol). The reaction mixture was stirred at room temperature overnight, concentrated in vacuo, and extracted with diethyl ether. The aqueous layer was acidified with 1N HCl to pH ~4, and extracted with methylene chloride. The combined organic extracts were dried over sodium sulfate and concentrated in vacuo to give the desired carboxylic acid. Yield: 100%.

$^1$H NMR (400 MHz, DMSO d$_6$) δ12.58 (s, 1H), 8.36 (t, 1H), 7.30 (m, 1H), 7.09 (m, 1H), 6.80 (m, 2H), 3.80-3.60 (m, 4H), 3.30 (m, 2H), 3.02 (m, 1H), 2.86 (dd, 1H), 2.19 (dd, 1H), 2.05 (m, 1H), 2.65 (m, 3H), 1.40 (s+m, 11H).

Preparation of 5.12:

To a solution of the carboxylic acid 5.11 (920 mg, 2.2 mmol) in acetonitrile (30 mL) was added N,N-diisopropylethylamine (1.6 mL, 9.0 mmol) and diethylamine (1.6) (0.66 mL, 6.4 mmol). The reaction mixture was cooled with ice-bath and TBTU (850 mg, 2.6 mmol) was added in small portions to the reaction mixture. The reaction mixture was stirred at room temperature overnight. The reaction mixture was concentrated and dissolved in ethyl acetate. The resulting organic solution was washed with saturated aqueous sodium bicarbonate and dried over sodium sulfate. Evaporation of the solvent provided the crude product, which was chromatographed using acetone/hexane (1:2) as eluent. Yield: 87%.

$^1$H NMR (400 MHz, CDCl$_3$) δ 7.20 (m, 1H), 7.10 (m, 1H), 6.89 (m, 2H), 6.76 (m, 1H), 4.15 (d, 1H), 4.08 (d, 1H), 3.80 (m, 2H), 3.40-3.30 (m, 6H), 3.0 (m, 2H), 2.28 (dd, 1H), 2.0 (m, 1H), 1.78 (m, 2H), 1.58 (m, 2H), 1.47 (s+m, 10H), 1.21 (t, 3H), 1.12 (t, 3H).

Preparation of 5B:

To a solution of compound 5.12 (880 mg, 1.8 mmol) in methylene chloride (10 mL) was added a 2.0M anhydrous solution of hydrogen chloride in diethyl ether (30 mL). The reaction mixture was stirred for 6 hours at room temperature. Diethyl ether (120 ml) was added to the reaction mixture, which was stirred at room temperature for 2 days. The upper clear solution was decanted and the residue was washed with diethyl ether three times and dissolved in methylene chloride.

The resulting solution was concentrated in vacuo. The product was then dried in vacuo to yield 5B isolated as its hydrochloric acid salt. Yield: 96%.

$^1$H NMR (400 MHz, DMSO d$_6$) δ 9.10 (brs, 2H), 8.18 (t, 1H), 7.31 (m, 1H), 7.10 (m, 1H), 6.88 (m, 2H), 3.98 (m, 2H), 3.50-3.10 (m, 8H), 2.90 (m, 2H), 2.20 (dd, 1H), 2.0-1.70 (m, 5H), 1.52 (t, 1H), 1.12 (t, 3H), 1.02 (t, 3H). Mass Spectral Analysis m/z=374.3 (M+H)$^+$ Example 6A Preparation of 6.1:

To a solution of ester 5.6 (2.5 g, 6.4 mmol) in tetrahydrofuran (120 mL) was added lithium tetrahydroborate (450 mg, 20 mmol). The reaction mixture was refluxed overnight and quenched with water followed by 1N HCl in order to adjust the pH to 3-4. The mixture was extracted with ethyl acetate. The combined organic extracts were dried over sodium sulfate and concentrated to give the alcohol 6.1 used for the next step without further purification. Yield: 100%.

$^1$H NMR (400 MHz, CDCl$_3$) δ 7.24 (m, 1H), 7.10 (m, 1H), 6.83 (m, 2H), 3.90-3.80 (m, 4H), 3.37 (m, 1H), 3.18 (m, 2H), 2.33 (m, 1H), 1.96-1.58 (m, 6H), 1.47 (s+m, 11H).

$^1$H NMR (400 MHz, DMSO d$_6$) δ 7.51 (s, 1H), 7.29 (t, 1H), 7.22 (s, 4H), 7.10 (d, 1H), 7.05 (d, 1H), 6.97 (s, 1H), 5.90 (s, 1H), 3.63 (m, 2H), 3.41 (m, 2H), 3.32 (m, 2H), 3.20 (m, 2H), 1.80 (m, 4H), 1.42 (s, 9H), 1.10 (m, 6H).

Preparation of 6.3:

A solution of ethyl diazoacetate (6.2) (1.22 mL, 11.6 mmol) in methylene chloride (10 mL) was added dropwise to a solution of the alcohol 6.1 (1.15 g, 3.31 mmol) and rhodium (II) acetate dimer (16 mg, 0.036 mmol) in methylene chloride (20 mL) at room temperature. The reaction mixture was stirred at room temperature overnight. The reaction mixture was concentrated in vacuo and the residue was purified by column chromatography using ethyl acetate/hexane (1:4) as eluent, yielding the ester 6.3. Yield: 60%.

$^1$H NMR (400 MHz, CDCl$_3$) δ 7.26 (m, 1H), 7.10 (m, 1H), 6.86 (m, 2H), 4.21 (q, 2H), 4.11 (d, 1H), 4.04 (d, 1H), 3.88 (m, 2H), 3.65 (m, 2H), 3.38 (m, 1H), 3.10 (m, 2H), 2.43 (m, 1H), 2.01 (dd, 1H), 1.83-1.58 (m, 4H), 1.48 (s+m, 1H).

Preparation of 6.4:

To a solution of the ester 6.3 (1.12 g, 2.58 mmol) in a mixture of methanol (20 mL), tetrahydrofuran (20 mL) and water (20 mL) was added lithium hydroxide monohydrate (672 mg, 16 mmol). The reaction mixture was stirred at room temperature overnight, concentrated in vacuo and extracted with diethyl ether. The aqueous layer was acidified with 1N HCl to pH ~4, and extracted with methylene chloride. The combined organic extracts were dried over sodium sulfate and concentrated in vacuo to give the carboxylic acid 6.4 used for the next step without further purification. Yield: 99.3%.

$^1$H NMR (400 MHz, DMSO d$_6$) δ 12.60 (s, 1H), 7.30 (m, 1H), 7.08 (m, 1H), 6.88 (m, 1H), 6.79 (m, 1H), 4.07 (d, 1H), 3.99 (d, 1H), 3.70 (m, 1H), 3.58 (m, 3H), 3.30 (m, 1H), 3.0 (m, 2H), 2.32 (m, 1H), 2.15 (m, 1H), 1.60 (m, 4H), 1.40 (s+m, 11H).

Preparation of 6.5:

To a solution of the carboxylic acid 6.4 (609 mg, 1.5 mmol) in acetonitrile (25 mL) was added N,N-diisopropylethylamine (1.1 mL, 6.2 mmol) and diethylamine (1.6) (0.45 mL, 4.4 mmol). The reaction mixture was cooled with ice-bath and TBTU (580 mg, 0.0018 mol) was added in small portions. The reaction mixture was stirred at room temperature overnight. The reaction mixture was concentrated in vacuo; the residue was dissolved in ethyl acetate and the resulting solution was washed with saturated aqueous sodium bicarbonate and dried over sodium sulfate. Evaporation of the solvent provided the crude product, which was chromatographed using ethyl acetate/hexane (1:1) as eluent. Yield: 68%.

$^1$H NMR (400 MHz, CDCl$_3$) δ 7.26 (m, 1H), 7.10 (m, 1H), 6.85 (m, 2H), 4.07 (d, 1H), 4.0 (d, 1H), 3.86 (m, 2H), 3.62 (m, 2H), 3.40-3.30 (m, 5H), 3.05 (m, 2H), 2.42 (m, 1H), 1.98 (m, 1H), 1.77 (m, 3H), 1.56 (t, 1H), 1.43 (s+m, 1H), 1.20 (t, 3H), 1.13 (t, 3H).

Preparation of 6A:

To a solution of 6.5 (450 mg, 0.98 mmol) in methylene chloride (6 mL) was added a 2.0M anhydrous solution of hydrogen chloride in diethyl ether (20 mL). The reaction was stirred for 6 hours at room temperature. Diethyl ether (80 mL) was added to the reaction mixture, which was stirred at room temperature for 2 days. The upper clear solution was decanted and the residue was washed with diethyl ether three times, dissolved in methylene chloride and the resulting solution was concentrated and dried in vacuo to yield 6A isolated as its hydrochloric acid salt. Yield: 94%.

$^1$H NMR (400 MHz, DMSO d$_6$) δ 9.04 (brs, 2H), 7.30 (m, 1H), 7.10 (m, 1H), 6.90 (m, 1H), 6.80 (m, 1H), 4.15 (d, 1H), 4.1 (d, 1H), 3.53 (m, 2H), 3.22-2.90 (m, 9H), 2.36 (m, 1H), 2.13 (m, 1H), 1.90-1.50 (m, 6H), 1.10 (t, 3H), 1.02 (t, 3H).

Mass Spectral Analysis m/z=361.4 (M+H)$^+$

Example 7A

Preparation of 7.2:

To a solution of 7.1 (4 g, 8.6 mmol, 1 eq.) in dry tetrahydrofuran (90 mL) was added tetrakis(triphenylphosphine) palladium(0) (497 mg, 0.43 mmol, 0.05 eq.) followed by a 0.5M solution of (5-ethoxy-5-oxopentyl)zinc(II) bromide 2.6 in tetrahydrofuran (27.5 mL, 13.7 mmol, 1.6 eq.) dropwise. The reaction mixture was stirred at 45° C. for 10 hours and then quenched with aqueous ammonium chloride (100 mL) at room temperature. The product was extracted with diethyl ether (3×100 mL) and the combined extracts were washed with brine, dried over sodium sulfate, filtered, and concentrated under reduced pressure. The crude product was purified by column chromatography (eluent: hexane/ethyl acetate mixture of increasing polarity).

Yield: 58%.

$^1$H NMR (400 MHz, CDCl$_3$) δ 7.06 (m, 1H), 6.92 (m, 1H), 6.83 (m, 1H), 5.79 (s, 1H), 4.13 (q, 2H), 3.64-3.28 (m, 4H), 2.64 (s, 2H), 2.41 (t, 2H), 2.33 (t, 2H), 1.74-1.35 (m, 17H), 1.25 (t, 3H).

Mass Spectral Analysis m/z=446.85 (M+H)$^+$

Preparation of 7.3:

To a solution of 7.2 (2.2 g, 4.9 mmol, 1 eq.) in ethyl acetate (50 mL) was added palladium [440 mg, 10 wt. % (dry basis) on activated carbon, 20% wt. eq.]. The reaction mixture was stirred under hydrogen atmosphere using a hydrogen balloon at room temperature for 10 hours. The palladium on activated carbon was filtered off on a celite pad and the filtrate was concentrated under reduced pressure. The crude product was purified by column chromatography (eluent: ethyl acetate/hexane mixture of increasing polarity). Yield: 73%

$^1$H NMR (400 MHz, CDCl$_3$) δ 7.01-6.92 (m, 2H), 6.80 (m, 1H), 4.13 (q, 2H), 3.52 (m, 1H), 3.41 (m, 2H), 3.29 (m, 1H), 2.79 (m, 1H), 2.66 (m, 1H), 2.47 (m, 1H), 2.32 (m, 2H), 1.89 (m, 2H), 1.76-1.29 (m, 19H), 1.25 (t, 3H).

Mass Spectral Analysis m/z=448.86 (M+H)$^+$

Preparation of 7.4:

To a solution of 7.3 (1.6 g, 3.6 mmol, 1 eq.) in a mixture of methanol (20 mL), tetrahydrofuran (20 mL) and water (20 mL) was added lithium hydroxide monohydrate (0.61 g, 14.5 mmol, 4 eq.) in one portion. The reaction mixture was stirred at room temperature for 10 hours. The volatiles were removed under reduced pressure and the remaining aqueous solution was acidified with 1N hydrochloric acid until pH 2~3. The product was extracted with dichloromethane (3×100 mL) and the combined organics were dried over sodium sulfate, filtered, and concentrated under reduced pressure. The product was used for the next step without further purification. Yield: 80%

$^1$H NMR (400 MHz, CDCl$_3$) δ 7.00-6.89 (m, 2H), 6.78 (m, 1H), 3.49 (m, 1H), 3.39 (m, 2H), 3.28 (m, 1H), 2.75 (m, 1H), 2.64 (m, 1H), 2.46 (m, 1H), 2.31 (m, 2H), 1.87 (m, 2H), 1.73-1.12 (m, 19H). Mass Spectral Analysis m/z=418.87 (M−H)$^−$ Preparation of 7A:

To a solution of 7.4 (0.3 g, 0.7 mmol, 1 eq.) in dichloromethane (15 mL) was slowly added a 2.0M anhydrous solution of hydrogen chloride in diethyl ether (2.1 mL, 4.2 mmol, 6 eq.). The mixture was stirred at room temperature for 10 hours and additional amount of a 2.0M anhydrous solution of hydrogen chloride in diethyl ether (2 mL, 4 mmol, 5.7 eq.) was added to the reaction mixture. The mixture was stirred at room temperature for another 10 hours and then concentrated under reduced pressure to give the crude product as the acid. The crude acid was purified by column chromatography (eluent: methanol/dichloromethane mixture of increasing polarity). During the purification and drying steps, the acid converted to the methyl ester, 7A, isolated as its hydrochloric acid salt. Yield: 81%

$^1$H NMR (400 MHz, DMSO-d$_6$) δ 8.60 (s, b, 2H), 7.10 (m, 2H), 6.93 (m, 1H), 3.58 (s, 3H), 3.11 (m, 2H), 2.98 (m, 2H), 2.75 (m, 2H), 2.48 (m, 1H), 2.33 (m, 2H), 1.88 (m, 2H), 1.65-1.13 (m, 10H). Mass Spectral Analysis m/z=334.3 (M+H)$^+$ Example 7B Preparation of 7.5:

To a solution of 7.4 (1.2 g, 2.86 mmol, 1 eq.) in acetonitrile (30 mL) was slowly added diisopropylethylamine (1.09 mL, 6.3 mmol, 2.2 eq.), diethylamine 1.6 (0.6 mL, 5.72 mmol, 2 eq.) at room temperature and 10 minutes later at 0° C., O-benzotriazol-1-yl-N,N,N',N'-tetramethyluronium tetrafluoroborate (TBTU) (1.01 g, 3.15 mmol, 1.1 eq.) portionwise. The reaction mixture was slowly warmed to room temperature and stirred at room temperature for 10 hours. The volatiles were removed under reduced pressure and the residue was dissolved in ethyl acetate (200 mL). The resulting solution was washed with 1M aqueous sodium bicarbonate (3×50 mL), brine, dried over sodium sulfate, filtered, and concentrated under reduced pressure. The crude product was purified by column chromatography (eluent: hexane/ethyl acetate mixture of increasing polarity). Yield: 88%

$^1$H NMR (400 MHz, CDCl$_3$) δ 6.97 (m, 2H), 6.79 (m, 1H), 3.57-3.24 (m, 8H), 2.79 (m, 1H), 2.65 (m, 1H), 2.48 (m, 1H), 2.31 (m, 2H), 1.90 (m, 2H), 1.80-1.53 (m, 3H), 1.50-1.19 (m, 16H), 1.17 (t, 3H), 1.11 (t, 3H). Mass Spectral Analysis m/z=475.53 (M+H)$^+$ Preparation of 7B:

The reaction mixture was stirred under hydrogen atmosphere using a hydrogen balloon at room temperature for 10 hours. The palladium on activated carbon was filtered off on a celite pad and the filtrate was concentrated under reduced pressure. The crude product was purified by column chromatography (eluent: ethyl acetate/hexane mixture of increasing polarity) to give 8A isolated as its hydrochloric acid salt. Yield: 53%

$^1$H NMR (400 MHz, CDCl$_3$) δ 6.92 (dd, 1H), 6.83-6.78 (m, 2H), 4.01-3.69 (m, 2H), 3.43-3.25 (m, 5H), 3.08-2.80 (m, 2H), 2.32 (m, 2H), 1.95 (m, 1H), 1.86 (m, 1H), 1.82-1.60 (m, 5H), 1.57-1.31 (m, 14H), 1.17 (t, 3H), 1.11 (t, 3H). Mass Spectral Analysis m/z=357.4 (M+H)$^+$ Example 8B Preparation of 8.6:

To a solution of the enol triflate 8.5 (40.0 g, 78.2 mmol) in tetrahydrofuran (300 mL) at room temperature was added a 0.5M solution of 5-ethoxy-5-oxopentylzinc bromide (2.6) in tetrahydrofuran (200 mL, 100 mmol) followed by tetrakis(triphenylphosphine)palladium(0) (4.1 g, 3.5 mmol). The reaction mixture was stirred at 50° C. overnight. Additional amount of a 0.5M solution of 5-ethoxy-5-oxopentylzinc bromide (2.6) in tetrahydrofuran (160 mL, 80 mmol) was added to the reaction mixture, which was stirred at 50° C. for an additional 24 hours. The reaction mixture was cooled to room temperature, quenched with water and extracted with ethyl acetate. The combined organic extracts were dried over sodium sulfate and concentrated in vacuo. The residue was chromatographed using ethyl acetate:hexane (1:3) as eluent.

Yield: 78.3%.

$^1$H NMR (400 MHz, CDCl$_3$) δ 7.26 (m, 7.35 (m, 5H), 7.02 (d, 1H), 6.80 (d, 1H), 6.68 (dd, 1H), 5.72 (s, 1H), 5.13 (s, 2H), 4.10 (q, 2H), 3.80 (s, 3H), 3.58 (m, 2H), 3.43 (m, 2H), 2.60 (s, 2H), 2.43 (t, 2H), 2.30 (t, 2H), 1.70-1.40 (m, 8H), 1.23 (t, 3H).

Preparation of 8.7:

To a solution of 8.6 (30.0 g, 61.02 mmol) in a mixture of methanol-tetrahydrofuran-water (300 mL-300 mL-300 mL) was added lithium hydroxide monohydrate (16 g, 38 mmol). The reaction mixture was stirred at room temperature overnight, concentrated in vacuo and extracted with diethyl ether. The aqueous layer was acidified with 1N HCl to pH ~4, extracted with methylene chloride. The combined organic extracts were dried over sodium sulfate and concentrated to give the carboxylic acid 8.7, used for the next step without further purification.

Yield: 98.8%.

$^1$H NMR (400 MHz, DMSO d$_6$) δ 12.0 (brs, 1H), 7.32 (m, 5H), 7.10 (d, 1H), 6.80 (d, 1H), 6.71 (dd, 1H), 5.82 (s, 1H), 5.08 (s, 2H), 3.73 (s, 3H), 3.48-3.38 (m, 4H), 2.60 (s, 2H), 2.40 (t, 2H), 2.25 (t, 2H), 1.53-1.32 (m, 8H).

To a solution of the carboxylic acid 8.7 (27.96 g, 60.32 mol) in acetonitrile (600 mL) was added N,N-diisopropylethylamine (41.0 mL, 233 mmol) and diethylamine (17.0 mL, 163.5 mmol). The reaction mixture was cooled with ice-bath and TBTU (25.2 g, 78.5 mol) was added in small portions to the reaction mixture. The reaction mixture was stirred at room temperature overnight. The reaction mixture was concentrated and dissolved in ethyl acetate. The resulting solution was washed with saturated aqueous sodium bicarbonate and dried over sodium sulfate. Evaporation of the solvent provided the crude product, which was chromatographed using ethyl acetate/hexane (2:1) as eluent to yield the amide 8.8. Yield: 96.5%.

$^1$H NMR (400 MHz, CDCl$_3$) δ 7.33 (m, 5H), 7.03 (d, 1H), 6.82 (d, 1H), 6.70 (dd, 1H), 5.72 (s, 1H), 5.12 (s, 2H), 3.80 (s,

3H), 3.60 (m, 2H), 3.42-3.30 (m, 6H), 2.60 (s, 2H), 2.45 (t, 2H), 2.30 (t, 2H), 2.70 (m, 2H), 1.58-1.42 (m, 6H), 1.15 (t, 3H), 1.10 (t, 3H).

Preparation of 8B:

Compound 8.8 (569 mg, 1.1 mmol) was dissolved in methanol (30 mL) and the solution was hydrogenated in the presence of 10% Pd/C (180 mg) at room temperature for 2 days. The reaction mixture was filtered and the filtrate was concentrated in vacuo. The residue was purified by column chromatography using methylene chloride/methanol/ammonium hydroxide (10:1:1) as eluent to give 8B. Yield: 100%.

$^1$H NMR (400 MHz, CDCl$_3$) δ 6.97 (d, 1H), 6.80 (d, 1H), 6.68 (dd, 1H), 3.79 (s, 3H), 3.38 (q, 2H), 3.30 (q, 2H), 2.90-2.70 (m, 6H), 2.42 (d, 1H), 2.30 (m, 2H), 1.92 (m, 2H), 1.68 (m, 4H), 1.38 (m, 7H), 1.18 (t, 3H), 1.10 (t, 3H).

Mass Spectral Analysis m/z=387.4 (M+H)$^+$

Example 8C

Preparation of 8C:

To a solution of compound 8.8 in methylene chloride at −50° C. was added dropwise a 1.0M solution of boron tribromide in methylene chloride (12 mL, 12 mmol). The reaction mixture was stirred between −50° C. to −10° C. for 1 hour and then at room temperature overnight. The reaction mixture was cooled to 0° C., quenched with 1N HCl and the mixture was extracted with diethyl ether. The aqueous layer was basified with 3N sodium hydroxide to pH ~9, and extracted with methylene chloride. The organic extracts were combined, dried over sodium sulfate, and concentrated in vacuo. The crude compound 8.9 was dissolved in methanol (50 mL) and the solution was hydrogenated in the presence of 10% Pd/C (200 mg) for 2 days. The reaction mixture was filtered and the filtrate was concentrated in vacuo. The residue was purified by column chromatography using methylene chloride/methanol/ammonia hydroxide (8:1:1) as eluent to yield 8C. Yield: 53.5% (two steps).

$^1$H NMR (400 MHz, CDCl$_3$) δ 6.90 (d, 1H), 6.78 (d, 1H), 6.60 (dd, 1H), 4.70 (brs, 1H), 3.38 (q, 2H), 3.30 (q, 2H), 2.90 (m, 2H), 2.77 (m, 3H), 2.63 (d, 1H), 2.40 (d, 1H), 2.30 (t, 2H), 1.90 (m, 2H), 1.65 (m, 3H), 1.40 (m, 6H), 1.18-1.10 (m, 8H).

Mass Spectral Analysis m/z=373.4 (M+H)$^+$

Example 9A

Preparation of 9.1:

Crude 8.9 prepared from 8.8 (30.2 g, 58.2 mmol) was dissolved in methylene chloride (600 mL) and to this solution was added triethylamine (13 mL, 93 mmol) followed by di-tert-butyldicarbonate (12.8 g, 58.8 mmol). The reaction mixture was stirred for 1 hour at room temperature and concentrated in vacuo. The residue was chromatographed using ethyl acetate/methylene chloride (1:1) as eluent to yield the phenol 9.1. Yield: 66.4% (two steps).

$^1$H NMR (400 MHz, CDCl$_3$) δ 6.98 (d, 1H), 6.87 (d, 1H), 6.73 (s, 1H), 6.68 (dd, 1H), 5.70 (s, 1H), 3.46-3.30 (m, 8H), 2.60 (s, 2H), 2.40 (t, 2H), 2.32 (t, 2H), 1.73 (m, 2H), 1.58-1.40 (m, 15H), 1.18 (t, 3H), 1.10 (t, 3H).

Preparation of 9.2:

A solution of compound 9.1 (15.0 g, 31.87 mmol) in ethyl acetate (600 mL) was hydrogenated in the presence of 10% Pd/C (4.5 g) at room temperature for 2 days. The mixture was filtered through celite. The filtrate was evaporated under reduced pressure. The crude product was purified by chromatography using ethyl acetate:hexane (1:1) as eluent. Yield: 95%.

$^1$H NMR (400 MHz, CDCl$_3$) δ 6.98 (d, 1H), 6.87 (d, 1H), 6.73 (s, 1H), 6.68 (dd, 1H), 6.92 (s, 1H), 6.88 (d, 1H), 6.82 (d, 1H), 6.62 (dd, 1H), 3.50 (m, 1H), 3.35 (m, 7H), 2.72 (m, 1H), 2.60 (d, 1H), 2.40 (d, 1H), 2.31 (t, 2H), 1.85-1.56 (m, 6H), 1.46 (s, 9H), 1.40-1.30 (m, 6H), 1.20 (t, 3H), 1.12 (t, 3H).

Preparation of 9.3:

To a solution of the phenol 9.2 (3.21 g, 6.8 mmol) in methylene chloride (100 mL) was added triethylamine (2.37 mL, 17 mmol), 4-dimethylaminopyridine (DMAP) (83 mg, 0.68 mol), followed by N-phenylbis(trifluoromethanesulphonimide) (7.9) (3.3 g, 9.2 mmol). The reaction mixture was stirred at room temperature overnight. The reaction mixture was washed with aqueous saturated sodium bicarbonate, dried over sodium sulfate and concentrated in vacuo. The residue was chromatographed using ethyl acetate:hexane (1:1) as eluent, yielding the triflate 9.3.

Yield: 92.5%.

$^1$H NMR (400 MHz, CDCl$_3$) δ 7.10 (m, 1H), 7.0 (dd, 1H), 3.50-3.27 (m, 8H), 2.82 (m, 1H), 2.70 (d, 1H), 2.50 (d, 1H), 2.30 (m, 2H), 1.90 (m, 2H), 1.62 (m, 4H), 1.45 (s, 9H), 1.38-1.28 (m, 6H), 1.20 (t, 3H), 1.10 (t, 3H).

Preparation of 9.4:

To a solution of the triflate 9.3 (3.75 g, 6.2 mmol) in N,N-dimethylformamide (25 mL) was added methanol (10 mL), triethylamine (1.4 mL, 10 mol), 1,3-bis(diphenylphosphino)propane (207 mg, 0.502 mmol) followed by palladium acetate (113 mg, 0.503 mol). The reaction mixture was heated to ~65° C. and carbon monoxide was bubbled through the reaction solution for 4 hours. The reaction mixture was then cooled to room temperature, diluted with diethyl ether and washed with water, brine, dried over sodium sulfate, and concentrated in vacuo. The residue was purified by column chromatography using ethyl acetate:hexane (2:1) as eluent to give the methyl ester 9.4. Yield: 84.6%.

$^1$H NMR (400 MHz, CDCl$_3$) δ 7.93 (d, 1H), 7.73 (dd, 1H), 7.10 (d, 1H), 3.90 (s, 3H), 3.50-3.30 (m, 8H), 2.85 (m, 1H), 2.72 (d, 1H), 2.58 (d, 1H), 2.31 (m, 2H), 2.00 (m, 2H), 1.68 (m, 4H), 1.45 (s, 9H), 1.40-1.28 (m, 6H), 1.19 (t, 3H), 1.11 (t, 3H).

Preparation of 9.5:

To a solution of compound 9.4 (2.6 g, 5.05 mmol) in a mixture of methanol (40 mL), tetrahydrofuran (40 mL) and water (40 mL) was added lithium hydroxide monohydrate (1.35 g, 32 mmol). The reaction mixture was stirred at room temperature overnight, concentrated in vacuo and extracted with diethyl ether. The aqueous layer was acidified with 1N HCl to pH ~4, and extracted with methylene chloride. The combined organic extracts were dried over sodium sulfate and concentrated to give the carboxylic acid 9.5 used for the next step without further purification. Yield: 93.7%.

$^1$H NMR (400 MHz, CDCl$_3$) δ 8.0 (d, 1H), 7.8 (dd, 1H), 7.10 (d, 1H), 3.50-3.30 (m, 8H), 2.82 (m, 1H), 2.71 (d, 1H), 2.58 (d, 1H), 2.35 (m, 2H), 2.00 (m, 2H), 1.70 (m, 4H), 1.44 (s, 9H), 1.40-1.28 (m, 6H), 1.20 (t, 3H), 1.10 (t, 3H).

Preparation of 9A:

To a solution of the compound 9.5 (420 mg, 0.84 mmol) in methylene chloride (5 mL) was added a 2.0M anhydrous solution of hydrogen chloride in diethyl ether (15 mL). The reaction was stirred at room temperature overnight and diluted with diethyl ether. The upper clear solution was decanted and the residue was washed with diethyl ether three times and dissolved in methylene chloride. The resulting solution was concentrated in vacuo to yield 9A isolated as its hydrochloric acid salt. Yield: 100%.

$^1$H NMR (400 MHz, DMSO d$_6$) δ 12.80 (s, 1H), 8.78 (brs, 2H), 7.89 (d, 1H), 7.69 (dd, 1H), 7.20 (d, 1H), 3.28 (m, 4H), 3.10 (m, 2H), 3.0 (m, 2H), 2.81 (m, 2H), 2.60 (d, 1H), 2.30 (t, 2H), 1.91 (m, 2H), 1.60-1.20 (m, 10H), 1.10 (t, 3H), 1.10 (t, 3H). Mass Spectral Analysis m/z=401.5 (M+H)$^+$ Example 9B Preparation of 9.7a:

To a solution of the carboxylic acid 9.5 (500 mg, 1.0 mmol) in acetonitrile (35 mL) was added N,N-diisopropylethylamine (1.18 mL, 6.71 mmol) and a 0.5M solution of ammonia in 1,4-dioxane (9.6a) (20 mL, 10 mmol). The reaction mixture was cooled with ice-bath and TBTU (389 mg, 0.00121 mol) was added in small portions. The reaction mixture was stirred at room temperature overnight and concentrated in vacuo. The residue was dissolved in ethyl acetate. The solution was washed with saturated aqueous sodium bicarbonate and dried over sodium sulfate. Evaporation of the solvent provided the crude product, which was chromatographed using acetone/hexane (1:1) as eluent to yield the amide 9.7a. Yield: 90%.

$^1$H NMR (400 MHz, CDCl$_3$) δ 7.80 (d, 1H), 7.60 (dd, 1H), 7.10 (d, 1H), 7.0 (brs, 1H), 5.56 (brs, 1H), 3.46-3.30 (m, 8H), 2.88 (m, 1H), 2.72 (d, 1H), 2.57 (d, 1H), 2.37 (t, 2H), 1.89 (m, 3H), 1.70 (m, 2H), 1.46 (s, 9H), 1.40-1.28 (m, 7H), 1.18 (t, 3H), 1.09 (t, 3H).

Preparation of 9B:

To a solution of amide 9.7a (450 mg, 0.9 mmol) in methylene chloride (5 mL) was added a 2.0M anhydrous solution of hydrogen chloride in diethyl ether (15 mL). The reaction was stirred for 6 hours at room temperature. Diethyl ether (80 mL) was added to the reaction mixture, which was stirred at room temperature for 2 days. The upper clear solution was decanted and the residue was washed with diethyl ether three times and dissolved in methylene chloride. The resulting solution was concentrated in vacuo to yield 9B isolated as its hydrochloric acid salt. Yield: 93%.

$^1$H NMR (400 MHz, DMSO d$_6$) δ 8.80 (brs, 2H), 7.92 (s, 1H), 7.80 (d, 1H), 7.60 (dd, 1H), 7.29 (s, 1H), 7.12 (d, 1H), 3.30 (m, 4H), 3.15 (m, 2H), 3.0 (m, 2H), 2.80 (m, 2H), 2.58 (d, 1H), 2.30 (t, 2H), 1.98 (m, 2H), 1.60-1.20 (m, 10H), 1.10 (t, 3H), 1.0 (t, 3H).

Mass Spectral Analysis m/z=400.5 (M+H)$^+$

Example 9C

Preparation of 9C:

9C (hydrochloric acid salt) was obtained according to a procedure similar to the one described for 9B (hydrochloric acid salt) with the following exception: Step 9.7: 9.6a was replaced by 9.6b.

$^1$H NMR (400 MHz, DMSO d$_6$) δ 8.88 (brs, 2H), 8.40 (brs, 1H), 7.79 (d, 1H), 7.58 (dd, 1H), 7.12 (d, 1H), 3.28 (m, 4H), 3.11 (m, 2H), 3.0 (m, 2H), 2.80 (m, 5H), 2.60 (d, 1H), 2.30 (t, 2H), 1.98 (m, 2H), 1.60-1.20 (m, 10H), 1.10 (t, 3H), 1.0 (t, 3H).

Mass Spectral Analysis m/z=414.5 (M+H)$^+$

Example 9D

Preparation of 9D:

9D (hydrochloric acid salt) was obtained according to a procedure similar to the one described for 9B (hydrochloric acid salt) with the following exception: Step 9.7: 9.6a was replaced by 2.3c.

$^1$H NMR (400 MHz, DMSO d$_6$) δ 8.80 (brs, 2H), 8.40 (t, 1H), 7.80 (d, 1H), 7.60 (dd, 1H), 7.12 (d, 1H), 3.28 (m, 6H), 3.10 (m, 2H), 3.0 (m, 2H), 2.80 (m, 2H), 2.56 (d, 1H), 2.30 (t, 2H), 1.98 (m, 2H), 1.60-1.20 (m, 10H), 1.10 (m, 6H), 1.0 (t, 3H).

Mass Spectral Analysis m/z=428.5 (M+H)$^+$

TABLE A

| Example | Structure | [M + H]$^+$ |
|---|---|---|
| 1A | 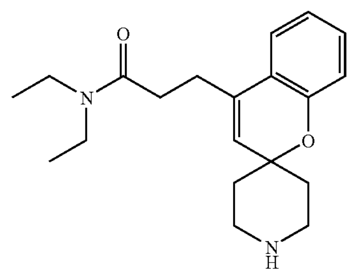 | 329.0 |
| 1B | 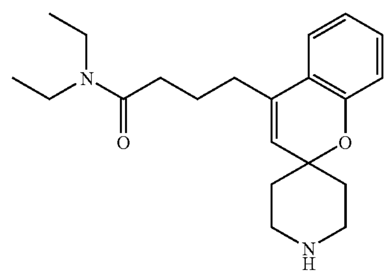 | 343.0 |
| 1C | 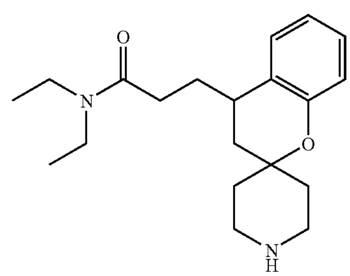 | 331.0 |
| 1D | 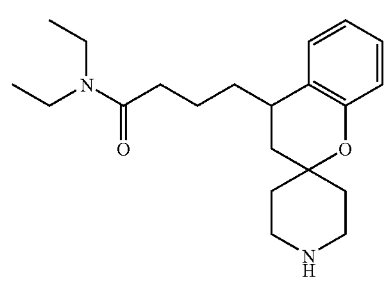 | 345.0 |

TABLE A-continued

| Example | Structure | [M + H]+ |
|---|---|---|
| 1E | ethyl 4-(spiro[chromene-2,4'-piperidin]-4-yl)butanoate | 316.0 |
| 2A | N,N-diisopropyl-4-(spiro[chromane-2,4'-piperidin]-4-yl)butanamide | 373.4 |
| 2B | 2-(4-(spiro[chromane-2,4'-piperidin]-4-yl)butanoyl)isoindoline | 391.3 |
| 2C | N-ethyl-4-(spiro[chromane-2,4'-piperidin]-4-yl)butanamide | 317.3 |
| 2D | N-butyl-4-(spiro[chromane-2,4'-piperidin]-4-yl)butanamide | 345 |

TABLE A-continued

| Example | Structure | [M + H]+ |
|---|---|---|
| 2E | N,N-diethyl-5-(spiro[chromane-2,4'-piperidin]-4-yl)pentanamide | 359.4 |
| 2F | N,N-diethyl-6-(spiro[chromane-2,4'-piperidin]-4-yl)hexanamide | 373.5 |
| 2G | N,N-diisopropyl-6-(spiro[chromane-2,4'-piperidin]-4-yl)hexanamide | 401.5 |
| 3A | N,N-diethyl-5-(6-fluoro-spiro[chromane-2,4'-piperidin]-4-yl)pentanamide | 377.4 |
| 3B | N,N-diethyl-5-(5-methoxy-spiro[chromane-2,4'-piperidin]-4-yl)pentanamide | 389.4 |

TABLE A-continued

| Example | Structure | [M + H]+ |
|---|---|---|
| 3C | 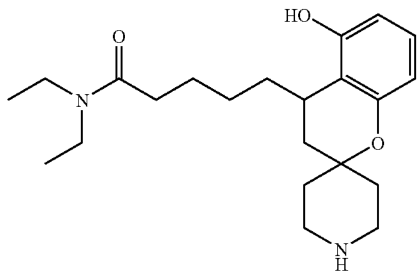 | 375.8 |
| 4A | 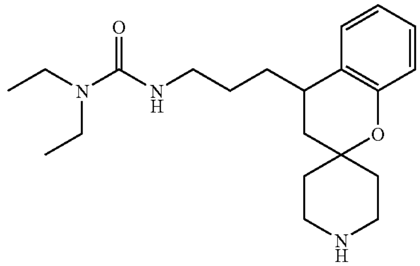 | 360.4 |
| 4B | 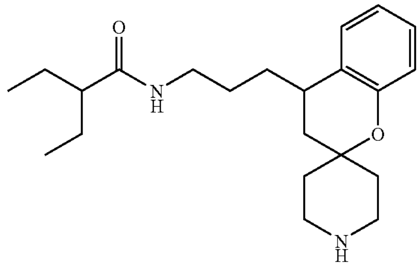 | 359.4 |
| 4C | 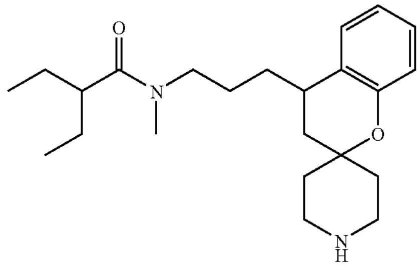 | 373.4 |
| 4D | 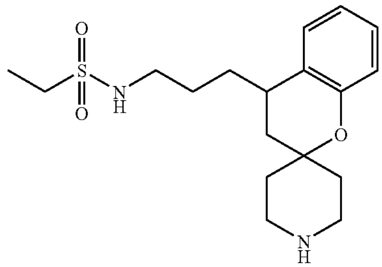 | 353.3 |
| 4E | 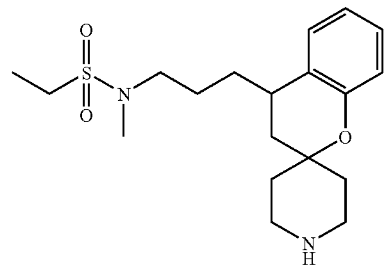 | 367.7 |
| 5A | 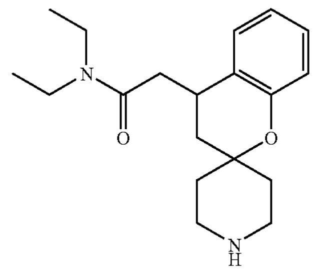 | 317.3 |
| 5B | 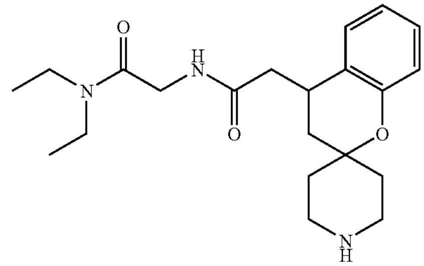 | 374.3 |
| 6A | 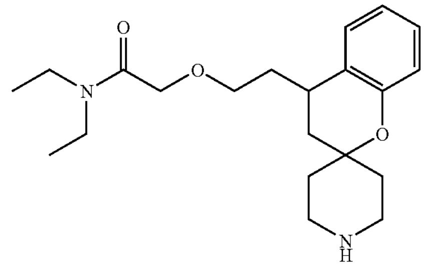 | 361.4 |
| 7A | 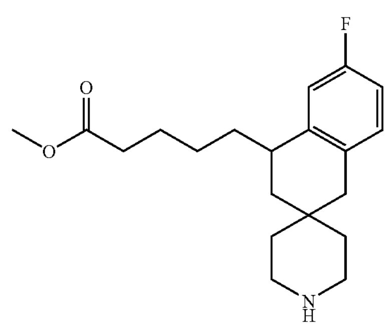 | 334.3 |

TABLE A-continued
| Example | Structure | [M + H]+ |
|---|---|---|
| 7B | 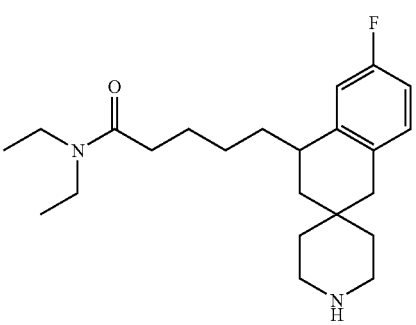 | 375.4 |
| 8A | 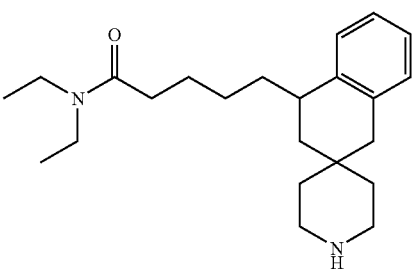 | 357.4 |
| 8B | 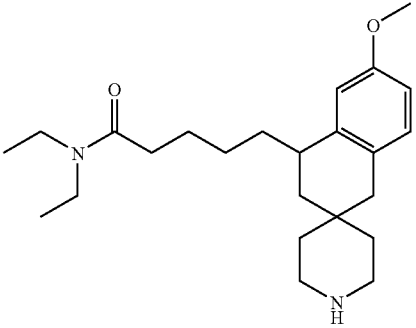 | 387.4 |
| 8C | 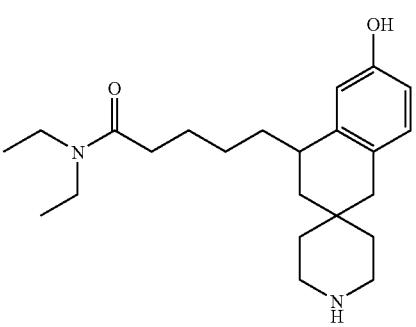 | 373.4 |
| 9A | 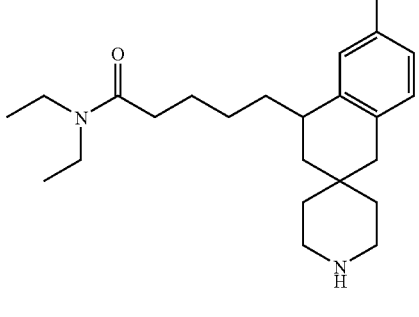 | 401.5 |
| 9B | 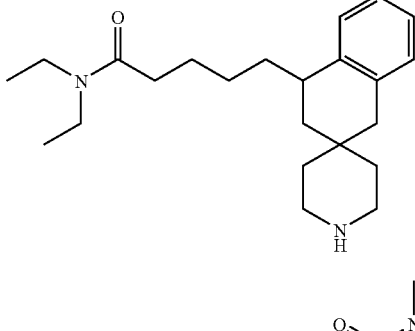 | 400.5 |
| 9C | 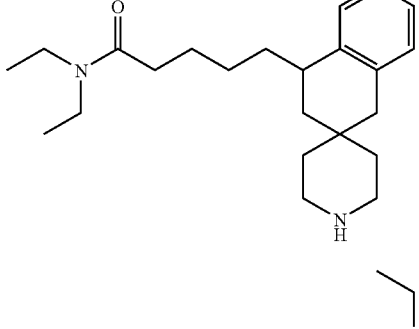 | 414.5 |
| 9D | 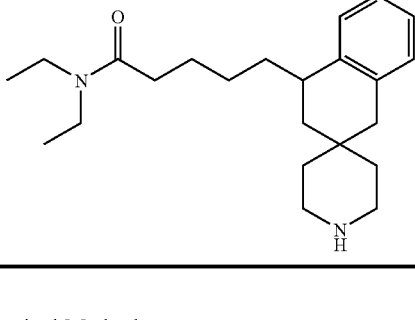 | 428.5 |
E. Biological Methods
The potencies of the final compounds found in Examples 1A-9D were determined by testing the ability of a range of concentrations of each compound to inhibit the binding of the non-selective opioid antagonist, [$^3$H]diprenorphine, to the cloned human μ, δ and δ opioid receptors, expressed in separate cell lines. IC$_{50}$ values were obtained by nonlinear analysis of the data using GraphPad Prism version 3.00 for Windows (GraphPad Software, San Diego). K$_i$ values were obtained by Cheng-Prusoff corrections of IC$_{50}$ values.

Receptor Binding

The receptor binding method (DeHaven and DeHaven-Hudkins, 1998) was a modification of the method of Raynor et al. (1994). After dilution in buffer A and homogenization as before, membrane proteins (10-80 μg) in 250 μL were added to mixtures containing test compound and [$^3$H]diprenorphine (0.5 to 1.0 nM, 40,000 to 50,000 dpm) in 250 μL of buffer A in 96-well deep-well polystyrene titer plates (Beckman). After incubation at room temperature for one hour, the samples were filtered through GF/B filters that had been presoaked in a solution of 0.5% (w/v) polyethylenimine and 0.1% (w/v) bovine serum albumin in water. The filters were rinsed 4 times with 1 mL of cold 50 mM Tris HCl, pH 7.8 and radioactivity remaining on the filters determined by scintillation spectroscopy. Nonspecific binding was determined by the minimum values of the titration curves and was confirmed by separate assay wells containing 10 μM naloxone. K$_i$ values were determined by Cheng-Prusoff corrections of IC$_{50}$ values derived from nonlinear regression fits of 12 point titration curves using GraphPad Prism® version 3.00 for Windows (GraphPad Software, San Diego, Calif.).

To determine the equilibrium dissociation constant for the inhibitors (K$_i$), radioligand bound (cpm) in the presence of various concentrations of test compounds was measured. The concentration to give half-maximal inhibition (EC$_{50}$) of radioligand binding was determined from a best nonlinear regression fit to the following equation, $$Y = \text{Bottom} + \frac{(\text{Top} - \text{Bottom})}{1 + 10^{X - LogEC50}}$$

where Y is the amount of radioligand bound at each concentration of test compound, Bottom is the calculated amount of radioligand bound in the presence of an infinite concentration of test compound, Top is the calculated amount of radioligand bound in the absence of test compound, X is the logarithm of the concentration of test compound, and LogEC$_{50}$ is the log of the concentration of test compound where the amount of radioligand bound is half-way between Top and Bottom. The nonlinear regression fit was performed using the program Prism® (GraphPad Software, San Diego, Calif.). The K$_i$ values were then determined from the EC$_{50}$ values by the following equation, $$K_i = \frac{EC_{50}}{1 + \frac{[ligand]}{K_d}}$$

where [ligand] is the concentration of radioligand and K$_d$ is the equilibrium dissociation constant for the radioligand.

Receptor-mediated [$^{35}$S]GTPγS Binding

The potency and efficacy of compounds at each of the receptors are assessed by modifications of the methods of Selley, et al., 1997 and Traynor and Nahorski, 1995 using receptor-mediated [S]GTPγS binding in the same membrane preparations used to measure receptor binding. Assays are carried out in 96-well FlashPlates® (Perkin Elmer Life Sciences, Inc, Boston, Mass.). Membranes prepared from CHO cells expressing the appropriate receptor (50-100 μg of protein) are added to assay mixtures containing agonist with or without antagonists, 100 pM [$^{35}$S]GTPγS (approx. 100,000 dpm), 3.0 μM GDP, 75 mM NaCl, 15 mM MgCl$_2$, 1.0 mM ethylene glycol-bis(β-aminoethyl ether)-N,N,N',N'-tetracetic acid, 1.1 mM dithiothreitol, 10 μg/mL leupeptin, 10 μg/mL pepstatin A, 200 μg/mL bacitracin, and 0.5 μg/mL aprotinin in 50 mM Tris-HCl buffer, pH 7.8. After incubation at room temperature for one hour, the plates are sealed, centrifuged at 800×g in a swinging bucket rotor for 5 minutes and bound radioactivity determined with a TopCount microplate scintillation counter (Packard Instrument Co., Meriden, Conn.).

EC$_{50}$ values for agonists are determined from nonlinear regression fits of 8- or 12-point titration curves to the 4-parameter equation for a sigmoidal dose-response with a slope factor of 1.0 using GraphPad Prism® version 3.00 for Windows (GraphPad Software, San Diego, Calif.).

To determine IC$_{50}$ values, the concentrations to give half-maximal inhibition of agonist-stimulated [$^{35}$S]GTPγS binding, the amount of [$^{35}$S]GTPγS bound in the presence of a fixed concentration of agonist and various concentrations of antagonist was measured. The fixed concentration of agonist was the EC$_{80}$, the concentration to give 80% of the relative maximum stimulation of [$^{35}$S]GTPγS binding. The agonists loperamide (100 nM), U50,488 (50 nM), and BW373U86 (2.0 nM) were used to stimulate [$^{35}$S]GTPγS binding via the μ, δ, and κ opioid receptors, respectively. The IC$_{50}$ value was determined from a best nonlinear regression fit of the data to the 4-parameter equation for a sigmoidal dose-response with a slope factor of 1.0 using GraphPad Prism® version 3.00 for Windows.

F. Biological Results

The potencies of the compounds were determined by testing the ability of a range of concentrations of each compound to inhibit the binding of the non-selective opioid antagonist, [$^3$H]diprenorphine, to the cloned human μ, κ, and δ opioid receptors, expressed in separate cell lines. All the compounds tested (Examples 1A-9D) bind with high affinity to the human cloned δ opioid receptor. These compounds display high selectivity δ/κ and δ/μ. The potencies of the ligands were assessed by their abilities to stimulated [$^{35}$S]GTPγS binding to membranes containing the cloned human δ opioid receptors. All the compounds tested were agonists at δ opioid receptor with EC$_{50}$ values in the nanomolar range. Example 9D (ADC02066447) (Table 1) binds to the μ, δ and κ opioid receptors with affinity (expressed as K$_i$ value) of 632 nM, 0.47 nM and 696nM, respectively. Furthermore, Example 9D displayed potent in vitro δ agonist activity (EC$_{50}$=8.1 nM).

When ranges are used herein, such as carbon ranges or dosage ranges, all combinations and subcombinations of ranges and specific embodiments therein are intended to be included.

The disclosures of each patent, patent application and publication cited or described in this document are hereby incorporated herein by reference, in their entirety.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A compound of formula I:

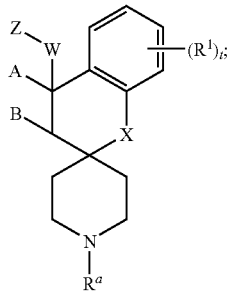

wherein:
W is alkylene;
Z is alkoxy, —C(=O)—R$^2$, —NR$^3$—C(=O)—R$^4$, or —NR$^3$S(=O)$_m$alkyl;
each R$^1$ is independently carboxy, hydroxy, alkoxy, halo, aminocarbonyl, N-alkylaminocarbonyl, or N,N-dialkylaminocarbonyl;
R$^2$ is —NR$^5$R$^6$ or alkoxy;
R$^3$ and R$^a$ are each independently H or alkyl;
R$^4$ is alkyl or —NR$^5$R$^6$;
R$^5$ and R$^6$ are each independently H or alkyl, or R$^5$ and R$^6$ taken together with the nitrogen atom to which they are connected form a 3- to 8-membered heterocycloalkyl ring in which 1 or 2 of the heterocycloalkyl ring carbon atoms independently may each be optionally replaced by —O—, —S—, —N(R$^7$)—, —N(R$^8$)—C(=O)—, or —C(=O)—N(R$^9$)—;
R$^7$, R$^8$, and R$^9$ are each independently H or alkyl;
X is —CH$_2$— or —O—;
A and B are each H, or taken together with the carbon atoms through which they are connected form a double bond; and
t is 0, 1 or 2;
or a pharmaceutically acceptable salt thereof.

2. A compound according to claim 1, wherein A and B are each H.

3. A compound according to claim 1, wherein A and B are taken together with the carbon atoms through which they are connected to form a double bond.

4. A compound according to claim 1, wherein X is —O—.

5. A compound according to claim 1, wherein X is —CH$_2$—.

6. A compound according to claim 1, wherein R$^a$ is H.

7. A compound according to claim 1, wherein Z is —C(=O)—R$^2$.

8. A compound according to claim 7, wherein R$^2$ is —NR$^5$R$^6$.

9. A compound according to claim 8, wherein R$^5$ and R$^6$ are each independently H or alkyl.

10. A compound according to claim 9, wherein R$^5$ and R$^6$ are each independently H or C$_{1-4}$alkyl.

11. A compound according to claim 10, wherein R$^5$ and R$^6$ are each independently C$_{1-4}$alkyl.

12. A compound according to claim 11, wherein R$^5$ and R$^6$ are each independently C$_{2-3}$alkyl.

13. A compound according to claim 6, having the formula II:

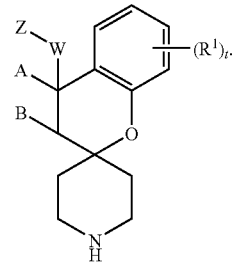

14. A compound according to claim 13, wherein A and B are taken together with the carbon atoms through which they are connected to form a double bond.

15. A compound according to claim 14, wherein Z is —C(=O)—R$^2$, —NR$^3$—C(=O)—R$^4$, or —NR$^3$S(=O)$_2$alkyl.

16. A compound according to claim 15, wherein Z is —C(=O)—R$^2$.

17. A compound according to claim 16, wherein R$^2$ is —NR$^5$R$^6$.

18. A compound according to claim 17, wherein R$^5$ and R$^6$ are each independently C$_{2-3}$alkyl.

19. A compound according to claim 18, wherein t is 0.

20. A compound according to claim 13, wherein A and B are each H.

21. A compound according to claim 20, having the formula III:

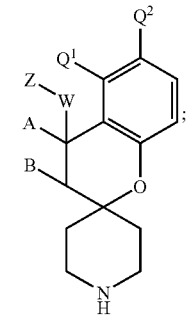

wherein:
Q$^1$ and Q$^2$ are each independently H, carboxy, hydroxy, alkoxy, halo, aminocarbonyl, N-alkylaminocarbonyl, or N,N-dialkylaminocarbonyl.

22. A compound according to claim 21, wherein Z is —C(=O)—R$^2$, —NR$^3$—C(=O)—R$^4$, or —NR$^3$S(=O)$_2$alkyl.

23. A compound according to claim 22, wherein Z is —C(=O)—R$^2$.

24. A compound according to claim 23, wherein R$^2$ is —NR$^5$R$^6$.

25. A compound according to claim 24, wherein R$^5$ and R$^6$ are each independently C$_{2-3}$alkyl.

26. A compound according to claim 25, wherein at least one of Q$^1$ and Q$^2$ is H.

27. A compound according to claim 26, wherein Q$^1$ and Q$^2$ are each H.

28. A compound according to claim 26, wherein one of Q$^1$ and Q$^2$ is carboxy, hydroxy, alkoxy, halo, aminocarbonyl, or N-alkylaminocarbonyl.

29. A compound according to claim 28, wherein the halo is fluoro and the N-alkylaminocarbonyl is N-$C_{1-3}$alkylaminocarbonyl.

30. A compound according to claim 29, wherein $Q^2$ is carboxy, hydroxy, alkoxy, fluoro, aminocarbonyl, or N-$C_{1-3}$alkylaminocarbonyl.

31. A compound according to claim 28, wherein $Q^1$ is hydroxy or alkoxy.

32. A compound according to claim 6, having the formula IV:

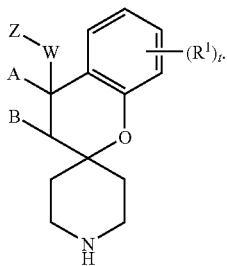

IV

33. A compound according to claim 32, wherein A and B are taken together with the carbon atoms through which they are connected to form a double bond.

34. A compound according to claim 33, wherein Z is —C(=O)—$R^2$, —$NR^3$—C(=O)—$R^4$, or —$NR^3$S(=O)$_2$alkyl.

35. A compound according to claim 34, wherein Z is —C(=O)—$R^2$.

36. A compound according to claim 35, wherein $R^2$ is —$NR^5R^6$.

37. A compound according to claim 36, wherein $R^5$ and $R^6$ are each independently $C_{2-3}$alkyl.

38. A compound according to claim 37, wherein t is 0.

39. A compound according to claim 32, wherein A and B are each H.

40. A compound according to claim 39, having the formula V:

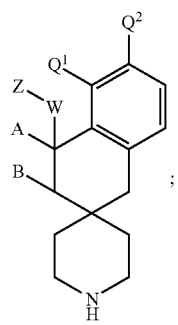

V wherein:
$Q^1$ and $Q^2$ are each independently H, carboxy, hydroxy, alkoxy, halo, aminocarbonyl, N-alkylaminocarbonyl, or N,N-dialkylaminocarbonyl.

41. A compound according to claim 40, wherein Z is —C(=O)—$R^2$, —$NR^3$—C(=O)—$R^4$, or —$NR^3$S(=O)$_2$alkyl.

42. A compound according to claim 41, wherein Z is —C(=O)—$R^2$.

43. A compound according to claim 42, wherein $R^2$ is —$NR^5R^6$.

44. A compound according to claim 43, wherein $R^5$ and $R^6$ are each independently $C_{2-3}$alkyl.

45. A compound according to claim 44, wherein at least one of $Q^1$ and $Q^2$ is H.

46. A compound according to claim 45, wherein $Q^1$ and $Q^2$ are each H.

47. A compound according to claim 45, wherein one of $Q^1$ and $Q^2$ is carboxy, hydroxy, alkoxy, halo, aminocarbonyl, or N-alkylaminocarbonyl.

48. A compound according to claim 46, wherein the halo is fluoro and the N-alkylaminocarbonyl is N—$C_{1-3}$alkylaminocarbonyl.

49. A compound according to claim 47, wherein $Q^2$ is carboxy, hydroxy, alkoxy, fluoro, aminocarbonyl, or N—$C_{1-3}$alkylaminocarbonyl.

50. A compound according to claim 47, wherein $Q^1$ is hydroxy or alkoxy.

51. A compound according to claim 1, selected from the group consisting of:
  4-[2-(N,N-diethylaminocarbonyl)ethyl]-spiro[2H,1-benzopyran-2,4'-piperidine];
  4-[3-(N,N-diethylaminocarbonyl)propyl]-spiro[2H,1-benzopyran-2,4'-piperidine];
  4-[2-(N,N-diethylaminocarbonyl)ethyl]-spiro[3,4-dihydro-2H,1-benzopyran-2,4'-piperidine];
  4-[3-(N,N-diethylaminocarbonyl)propyl]-spiro[3,4-dihydro-2H,1-benzopyran-2,4'-piperidine];
  4-[3-(ethoxycarbonyl)propyl]-spiro[2H,1-benzopyran-2,4'-piperidine];
  4-[3-(N,N-diisopropylaminocarbonyl)propyl]-spiro[3,4-dihydro-2H,1-benzopyran-2,4'-piperidine];
  4-[3-(1-(isoindolin-2-yl)carbonyl)propyl]-spiro[3,4-dihydro-2H,1-benzopyran-2,4'-piperidine];
  4-[3-(N-ethylaminocarbonyl)propyl]-spiro[3,4-dihydro-2H,1-benzopyran-2,4'-piperidine];
  4-[3-(N-butylaminocarbonyl)propyl]-spiro[3,4-dihydro-2H,1-benzopyran-2,4'-piperidine];
  4-[4-(N,N-diethylaminocarbonyl)butyl]-spiro[3,4-dihydro-2H,1-benzopyran-2,4'-piperidine];
  4-[5-(N,N-diethylaminocarbonyl)pentyl]-spiro[3,4-dihydro-2H,1-benzopyran-2,4'-piperidine];
  4-[5-(N,N-diisopropylaminocarbonyl)pentyl]-spiro[3,4-dihydro-2H,1-benzopyran-2,4'-piperidine];
  4-[4-(N,N-diethylaminocarbonyl)butyl]-spiro[6-fluoro-3,4-dihydro-2H,1-benzopyran-2,4'-piperidine];
  4-[4-(N,N-diethylaminocarbonyl)butyl]-spiro[5-methoxy-3,4-dihydro-2H,1-benzopyran-2,4'-piperidine];
  4-[4-(N,N-diethylaminocarbonyl)butyl]-spiro[5-hydroxy-3,4-dihydro-2H,1-benzopyran-2,4'-piperidine];
  4-[3-(N,N-diethylaminocarbonylamino)propyl]-spiro[3,4-dihydro-2H,1-benzopyran-2,4'-piperidine];
  4-[3-(N-(2-ethylbutanoyl)amino)propyl]-spiro[3,4-dihydro-2H,1-benzopyran-2,4'-piperidine];
  4-[(3-(N-methyl-N-(2-ethylbutanoyl)amino)propyl]-spiro[3,4-dihydro-2H,1-benzopyran-2,4'-piperidine];
  4-[(3-(ethylsulfonylamino)propyl]-spiro[3,4-dihydro-2H,1-benzopyran-2,4'-piperidine];
  4-[(3-(N-methyl-N-(ethylsulfonyl)amino)propyl]-spiro[3,4-dihydro-2H,1-benzopyran-2,4'-piperidine];
  4-[(N,N-diethylaminocarbonyl)methyl]-spiro[3,4-dihydro-2H,1-benzopyran-2,4'-piperidine];
  4-[(N,N-diethylaminocarbonylmethylaminocarbonyl)methyl]-spiro[3,4-dihydro-2H,1-benzopyran-2,4'-piperidine];

4-[(2-(N,N-diethylaminocarbonylmethyloxy)ethyl]-spiro[3,4-dihydro-2H,1-benzopyran-2,4'-piperidine];

4-[(4-(methoxycarbonyl)butyl]-spiro[6-fluoro-1,2,3,4-tetrahydronaphthalene-2,4'-piperidine];

4-[(4-N,N-diethylaminocarbonyl)butyl]-spiro[6-fluoro-1,2,3,4-tetrahydronaphthalene-2,4'-piperidine];

4-[(4-N,N-diethylaminocarbonyl)butyl]-spiro[1,2,3,4-tetrahydronaphthalene-2,4'-piperidine];

4-[(4-N,N-diethylaminocarbonyl)butyl]-spiro[6-methoxy-1,2,3,4-tetrahydronaphthalene-2,4'-piperidine];

4-[(4-N,N-diethylaminocarbonyl)butyl]-spiro[6-hydroxy-1,2,3,4-tetrahydronaphthalene-2,4'-piperidine];

4-[(4-N,N-diethylaminocarbonyl)butyl]-spiro[6-carboxy-1,2,3,4-tetrahydronaphthalene-2,4'-piperidine];

4-[(4-N,N-diethylaminocarbonyl)butyl]-spiro[6-aminocarbonyl-1,2,3,4-tetrahydronaphthalene-2,4'-piperidine];

4-[(4-N,N-diethylaminocarbonyl)butyl]-spiro[6-N-methylaminocarbonyl-1,2,3,4-tetrahydronaphthalene-2,4'-piperidine]; and 4-[(4-N,N-diethylaminocarbonyl)butyl]-spiro[6-N-ethylcarbonyl-1,2,3,4-tetrahydronaphthalene-2,4'-piperidine];

or a pharmaceutically acceptable salt thereof.

52. A compound according to claim 51, selected from the group consisting of:

4-[3-(N,N-diethylaminocarbonyl)propyl]-spiro[3,4-dihydro-2H,1-benzopyran-2,4'-piperidine];

4-[3-(N,N-diisopropylaminocarbonyl)propyl]-spiro[3,4-dihydro-2H,1-benzopyran-2,4'-piperidine];

4-[4-(N,N-diethylaminocarbonyl)butyl]-spiro[3,4-dihydro-2H,1-benzopyran-2,4'-piperidine];

4-[5-(N,N-diethylaminocarbonyl)pentyl]-spiro[3,4-dihydro-2H,1-benzopyran-2,4'-piperidine];

4-[5-(N,N-diisopropylaminocarbonyl)pentyl]-spiro[3,4-dihydro-2H,1-benzopyran-2,4'-piperidine];

4-[4-(N,N-diethylaminocarbonyl)butyl]-spiro[6-fluoro-3,4-dihydro-2H,1-benzopyran-2,4'-piperidine];

4-[4-(N,N-diethylaminocarbonyl)butyl]-spiro[5-hydroxy-3,4-dihydro-2H,1-benzopyran-2,4'-piperidine];

4-[(3-(ethylsulfonylamino)propyl]-spiro[3,4-dihydro-2H,1-benzopyran-2,4'-piperidine];

4-[(4-N,N-diethylaminocarbonyl)butyl]-spiro[6-fluoro-1,2,3,4-tetrahydronaphthalene-2,4'-piperidine];

4-[(4-N,N-diethylaminocarbonyl)butyl]-spiro[1,2,3,4-tetrahydronaphthalene-2,4'-piperidine];

4-[(4-N,N-diethylaminocarbonyl)butyl]-spiro[6-methoxy-1,2,3,4-tetrahydronaphthalene-2,4'-piperidine];

4-[(4-N,N-diethylaminocarbonyl)butyl]-spiro[6-hydroxy-1,2,3,4-tetrahydronaphthalene-2,4'-piperidine];

4-[(4-N,N-diethylaminocarbonyl)butyl]-spiro[6-aminocarbonyl-1,2,3,4-tetrahydronaphthalene-2,4'-piperidine];

4-[(4-N,N-diethylaminocarbonyl)butyl]-spiro[6-N-methylaminocarbonyl-1,2,3,4-tetrahydronaphthalene-2,4'-piperidine]; and 4-[(4-N,N-diethylaminocarbonyl)butyl]-spiro[6-N-ethylcarbonyl-1,2,3,4-tetrahydronaphthalene-2,4'-piperidine];

or a pharmaceutically acceptable salt thereof.

53. A compound according to claim 52, selected from the group consisting of:

4-[3-(N,N-diethylaminocarbonyl)propyl]-spiro[3,4-dihydro-2H,1-benzopyran-2,4'-piperidine];

4-[3-(N,N-diisopropylaminocarbonyl)propyl]-spiro[3,4-dihydro-2H,1-benzopyran-2,4'-piperidine];

4-[4-(N,N-diethylaminocarbonyl)butyl]-spiro[3,4-dihydro-2H,1-benzopyran-2,4'-piperidine];

4-[5-(N,N-diethylaminocarbonyl)pentyl]-spiro[3,4-dihydro-2H,1-benzopyran-2,4'-piperidine];

4-[4-(N,N-diethylaminocarbonyl)butyl]-spiro[6-fluoro-3,4-dihydro-2H,1-benzopyran-2,4'-piperidine];

4-[4-(N,N-diethylaminocarbonyl)butyl]-spiro[5-hydroxy-3,4-dihydro-2H,1-benzopyran-2,4'-piperidine];

4-[(4-N,N-diethylaminocarbonyl)butyl]-spiro[6-hydroxy-1,2,3,4-tetrahydronaphthalene-2,4'-piperidine];

4-[(4-N,N-diethylaminocarbonyl)butyl]-spiro[6-aminocarbonyl-1,2,3,4-tetrahydronaphthalene-2,4'-piperidine];

4-[(4-N,N-diethylaminocarbonyl)butyl]-spiro[6-N-methylaminocarbonyl-1,2,3,4-tetrahydronaphthalene-2,4'-piperidine]; and 4-[(4-N,N-diethylaminocarbonyl)butyl]-spiro[6-N-ethylcarbonyl-1,2,3,4-tetrahydronaphthalene-2,4'-piperidine];

or a pharmaceutically acceptable salt thereof.

54. A compound according to claim 53, selected from the group consisting of:

4-[4-(N,N-diethylaminocarbonyl)butyl]-spiro[5-hydroxy-3,4-dihydro-2H,1-benzopyran-2,4'-piperidine];

4-[(4-N,N-diethylaminocarbonyl)butyl]-spiro[6-hydroxy-1,2,3,4-tetrahydronaphthalene-2,4'-piperidine];

4-[(4-N,N-diethylaminocarbonyl)butyl]-spiro[6-aminocarbonyl-1,2,3,4-tetrahydronaphthalene-2,4'-piperidine];

4-[(4-N,N-diethylaminocarbonyl)butyl]-spiro[6-N-methylaminocarbonyl-1,2,3,4-tetrahydronaphthalene-2,4'-piperidine]; and 4-[(4-N,N-diethylaminocarbonyl)butyl]-spiro[6-N-ethylcarbonyl-1,2,3,4-tetrahydronaphthalene-2,4'-piperidine];

or a pharmaceutically acceptable salt thereof.

55. A pharmaceutical composition, comprising:
a pharmaceutically acceptable carrier; and a compound according to claim 1.

56. A compound according to claim 51 which is selected from the group consisting of:

4-[2-(N,N-diethylaminocarbonyl)ethyl]-spiro[2H,1-benzopyran-2,4'-piperidine];

4-[3-(N,N-diethylaminocarbonyl)propyl]-spiro[2H,1-benzopyran-2,4'-piperidine];

4-[3-(1-(isoindolin-2-yl)carbonyl)propyl]-spiro[3,4-dihydro-2H,1-benzopyran-2,4'-piperidine];

4-[4-(N,N-diethylaminocarbonyl)butyl]-spiro[3,4-dihydro-2H,1-benzopyran-2,4'-piperidine];

4-[4-(N,N-diethylaminocarbonyl)butyl]-spiro[6-fluoro-3,4-dihydro-2H,1-benzopyran-2,4'-piperidine]; and 4-[4-(N,N-diethylaminocarbonyl)butyl]-spiro[5-hydroxy-3,4-dihydro-2H,1-benzopyran-2,4'-piperidine];

or a pharmaceutically acceptable salt thereof.

57. A compound according to claim 56 which is 4-[2-(N,N-diethylaminocarbonyl)-ethyl]-spiro[2H,1-benzopyran-2,4'-piperidine]or a pharmaceutically acceptable salt thereof.

58. A compound according to claim 56 which is 4-[3-(N,N-diethylaminocarbonyl)-propyl]-spiro[2H,1-benzopyran-2,4'-piperidine]or a pharmaceutically acceptable salt thereof.

59. A compound according to claim 56 which is 4-[3-(1-(isoindolin-2-yl)carbonyl)-propyl]-spiro[3,4-dihydro-2H,1-benzopyran-2,4'-piperidine] or a pharmaceutically acceptable salt thereof.

60. A compound according to claim 56 which is 4-[4-(N,N-diethylaminocarbonyl)-butyl]-spiro[3,4-dihydro-2H,1-benzopyran-2,4'-piperidine] or a pharmaceutically acceptable salt thereof.

61. A compound according to claim 56 which is 4-[4-(N,N-diethylaminocarbonyl)-butyl]-spiro[6-fluoro-3,4-dihydro-2H,1-benzopyran-2,4'-piperidine] or a pharmaceutically acceptable salt thereof.

62. A compound according to claim 56 which is 4-[4-(N,N-diethylaminocarbonyl)-butyl]-spiro[5-hydroxy-3,4-dihydro-2H,1-benzopyran-2,4'-piperidine] or a pharmaceutically acceptable salt thereof.

* * * * *